(12) United States Patent
Hermann et al.

(10) Patent No.: US 7,736,292 B2
(45) Date of Patent: Jun. 15, 2010

(54) BRACHYTHERAPY APPARATUS AND METHODS OF USING SAME

(75) Inventors: George D. Hermann, Portola Valley, CA (US); Doug S. Sutton, Pacifica, CA (US); Gail S. Lebovic, McKinney, TX (US); Eduardo Chi Sing, Dana Point, CA (US); Robert R. Bowes, Laguna Hills, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 565 days.

(21) Appl. No.: 11/554,731

(22) Filed: Oct. 31, 2006

(65) Prior Publication Data

US 2007/0167664 A1 Jul. 19, 2007

Related U.S. Application Data

(60) Provisional application No. 60/731,879, filed on Oct. 31, 2005.

(51) Int. Cl.
*A61M 36/12* (2006.01)
*A61M 36/00* (2006.01)
*A61M 36/04* (2006.01)
*A61N 5/00* (2006.01)

(52) U.S. Cl. .................................. 600/7; 600/3; 600/8
(58) Field of Classification Search .................. 600/1–8
See application file for complete search history.

(56) References Cited

U.S. PATENT DOCUMENTS

| 3,060,924 A | 10/1962 | Rush |
| 3,750,653 A | 8/1973 | Simon |
| 3,968,803 A | 7/1976 | Hyman |
| 4,427,005 A | 1/1984 | Tener |
| 4,580,561 A | 4/1986 | Williamson |
| 4,714,074 A | 12/1987 | Rey et al. |
| 4,798,212 A | 1/1989 | Arana |

(Continued)

FOREIGN PATENT DOCUMENTS

DE 3921291 1/1991

(Continued)

OTHER PUBLICATIONS

PCT International Search Report for PCT/US2006/060368, Applicant: BioLucent, Inc., Forms PCT/IB/373, May 15, 2008, 2 pages.

(Continued)

*Primary Examiner*—Charles A Marmor, II
*Assistant Examiner*—Catherine E Burk
(74) *Attorney, Agent, or Firm*—William A. English; Vista IP Law Group LLP

(57) ABSTRACT

Apparatus, systems and methods for delivering brachytherapy to a target tissue region of a human or other mammalian body. In some embodiments, a flexible brachytherapy device is implanted that includes a therapy delivery portion having one or more radioactive sources securely retained thereto, and a tail portion extending from the therapy delivery portion. Once implanted, the tail portion may extend outside the body, where it may be folded and secured flat against the skin. The device may be removed at therapy completion. Other embodiments of the invention are directed to systems and methods for delivering brachytherapy devices to the body.

30 Claims, 37 Drawing Sheets

U.S. PATENT DOCUMENTS

| | | |
|---|---|---|
| 4,936,823 A | 6/1990 | Colvin et al. |
| 4,957,476 A | 9/1990 | Cano |
| 4,976,680 A | 12/1990 | Hayman et al. |
| 5,056,523 A | 10/1991 | Hotchkiss, Jr. et al. |
| 5,106,360 A | 4/1992 | Ishiwara et al. |
| 5,152,741 A | 10/1992 | Farnio |
| 5,235,966 A | 8/1993 | Jamner |
| 5,242,372 A | 9/1993 | Carol |
| 5,279,565 A | 1/1994 | Klein et al. |
| 5,302,168 A | 4/1994 | Hess |
| 5,336,178 A | 8/1994 | Kaplan et al. |
| 5,354,257 A | 10/1994 | Roubin et al. |
| 5,411,466 A | 5/1995 | Hess |
| 5,423,747 A | 6/1995 | Amano |
| 5,429,605 A | 7/1995 | Richling et al. |
| 5,503,613 A | 4/1996 | Weinberger |
| 5,509,900 A | 4/1996 | Kirkman |
| 5,538,502 A | 7/1996 | Johnstone |
| 5,540,659 A | 7/1996 | Teirstein |
| 5,611,767 A | 3/1997 | Williams |
| 5,653,683 A | 8/1997 | D'Andrea |
| 5,678,572 A | 10/1997 | Shaw et al. |
| 5,707,332 A | 1/1998 | Weinberger |
| 5,713,828 A * | 2/1998 | Coniglione ............. 600/7 |
| 5,720,717 A | 2/1998 | D'Andrea |
| 5,730,698 A | 3/1998 | Fischell et al. |
| 5,782,740 A | 7/1998 | Schneiderman |
| 5,840,008 A | 11/1998 | Klein et al. |
| 5,843,163 A | 12/1998 | Wall |
| 5,851,171 A | 12/1998 | Gasson |
| 5,860,909 A * | 1/1999 | Mick et al. ............. 600/7 |
| 5,863,284 A | 1/1999 | Klein |
| 5,882,291 A | 3/1999 | Bradshaw et al. |
| 5,891,091 A | 4/1999 | Teirstein |
| 5,910,102 A | 6/1999 | Hastings |
| 5,913,813 A | 6/1999 | Williams et al. |
| 5,916,143 A | 6/1999 | Apple et al. |
| 5,931,774 A | 8/1999 | Williams et al. |
| 5,938,582 A | 8/1999 | Ciamacco, Jr. et al. |
| 5,942,209 A | 8/1999 | Leavitt et al. |
| 5,976,106 A | 11/1999 | Verin et al. |
| 6,013,019 A | 1/2000 | Fischell et al. |
| 6,022,308 A | 2/2000 | Williams |
| 6,033,357 A | 3/2000 | Ciezki et al. |
| 6,036,632 A | 3/2000 | Whitmore et al. |
| 6,056,722 A | 5/2000 | Jayaraman |
| 6,059,752 A | 5/2000 | Segal |
| 6,071,263 A | 6/2000 | Kirkman |
| 6,074,339 A | 6/2000 | Ganbale et al. |
| 6,083,148 A | 7/2000 | Williams |
| 6,095,967 A * | 8/2000 | Black et al. ............. 600/7 |
| 6,117,064 A | 9/2000 | Apple et al. |
| 6,159,139 A | 12/2000 | Chiu |
| 6,159,141 A | 12/2000 | Apple et al. |
| 6,176,821 B1 | 1/2001 | Crocker et al. |
| 6,179,766 B1 | 1/2001 | Dickerson |
| 6,196,996 B1 | 3/2001 | Teirstein |
| 6,200,256 B1 | 3/2001 | Weinberger |
| 6,200,257 B1 | 3/2001 | Winkler |
| 6,213,976 B1 | 4/2001 | Trerotola |
| 6,217,585 B1 | 4/2001 | Houser et al. |
| 6,221,003 B1 | 4/2001 | Sierocuk et al. |
| 6,221,030 B1 | 4/2001 | Avaltroni |
| 6,234,951 B1 | 5/2001 | Hastings |
| 6,238,374 B1 | 5/2001 | Winkler |
| 6,258,099 B1 | 7/2001 | Mareiro et al. |
| 6,261,320 B1 | 7/2001 | Tam et al. |
| 6,264,599 B1 | 7/2001 | Slater et al. |
| 6,264,631 B1 | 7/2001 | Willis et al. |
| 6,267,775 B1 | 7/2001 | Clerc et al. |
| 6,287,249 B1 | 9/2001 | Tam et al. |
| 6,338,709 B1 | 1/2002 | Geoffrion |
| 6,358,195 B1 | 3/2002 | Green et al. |
| 6,371,904 B1 | 4/2002 | Sirimanne et al. |
| 6,458,069 B1 | 10/2002 | Tam et al. |
| 6,482,178 B1 | 11/2002 | Andrews et al. |
| 6,494,824 B1 | 12/2002 | Apple et al. |
| 6,506,145 B1 | 1/2003 | Bradshaw et al. |
| 6,508,784 B1 | 1/2003 | Shu |
| 6,527,692 B1 | 3/2003 | Weinberger |
| 6,527,693 B2 | 3/2003 | Munro, III et al. |
| 6,540,656 B2 | 4/2003 | Fontayne et al. |
| 6,540,734 B1 | 4/2003 | Chiu et al. |
| 6,554,757 B1 | 4/2003 | Geitz |
| 6,582,353 B1 | 6/2003 | Hastings et al. |
| 6,589,158 B2 | 7/2003 | Winkler |
| 6,592,548 B2 | 7/2003 | Munro, III et al. |
| 6,607,476 B1 | 8/2003 | Barnhart |
| 6,607,478 B2 | 8/2003 | Williams |
| 6,638,206 B2 | 10/2003 | Green et al. |
| 6,641,518 B2 | 11/2003 | Wolfson et al. |
| 6,645,135 B1 | 11/2003 | Bhat |
| 6,648,811 B2 | 11/2003 | Sierocuk et al. |
| 6,659,933 B2 | 12/2003 | Asano |
| 6,673,006 B2 | 1/2004 | Winkler |
| 6,676,667 B2 | 1/2004 | Mareiro et al. |
| 6,685,619 B2 | 2/2004 | Halpern et al. |
| 6,692,460 B1 | 2/2004 | Jayaraman |
| 6,699,170 B1 | 3/2004 | Crocker et al. |
| 6,712,782 B2 * | 3/2004 | Ford ............. 604/24 |
| 6,746,465 B2 | 6/2004 | Diederich et al. |
| 6,752,752 B2 | 6/2004 | Geitz |
| 6,910,999 B2 | 6/2005 | Chin et al. |
| 6,923,754 B2 | 8/2005 | Lubock |
| 6,955,641 B2 | 10/2005 | Lubock |
| 7,041,047 B2 | 5/2006 | Gellman et al. |
| 7,056,276 B2 | 6/2006 | Nakano et al. |
| 7,357,770 B1 | 4/2008 | Cutrer et al. |
| 2001/0007071 A1 | 7/2001 | Koblish |
| 2002/0016583 A1 | 2/2002 | Cragg |
| 2002/0032359 A1 | 3/2002 | Geoffrion et al. |
| 2002/0165427 A1 | 11/2002 | Yachia et al. |
| 2003/0088144 A1 * | 5/2003 | Terwilliger et al. ............. 600/8 |
| 2003/0092957 A1 | 5/2003 | Scott et al. |
| 2003/0114878 A1 | 6/2003 | Diederich et al. |
| 2003/0158515 A1 | 8/2003 | Gonzalez et al. |
| 2003/0163017 A1 | 8/2003 | Tam et al. |
| 2003/0191355 A1 * | 10/2003 | Ferguson ............. 600/3 |
| 2003/0236443 A1 | 12/2003 | Cespedes et al. |
| 2004/0006305 A1 | 1/2004 | Hebert et al. |
| 2004/0068231 A1 | 4/2004 | Blondeau |
| 2004/0087828 A1 | 5/2004 | Green et al. |
| 2004/0116767 A1 * | 6/2004 | Lebovic et al. ............. 600/7 |
| 2004/0127765 A1 | 7/2004 | Seiler et al. |
| 2004/0260142 A1 | 12/2004 | Lovoi |
| 2005/0061533 A1 | 3/2005 | Lovoi |
| 2005/0075662 A1 | 4/2005 | Pederson et al. |
| 2005/0080313 A1 | 4/2005 | Stewart et al. |
| 2005/0090845 A1 | 4/2005 | Boyd |
| 2005/0096647 A1 | 5/2005 | Steinke et al. |
| 2005/0101823 A1 | 5/2005 | Linares et al. |
| 2005/0101860 A1 | 5/2005 | Patrick et al. |
| 2005/0124843 A1 | 6/2005 | Singh |
| 2005/0182286 A1 | 8/2005 | Lubock |
| 2005/0240074 A1 | 10/2005 | Lubock |
| 2006/0015166 A1 | 1/2006 | Kindlein et al. |
| 2006/0020156 A1 | 1/2006 | Shukla |
| 2006/0094923 A1 | 5/2006 | Mate |
| 2006/0100475 A1 | 5/2006 | White |
| 2006/0116546 A1 | 6/2006 | Eng |
| 2006/0173233 A1 | 8/2006 | Lovoi |
| 2006/0173235 A1 | 8/2006 | Lim et al. |
| 2006/0184192 A1 | 8/2006 | Markworth et al. |
| 2006/0199990 A1 | 9/2006 | Rioux et al. |

| | | | |
|---|---|---|---|
| 2006/0235365 A1 | 10/2006 | Terwilliger et al. | |
| 2006/0258895 A1 | 11/2006 | Maschke | |
| 2007/0106108 A1 | 5/2007 | Hermann et al. | |
| 2007/0167667 A1 | 7/2007 | Lubock et al. | |
| 2007/0191668 A1 | 8/2007 | Lubock et al. | |

FOREIGN PATENT DOCUMENTS

| | | | |
|---|---|---|---|
| DE | 3924291 | | 1/1991 |
| EP | 0318447 | B1 | 9/1994 |
| EP | 0390528 | B1 | 1/1997 |
| EP | 0775505 | | 5/1997 |
| EP | 0536888 | B1 | 1/1998 |
| EP | 0906769 | | 4/1999 |
| EP | 0955071 | | 11/1999 |
| EP | 0884977 | B1 | 4/2003 |
| EP | 0782410 | B1 | 12/2003 |
| EP | 0955071 | | 2/2004 |
| EP | 1402922 | | 3/2004 |
| EP | 1405600 | | 4/2004 |
| EP | 0808129 | B1 | 5/2004 |
| EP | 1428477 | | 6/2004 |
| EP | 1568397 | | 8/2005 |
| WO | 00/59378 | | 10/2000 |
| WO | 01/95808 | | 12/2001 |
| WO | 03/077768 | | 9/2003 |
| WO | 03/079907 | | 10/2003 |
| WO | 2005037363 | | 4/2005 |

OTHER PUBLICATIONS

PCT Written Opinion for PCT/US2006/060368, Applicant: BioLucent, Inc., Forms PCT/ISA/237, May 15, 2008, 11 pages.

Attorney for Applicant, Office Actions and Applicant Responses for related U.S. Appl. No. 10/658,518 [CIAN-0101] dated Mar. 28, 2007 to Jun. 10, 2009, 133 pages.

* cited by examiner

Fig. 1B
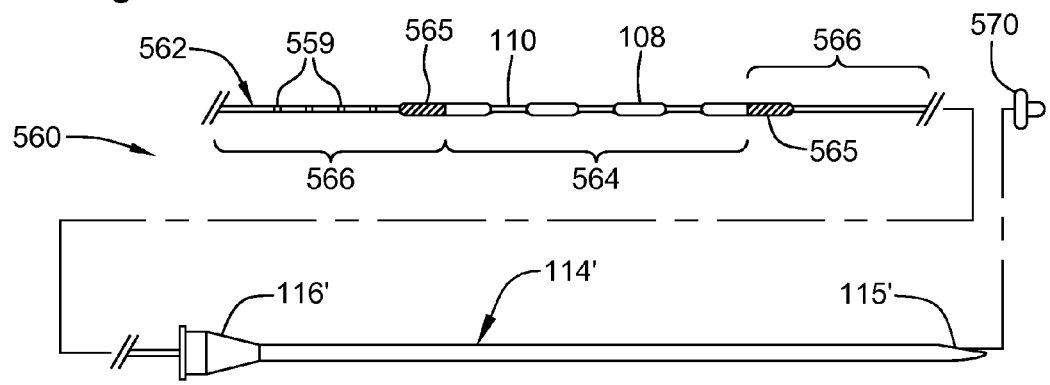
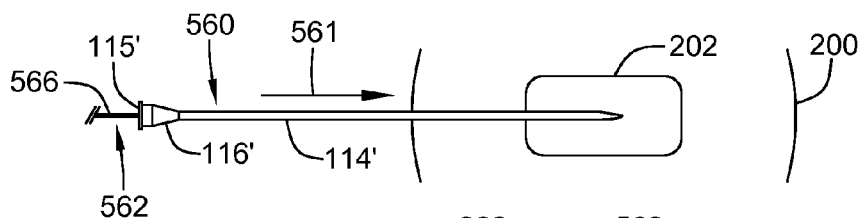
Fig. 2G
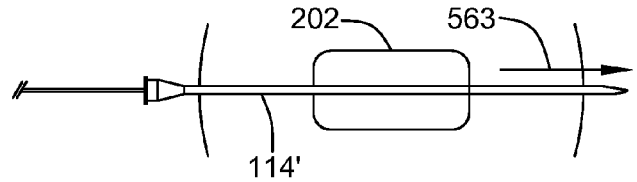
Fig. 2H
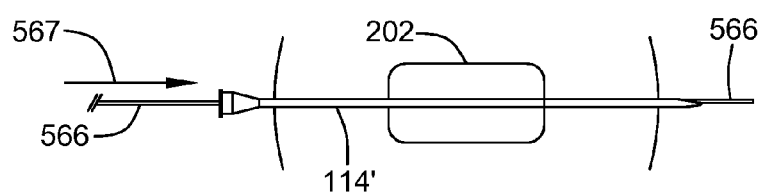
Fig. 2I
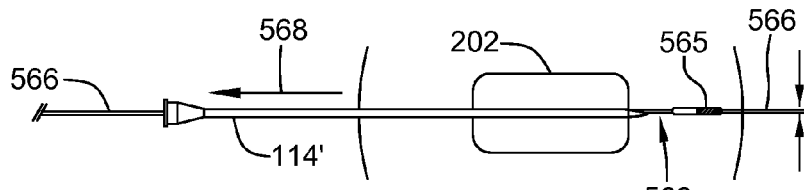
Fig. 2J
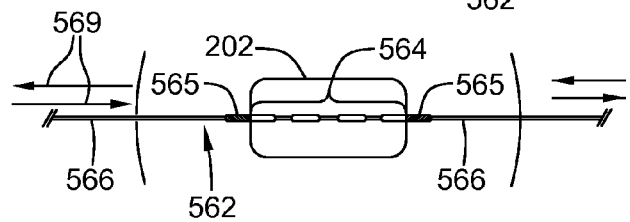
Fig. 2K
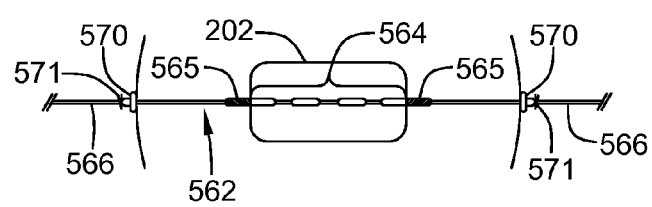
Fig. 2L Fig. 3A
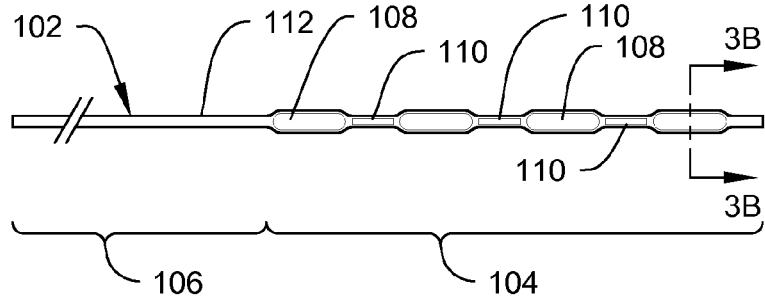
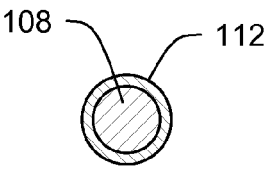
Fig. 3B
Fig. 4A
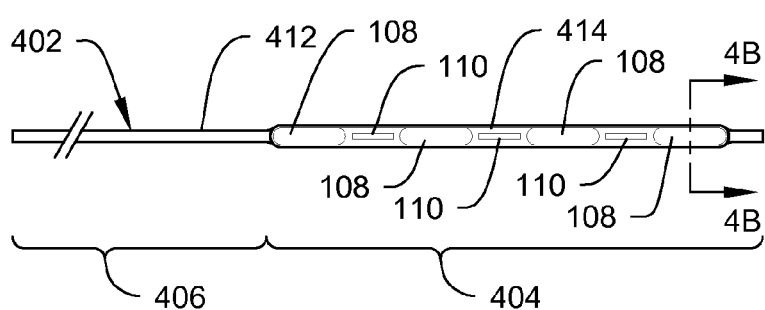
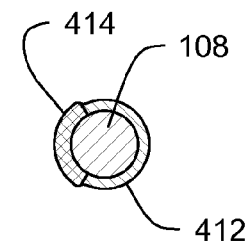
Fig. 4B
Fig. 5A
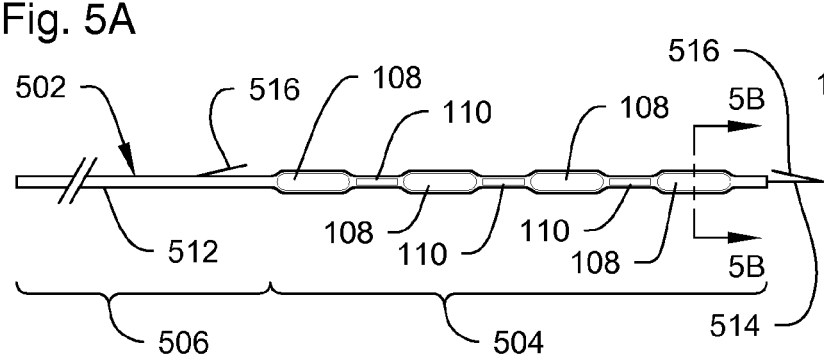
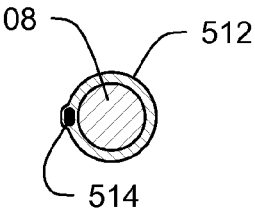
Fig. 5B
Fig. 5C
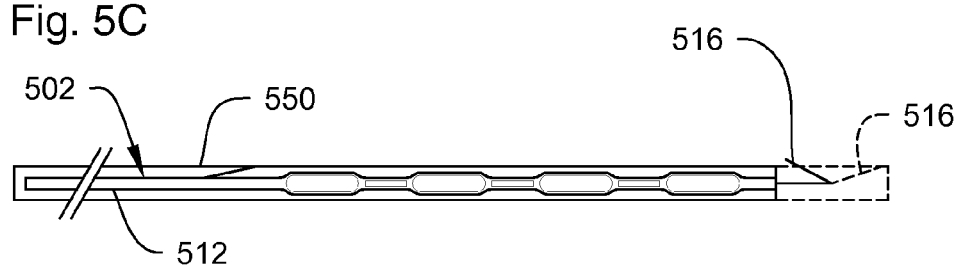

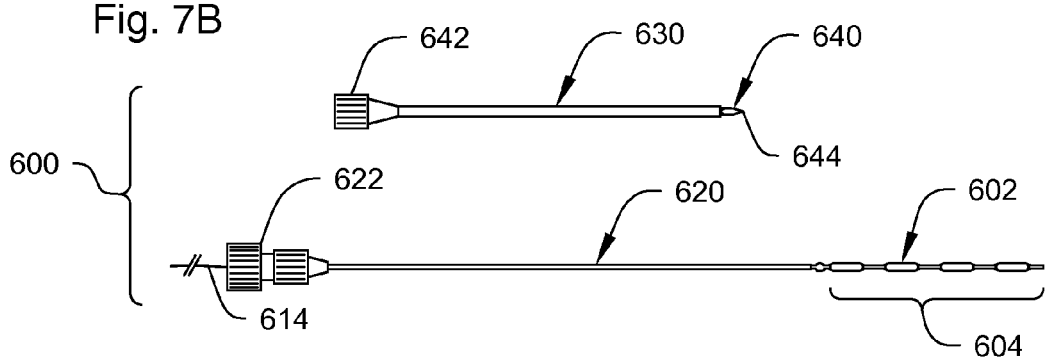
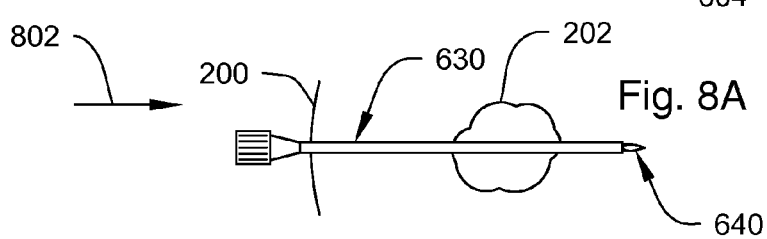
Fig. 8A
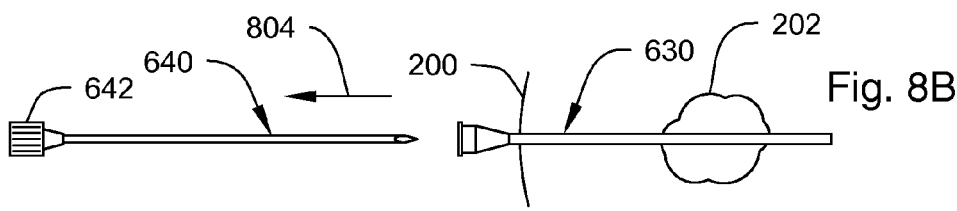
Fig. 8B
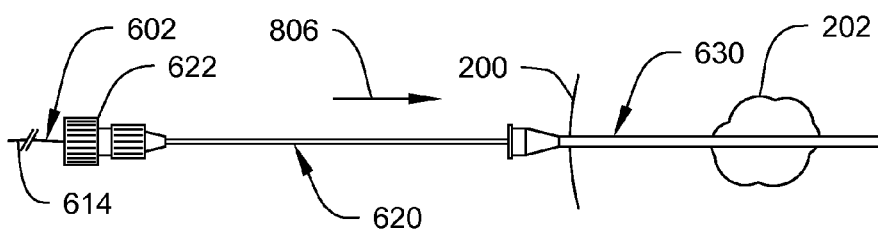
Fig. 8C
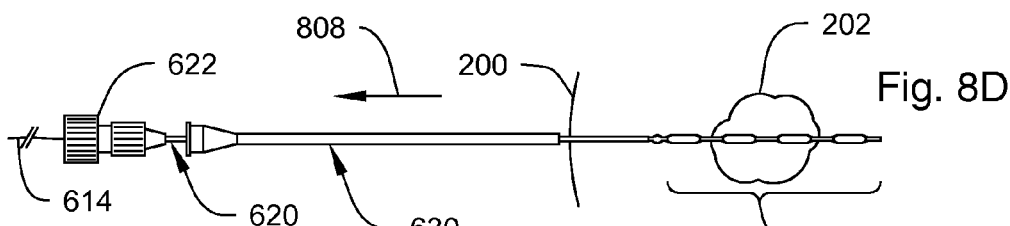
Fig. 8D
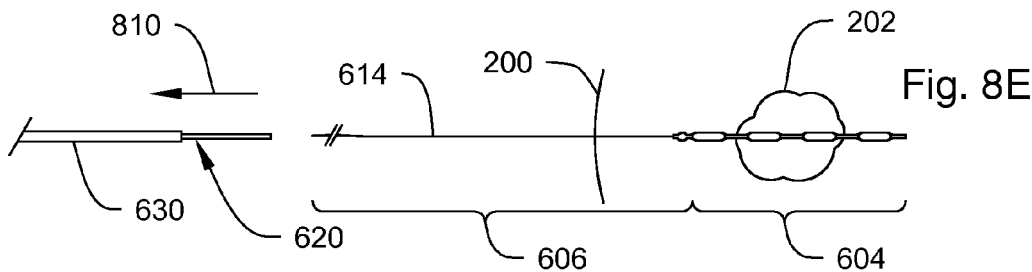
Fig. 8E

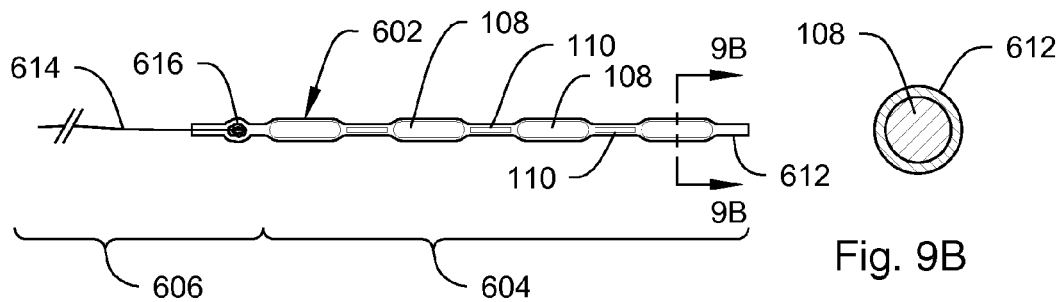
Fig. 9A
Fig. 9B
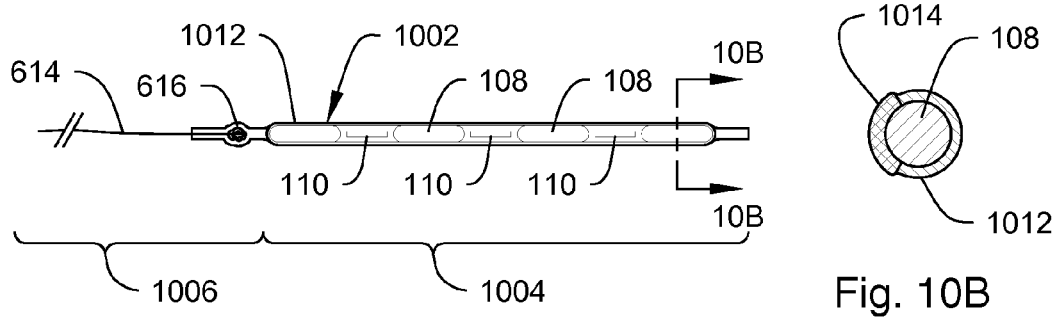
Fig. 10A
Fig. 10B
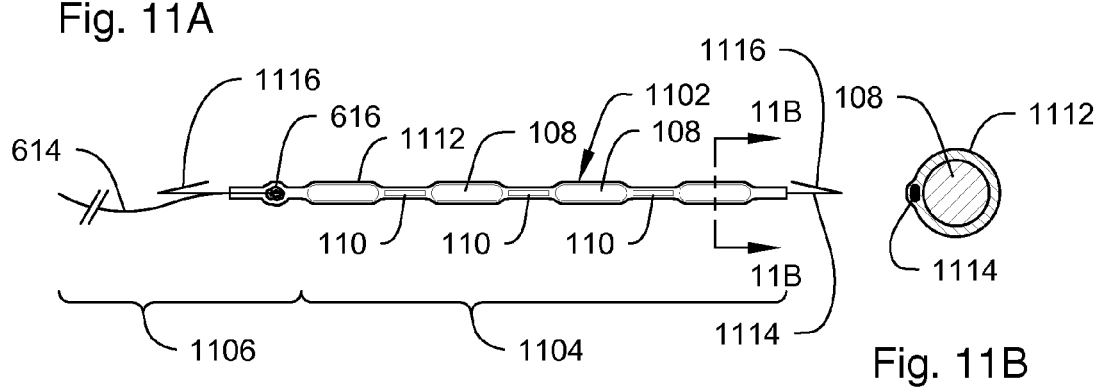
Fig. 11A
Fig. 11B

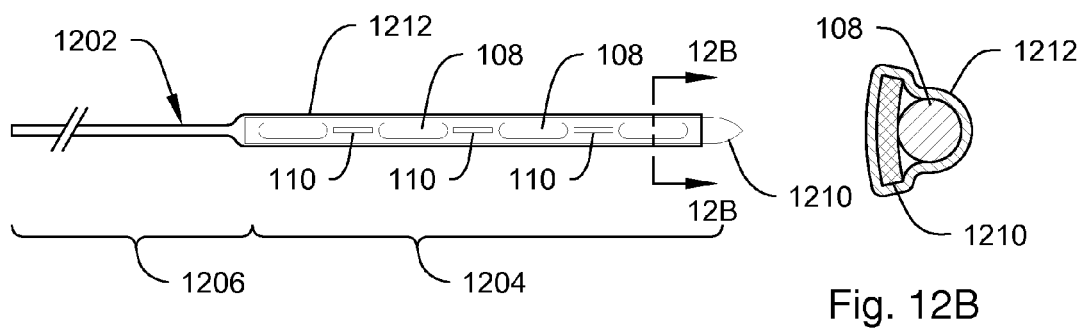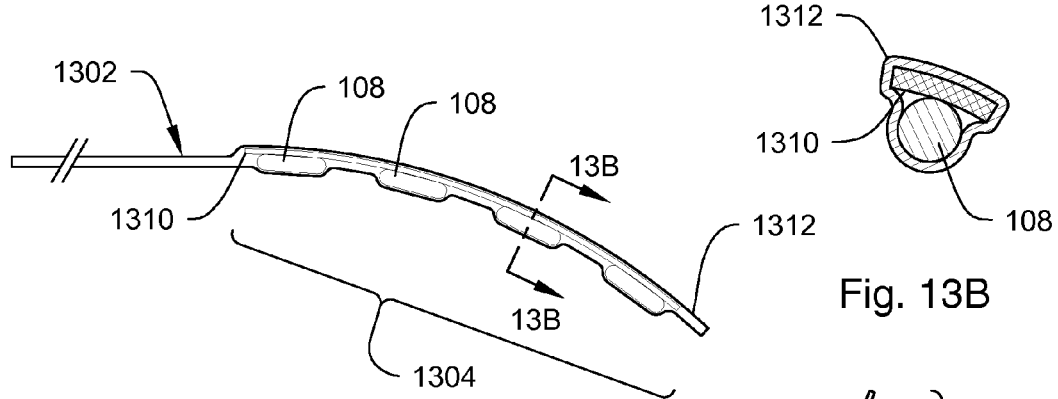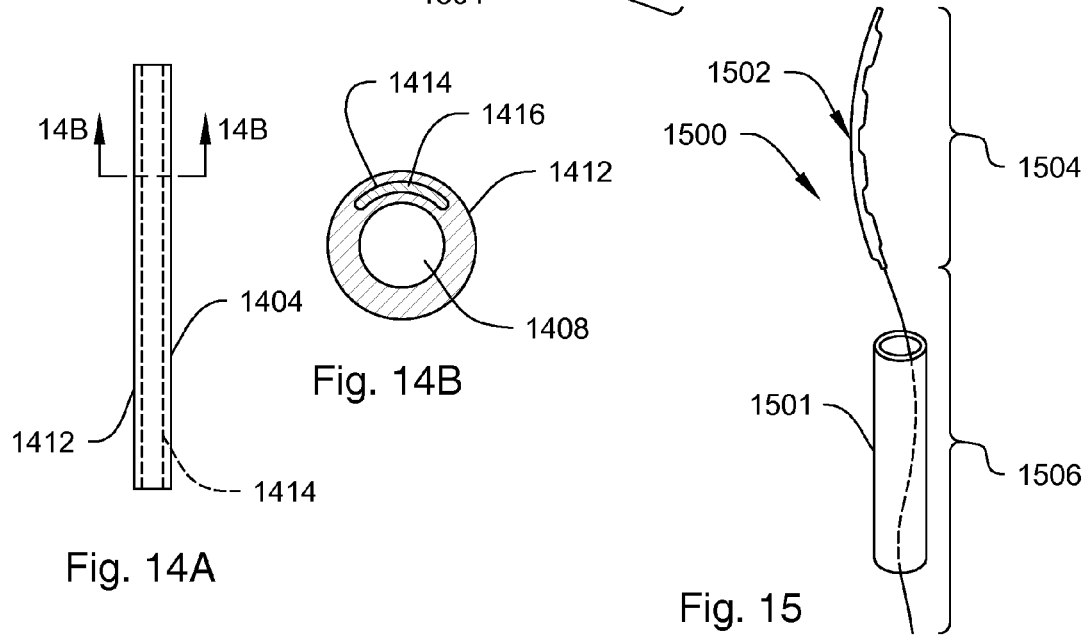

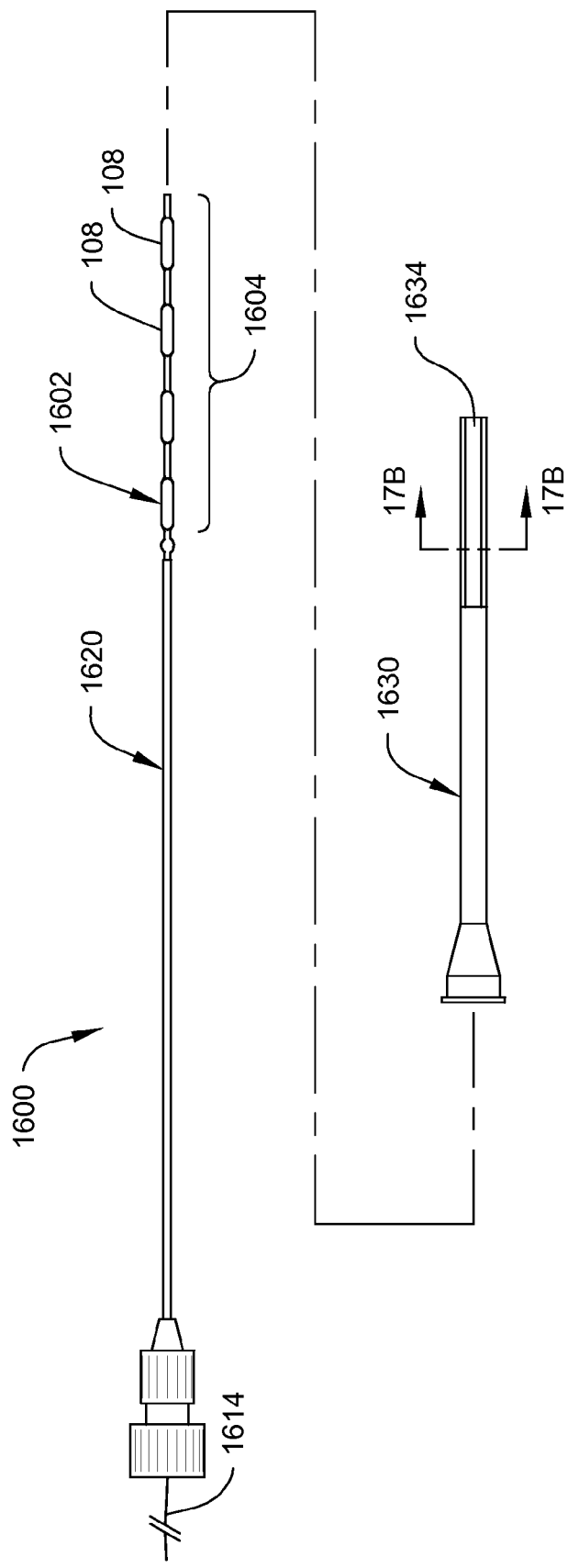
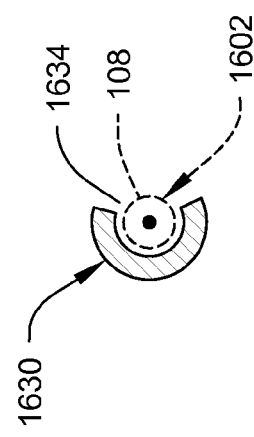
Fig. 17A
Fig. 17B

BRACHYTHERAPY APPARATUS AND METHODS OF USING SAME

This application claims benefit of provisional application Ser. No. 60/731,879, filed Oct. 31, 2005, the entire disclosure of which is expressly incorporated by reference herein.

TECHNICAL FIELD

The invention pertains generally to medical treatment and, more specifically, to apparatus, methods, and systems for providing brachytherapy to a human or other mammalian body.

BACKGROUND

Brachytherapy is a type of radiation therapy used to treat malignant tumors such as cancer of the breast or prostate. In general, brachytherapy involves the positioning of a radiation source directly into target tissue, which may typically include the tumor and/or surrounding tissue that may contain potentially cancerous cells (such as a cavity or void created by removal of the tumor).

Brachytherapy is often divided into two categories: high dose rate (HDR); and low dose rate (LDR). In HDR brachytherapy, a high activity radiation source is placed into the target tissue, often via a previously implanted catheter, for a short period of time, e.g., seconds to a few minutes. In contrast, LDR brachytherapy places a low activity radiation source into the target tissue for a longer—sometimes indefinite—period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to the target tissue, e.g., the tumor, gland, or other surrounding tissue. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which can result in less damage of normal tissue during treatment. Moreover, for patients, the relatively longer implantation period associated with LDR brachytherapy may result in fewer visits to a healthcare facility over the course of radiation treatment, as compared to HDR brachytherapy where patients return to the healthcare facility for each fraction of radiation delivered (typically 8-10 fractions for breast brachytherapy).

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they are, in common applications (e.g., prostate brachytherapy), provided in a standardized size of cylindrically shaped capsules that are approximately the size of a grain of rice, e.g., about 0.8 millimeters (mm) in diameter and about 4.5 mm in length, and are often referred to as "seeds."

LDR seeds are often delivered through needles using a guide template. The guide template may include a matrix of holes that guide the longitudinal advancement of the needles to insure their proper position relative to the target tissue. Once the needles are properly located in the target tissue, the seeds may be deposited along the longitudinal axis of each needle, after which the needles may be withdrawn.

While effective, current brachytherapy implementations have potential drawbacks. For example, the LDR seeds are typically left indwelling and free floating within the target tissue and are, therefore, susceptible to migration. Moreover, once implanted, LDR seeds are generally not considered to be removable or repositionable. LDR brachytherapy may also require careful dose distribution calculations and seed mapping prior to, and often during, seed implantation. Such calculation and mapping allows effective radiation delivery to the target tissue volume, while minimizing radiation to surrounding healthy tissue (the urethra and rectum, for example, in prostate brachytherapy). Yet, while such dose calculation and seed mapping techniques are effective, problems —such as potentially significant variability in accuracy of seed placement among different clinicians—may exist.

Yet another issue with conventional LDR brachytherapy techniques is that many of these techniques often require the radioactive seeds to be manipulated individually at the time of implantation, an often time-consuming process. Moreover, conventional LDR delivery needles are generally limited to delivering the seeds linearly (along a relatively straight line). Thus, to achieve the desired therapy profile, numerous implants (e.g., about 50-100 seeds are common with prostate brachytherapy), in conjunction with potentially complex dose distribution and mapping techniques and equipment, are often required.

SUMMARY

The present invention is broadly directed to apparatus and methods for delivering brachytherapy to a localized target tissue region. While the invention is useful in treating most any area of the body, it offers particular advantages in the treatment of breast tissue, e.g., breast tumors or lumpectomy cavities. For example, the apparatus, systems, and methods described herein may be used to place and remove a localized radiation source for both neoadjuvant and post-excisional treatment.

Exemplary embodiments are directed to brachytherapy devices and apparatus. Such devices and apparatus are capable of delivering brachytherapy treatment to a target region (e.g., breast tissue region). Other embodiments are directed to delivering multiple brachytherapy devices, either simultaneously or serially, to the target region. Systems and methods for delivering brachytherapy to the target region are also provided.

The above summary is not intended to describe each embodiment or every implementation of the present invention. Rather, a more complete understanding will become apparent and appreciated by reference to the following detailed description and claims in view of the accompanying drawings.

BRIEF DESCRIPTION OF THE VIEWS OF THE DRAWINGS

The present invention will be further described with reference to the drawings, wherein:

FIG. 1B illustrates an exemplary brachytherapy apparatus or kit in accordance with another embodiment;

FIGS. 2G-2L are diagrammatic illustrations of a method of using the brachytherapy apparatus of FIG. 1B, or other exemplary brachytherapy device;

FIGS. 3A-3B are enlarged partial views of a brachytherapy device in accordance with another embodiment;

FIGS. 4A-4B are enlarged partial views of a brachytherapy device in accordance with still another embodiment;

FIGS. 5A-5B are enlarged partial views of a brachytherapy device in accordance with yet another embodiment;

FIG. 5C is a view of the brachytherapy device of FIGS. 5A-5B illustrating an exemplary removal method;

FIGS. 5F-5G are enlarged views of a brachytherapy device in accordance with still another embodiment, wherein FIG. 5G is a section view taken along line 5G-5G of FIG. 5F;

FIGS. 5H-5J are enlarged views of a brachytherapy device in accordance with yet another embodiment, wherein: FIG. 5H is a side view of the device as assembled; FIG. 5I is a cross-sectional view of the device; and FIG. 5J is a view of the device with an outer portion removed;

FIGS. 6A-6D illustrate a brachytherapy device in accordance with still yet another embodiment, wherein: FIG. 6A is a view of the device as partially assembled; FIG. 6B is an exploded view; FIG. 6C is an enlarged partially assembled view; and FIG. 6D is an enlarged partial view;

FIGS. 6E-6H illustrate a brachytherapy apparatus or kit in accordance with another embodiment, wherein: FIG. 6E is an exploded view of components of the apparatus; FIG. 6F is an exploded view of a brachytherapy device of the apparatus of FIG. 6E; and FIGS. 6G and 6H are enlarged section views of portions of the apparatus;

FIGS. 6I and 6J illustrate a brachytherapy apparatus or kit in accordance with yet another embodiment, wherein: FIG. 6I illustrates a section view of the apparatus; and FIG. 6J is an enlarged section view of a distal end of the apparatus;

FIG. 7B illustrates the brachytherapy apparatus of FIG. 7A as it may be partially assembled;

FIGS. 8A-8E are diagrammatic illustrations of a method of using the brachytherapy apparatus of FIGS. 7A and 7B;

FIGS. 9A-9B are enlarged partial views of a brachytherapy device in accordance with another embodiment;

FIGS. 10A-10B are enlarged partial views of a brachytherapy device in accordance with yet another embodiment;

FIGS. 11A-11B are enlarged partial views of a brachytherapy device in accordance with still yet another embodiment;

FIGS. 12A-12B are enlarged partial views of a brachytherapy device in accordance with still another embodiment;

FIGS. 13A-13B are enlarged partial views of a brachytherapy device in accordance with yet another embodiment;

FIGS. 14A-14B are enlarged partial views of a brachytherapy device in accordance with still yet another embodiment;

FIG. 15 is a diagrammatic view of a brachytherapy apparatus in accordance with another embodiment;

FIGS. 16A-16G are diagrammatic illustrations of non-linear brachytherapy apparatus and methods in accordance with various embodiments, wherein: FIGS. 16A-16E illustrate a dual, off-axis catheter assembly; and FIGS. 16F-16G illustrate a spiral-shaped catheter;

FIGS. 17A-17B illustrate a brachytherapy apparatus in accordance with yet another embodiment;

FIG. 28B-28D illustrate a delivery or implantation system in accordance with still yet another embodiment, the system for use with brachytherapy apparatus and methods described herein, wherein: FIG. 28B is a diagrammatic perspective view; FIG. 28C is a partial perspective view illustrating a series of needles in place; and FIG. 28D is a perspective view illustrating coupling of a needle guide to the system; and FIGS. 29-31 illustrate an anchoring tab in accordance with one embodiment, the tab for use with a delivery system, e.g., the delivery systems of FIGS. 28A and 28B, wherein: FIG. 29 is a plan view of the tab; FIG. 30 is a view illustrating the tab in place; and FIG. 31 is an enlarged view of a portion of the tab.

DETAILED DESCRIPTION OF EXEMPLARY EMBODIMENTS

Figure 1A:
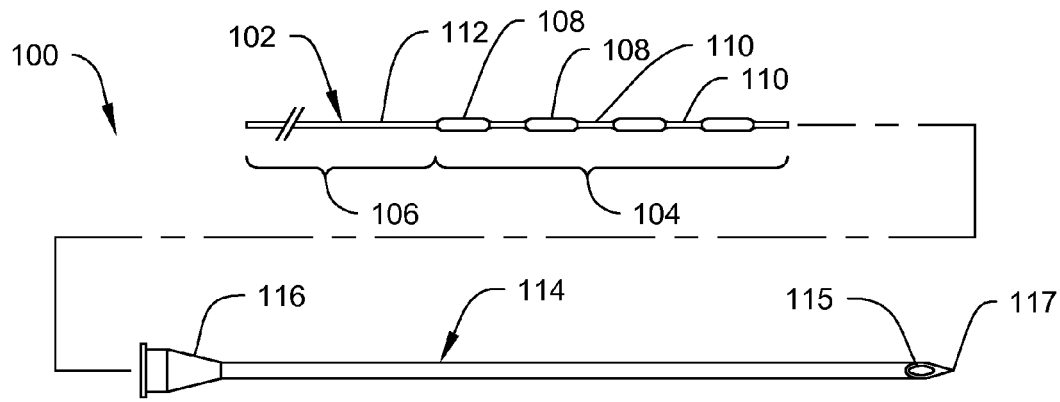
FIG. 1A illustrates an exemplary brachytherapy apparatus or kit in accordance with one embodiment.

In the following detailed description of exemplary embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention. For example, additional information regarding apparatus and methods that may be used in accordance with the embodiments described herein may be found in co-pending application Ser. No. 10/658,518, filed 9 Sep. 2003, the entire disclosure of which is expressly incorporated by reference herein.

Generally speaking, the present invention is directed to brachytherapy apparatus and methods. More particularly, the present invention provides a system for delivering one or more therapeutic elements (e.g., radiation sources) relative to a target tissue region. Once delivered, the radiation sources may be either immediately withdrawn (e.g., in HDR applications), or left in place, e.g., implanted, for a defined period (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. Unlike conventional LDR brachytherapy, apparatus and methods described herein provide not only indwelling therapy using pre-arranged packages of radioactive sources, e.g., seeds, but also allow easy removal of the radiation sources at the completion of brachytherapy.

As used herein, "radiation source" and "radioactive source" may include most any therapeutic element operable to deliver a dose of radiation. For example, the radiation source may be a radioactive seed or, alternatively, a LDR or HDR wire element (e.g., Iridium wire).

The term "implantable," as used herein, indicates the capability of a device to be inserted into the body and then maintained in a fixed or static position, relative to the immediately surrounding tissue, for an extended period of time, e.g., an hour or more and, more optionally, several hours or more, including several days or more.

Furthermore, "target tissue," "target tissue region," "target region," and "target tissue volume," as used herein, may include most any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that, while described herein primarily with respect to LDR brachytherapy, the apparatus and methods described herein may also have application to HDR brachytherapy (e.g., HDR catheters) as further described below. Moreover, while described herein with respect to brachytherapy, the apparatus and methods described herein may also be used for other therapy regimens that benefit from the removable implantation of therapy-delivering elements.

For the sake of brevity, embodiments are described herein as relating to the treatment of breast cancer. However, this particular application is not limiting. That is, those of skill in the art will readily appreciate that the systems, apparatus, and methods described herein may find application to most any cancer that may receive benefit from brachytherapy.

With this introduction, turning to the drawings, FIG. 1A illustrates an exemplary kit or apparatus 100 for providing brachytherapy to a target tissue region of a body. The apparatus 100 may include an elongate and flexible, removably implantable brachytherapy treatment device 102 (also referred to hereinafter as "brachytherapy device 102") having a therapy delivery portion 104, and an elongate and flexible tail portion 106. The tail portion 106 may, as further described below, provide the ability to remove the device 102 at therapy completion. Other components described below, e.g., locking members, may also be included with the apparatus 100.

The term "flexible" is used herein to describe a component that is highly pliant, e.g., a component that may be substantially and easily bent, flexed, and/or twisted without experiencing breakage or permanent deformation.

The therapy delivery portion 104 may form a carrier pod of therapeutic elements, e.g., radiation sources such as radioactive seeds 108, secured relative to one another and to the therapy delivery portion 104. One or more spacers 110 may optionally be located between each seed 108 to obtain the desired seed separation.

The seeds 108 may be produced from most any acceptable radioactive source now known (e.g., radioactive Palladium, Iodine, Cesium, or Iridium) or later developed. Typically, numerous seeds 108 are provided and precisely placed along the length of the therapy delivery portion 104 in order to correspond to the desired therapy delivery regimen. While the radioactive sources are described herein as seeds 108, they may take other forms such as a continuous filament (or numerous discontinuous segments) of radioactive wire (e.g., Iridium wire).

In some embodiments, the brachytherapy device 102 may include a flexible casing or casing member, illustrated in the figures as tube or tube member 112, in which the seeds 108 and optional spacers 110 are securely retained. In some embodiments, the casing is made from a non-dissolving and flexible, heat-shrinkable tubing material. "Heat-shrinkable tubing," as used herein, refers to tubing, such as various plastic tubing, in which subsequent thermal exposure causes the tubing to shrink, thereby allowing it to securely retain the seeds 108 in place. Exemplary heat-shrinkable materials include polyester, fluorinated polymers, and polyolefins.

While most any number of tubing sizes is contemplated, in one embodiment, the tube 112 may have an initial inside diameter of about one millimeter (1 mm) and a wall thickness of about 0.05 mm. Once heated, the tube 112 may shrink (if unconstrained) to an outer diameter ranging from about 0.3 mm to about 0.6 mm.

While the casing is described herein generally as tube-shaped, the casing may, in other embodiments, be most any shape that is capable of effectively securing the individual seeds 108 relative to the casing and to one another.

Once the seeds 108 and optional spacers 110 are located within the tube 112, the tube may be shrunk by exposure to heat, thus contracting the tube 112 around the seeds 108. The tail portion 106 may be formed by an integral portion, e.g., extension, of the casing (tube 112) that extends beyond the seeds 108. To reduce the diameter of the tail portion 106, it may also be thermally treated (shrunk). Other embodiments (described below) may utilize a two-part brachytherapy device, e.g., a separate filament tail portion attached to the therapy delivery portion.

Regardless of the specific configuration, the brachytherapy devices 102 described herein provide not only proper spacing of the seeds 108, but also facilitate subsequent seed identification and removal. Moreover, because the seeds are contained within the pod defined by the therapy delivery portion 104, seeds may not require individual handling, thus simplifying inventory and handling prior to, and at the time of, implantation.

The components of the device 102, including the casing (tube 112) and tail portion 106, may be constructed of non-dissolving materials. The term "non-dissolving" is used herein to indicate most any material that does not substantially deteriorate or otherwise break down during the implantation period.

The brachytherapy apparatus 100 may also include a catheter, e.g., needle 114. While illustrated as needle 114, any other type of catheter, such as the cannulae described further below, may also be used. The needle 114 defines a lumen 115 of sufficient size to allow the therapy device 102 to pass through as indicated in FIG. 1A. The needle 114, in some embodiments, may further include a hub 116 at a proximal end to assist with manipulation of the needle and insertion of the therapy device 102. A distal end of the needle 114 may form a sharpened tip 117 operable to pierce the body as further described below. The needle 114 may be made from most any suitable biocompatible material. For example, it may be made from metal, e.g., stainless steel, titanium, or nickel titanium alloy. It may also include a removable outer sheath (not shown) made of plastic, e.g., fluorinated polymers.

FIGS. 2A-2E illustrate an exemplary method of using the brachytherapy apparatus 100 of FIG. 1A. Once a target tissue region 202 (a tumor or tumor cavity) within body 200 is accurately located, the needle 114 may be inserted into the body 200, as shown by arrow 203 in FIG. 2A, to a predetermined depth. The relative location(s) of the needle 114 and/or the target tissue region 202 may be determined by most any method, e.g., via ultrasound, CT scan, stereotactic X-ray, etc. The needle 114 may further be aligned with the use of a needle guiding template as further described below, or by other techniques.

Figure 2A:
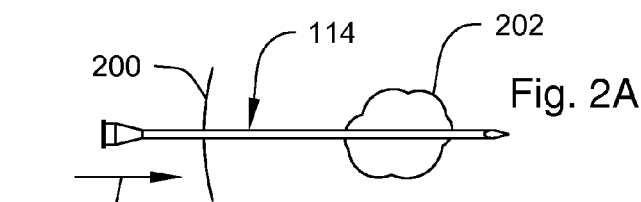
FIGS. 2A-2E are diagrammatic illustrations of a method of using the brachytherapy apparatus of FIG. 1A.
Figure 2B:
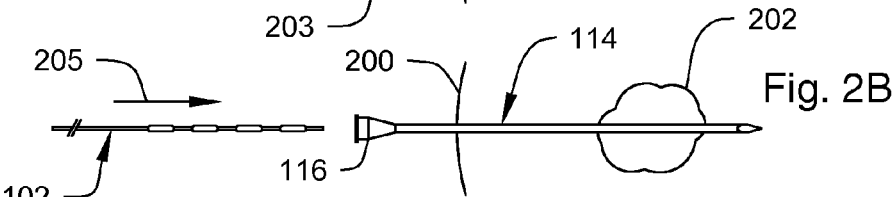
Figure 2C:
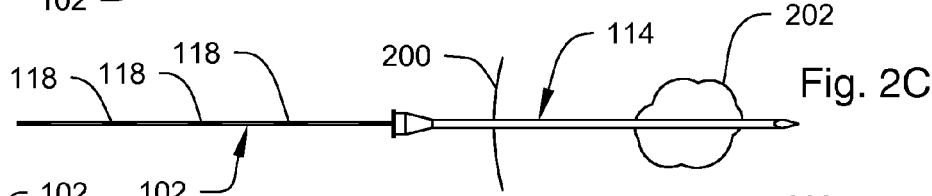

Next, the brachytherapy device 102 may be inserted into the lumen 115 of the needle 114, as shown by arrow 205 in FIG. 2B, until the therapy delivery portion 104 is located at the desired depth relative to the target tissue region 202 as shown in FIG. 2C. To assist in determining the approximate insertion depth of the therapy device 102, the tail portion 106 may include measurement demarcations 118. Other location verification techniques, e.g., X-ray, ultrasound, etc., may also be used.

Figure 2D:
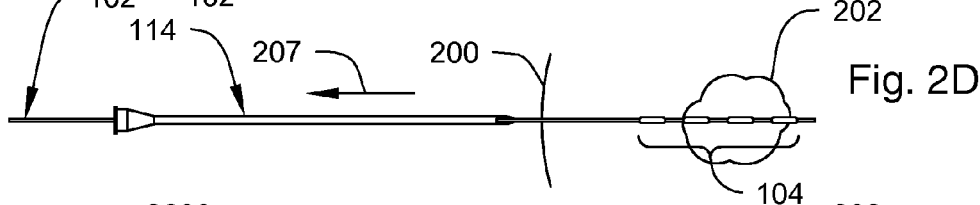
Figure 2E:
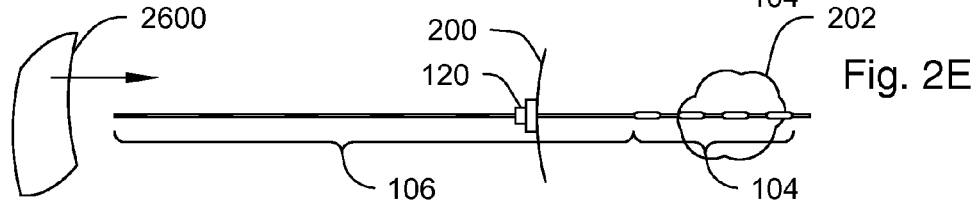

Once the therapy device 102 is located at the desired depth, the needle 114 may be withdrawn from the body in the direction 207 as shown in FIG. 2D, leaving the therapy delivery portion 104 of the device 102 at the desired position within the body 200. The tail portion 106 may have sufficient length such that it extends outside of the body 200 as shown in FIG. 2E. That is, the tail portion 106 may extend externally through a puncture made by the needle 114.

Figure 27:
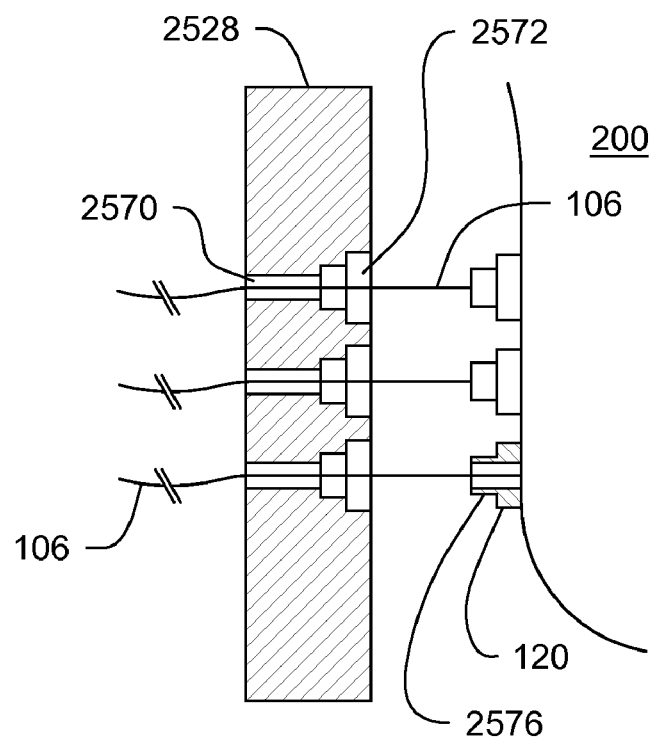
FIG. 27 is a cross-section of a portion of the delivery system of FIGS. 25A-25D.

In order to prevent migration of the therapy delivery portion 104, a locking member 120 may be crimped or otherwise attached to the tail portion 106 of the therapy delivery device 102 immediately adjacent the associated puncture in the body 200. The locking member 120 may assist in maintaining the location of the therapy delivery portion 104 relative to the target tissue region 202. While most any locking member may be used, one embodiment utilizes a malleable, hat- or U-shaped lock that can be easily and securely crimped to the tail portion with, for example, a surgical clip applier or similar tool. An enlarged view of an exemplary locking member is illustrated in FIG. 27.

For illustration purposes, only a single therapy delivery device 102 is shown in FIGS. 2A-2E. However, in practice, multiple devices would be utilized to provide adequate dosage to the target tissue region 202. The actual number of devices 102 may vary depending on various parameters such as lesion size, radiation source activity levels, and proximity to other organs/vulnerable tissue (e.g., skin, chest wall). However, quantities ranging from about 5 to about 25 devices are contemplated.

Figure 2F:
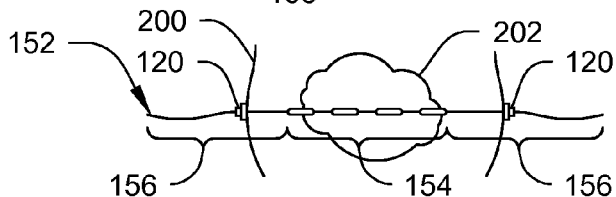
FIG. 2F is a diagrammatic illustration of another brachytherapy apparatus.

FIG. 2F illustrates a variation of the therapy device 102 of FIGS. 2A-2E that may offer additional benefits, especially to the treatment of breast cancers. In this embodiment, a therapy device 152 similar in most respects to the device 102 is provided. However, the device 152 may include both a first tail portion extending from a first end of a therapy delivery portion 154 and a second tail portion extending from a second end, i.e., it may include a tail portion 156 at each end of the therapy delivery portion 154. During implantation, the needle 114 may pass completely through the body, e.g., breast 200, such that one tail portion 156 extends out the opposite side of the breast 200. In this way, locking members 120 may be secured at two locations relative to the target tissue region 202, thus preventing or substantially limiting movement of the therapy delivery portion 154 relative to the target tissue region 202.

Unlike conventional brachytherapy catheters, which may be two millimeters (2 mm) or more in diameter, the devices described herein, e.g., devices 102, may be about one millimeter (1 mm) or less in diameter at the therapy delivery portion 104 and even smaller at the tail portion 106. This construction permits the devices 102 to be relatively small and flexible, and thus less obtrusive to the patient. In fact, the size and flexibility of the tail portions 106 may be similar to that of a conventional suture. As a result, securing the tail portions 106 may be accomplished in any number of ways including, for example, folding the tail portions against the contour of the surrounding body and fixing them such as by tying the ends and/or securing the ends with adhesive, the latter represented by bandage 2600 in FIGS. 2E and 26.

FIG. 1B illustrates another kit or apparatus 560 for providing brachytherapy to a target tissue region of the body. The apparatus 560 may include an elongate and flexible, removably implantable, brachytherapy treatment device 562 ("brachytherapy device 562") having a therapy delivery portion 564, and at least one elongate and flexible tail portion 566. The tail portion(s) 566 may, as further described herein, provide for removal of the device 562 at therapy completion. Other components described below, e.g., locking members, may also be included with the apparatus 560.

As with the device 102, the therapy delivery portion 564 may form a carrier pod of therapeutic elements, e.g., one or more radioactive sources such as radioactive seeds 108, secured relative to one another. Spacers 110 may optionally be located between each seed 108 to obtain the desired seed separation. The brachytherapy device 562 may also include a casing, e.g., heat-shrinkable tube or tube member 112, in which the seeds 108 and optional spacers 110 are securely retained. In the embodiment illustrated in FIG. 1B, the device 562 may optionally include alert markings (e.g., segments or markings 565) that indicate an outermost boundary of the radioactive source, e.g., outermost seed 108, as further described below. The device 562 may, in some embodiments, also include positioning indicia, e.g., repeating linear markings 559, along the tail portion 566 to indicate implantation depth. These linear markings may be circumferential bands of ink or other identifiable marks (e.g., foil, laser markings). The markings may also be visible under X-ray (e.g., tantalum-impregnated paint, gold bands, etc.). The markings may be placed directly on the surface of the tail, or beneath the tail surface, such as on the surface of an inner filament that resides within the tube 112 (see, e.g., filament 573 described below with respect to device 572 of FIG. 5E).

The brachytherapy apparatus 560 may also include a catheter, e.g., needle 114' similar in many respects to the needle 114 of FIG. 1A. The needle 114' defines a lumen 115' of sufficient size to allow the device 562 to pass through as indicated in FIG. 1B. The needle 114', in some embodiments, may further include a hub 116' at a proximal end (although, as described below, such hubs may be optional). Unlike the needle 114, the distal end of the needle 114' may form a canoe-shaped ("huber") tip. This tip shape may reduce tissue coring when the needle 114' pierces the body.

FIGS. 2G-2L illustrate an exemplary method of using the brachytherapy apparatus 560 of FIG. 1B. While illustrated with only one needle 114', it is to be understood that the described method could be utilized to simultaneously or sequentially insert an array of needles as will be further described below. Moreover, while shown in conjunction with the brachytherapy device 562, other devices as described and illustrated herein could certainly be substituted for the device 562.

Prior to needle 114' insertion, the brachytherapy device 562 may be coupled to the needle 114', e.g., preloaded within the lumen 115'. Once the target region 202 (a tumor or lumpectomy cavity region within the breast 200) is accurately located, the apparatus 560, e.g., the needle 114' with the brachytherapy device 562 contained therein, may be inserted into a proximal side of the breast as shown by arrow 561 in FIG. 2G. The needle 114' may be inserted to a predetermined depth (as the needle 114 of FIGS. 2A-2E), or may be inserted completely through the breast 200 as shown in the FIGS. (see, e.g., arrow 563 in FIG. 2H). The relative location(s) of the needle 114' and/or the target region 202 may be determined by any acceptable method, e.g., via ultrasound, CT scan, stereotactic X-ray, etc. The needle 114' may further be aligned with the use of a needle guiding template as further described below, or by other guidance techniques.

Once the needle 114' passes through a distal side of the breast 200 as shown in FIG. 2H, the distal tail portion 566 of the brachytherapy device 562 may be extended through the distal end of the lumen 115' of the needle by pushing a proximal tail portion 566 as represented by arrow 567 in FIG. 2I. The physician may then grasp or otherwise immobilize the distal tail portion 566 and withdraw the needle 114' in the direction 568 as shown in FIG. 2J, leaving the therapy delivery device 562 implanted in the breast 200 as shown in FIG. 2K.

The physician may further manipulate the proximal and distal tail portions 566 of the device 562, as represented by arrows 569 in FIG. 2K, to achieve the desired positioning of the therapy delivery portion 564 relative to the target region 202. The alert markings 565 may assist in visualizing and/or locating (e.g., via X-ray or CT scan) the therapy delivery portion 564 during positioning. The positioning indicia (e.g., the repeating linear markings 559) may also be used to indicate the location of the therapy delivery portion 564 relative to the skin surface.

In order to prevent migration of the therapy delivery portion 564, a locking member 570 may be placed over each tail portion 566 of the therapy delivery device 562 immediately adjacent the associated puncture in the breast 200. The locking member 570 may assist in securing and maintaining the location of the therapy delivery portion 564 relative to the target tissue region 202. While most any locking member configuration may be used, one embodiment utilizes a malleable, hat- or U-shaped grommet that can engage the tail portion 566 via friction or crimping and hold the device 562 in place. Similarly, a button (not shown) with a through hole may also be used. A secondary clamp, e.g., a surgical clip 571, may be securely crimped to the tail portion immediately adjacent and outboard of the locking member 570 (with, for example, a surgical clip applier or similar tool) to more permanently secure the device 562 in place.

Once again, only a single therapy delivery device 562 is illustrated in FIGS. 2G-2L. However, in practice, multiple devices could be utilized to provide the desired therapy dosage to the target tissue region 202. Systems and methods utilizing such multiple implants are described in more detail below.

Figure 1C:
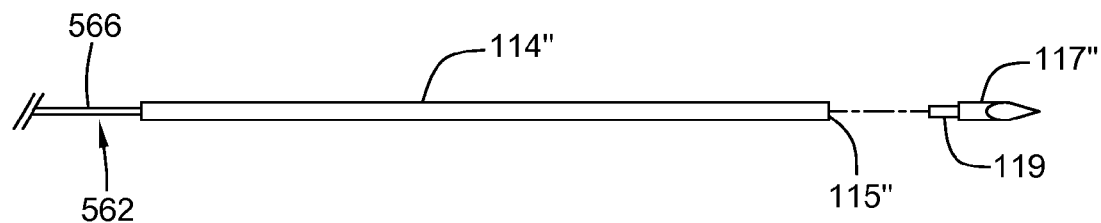
FIG. 1C illustrates an alternative embodiment of a needle for use with the apparatus or kits illustrated in FIGS. 1A and 1B.

FIG. 1C illustrates a needle 114" that may be substituted for either of the needles 114 or 114' described above. The needle 114" is similar in most respects to the needles 114 and 114' with the exception that its distal end includes a removable sharp tip 117". The tip 117" may include a stepped portion 119 (e.g., a portion of reduced diameter) that is selectively received within the lumen 115" of the needle 114". As shown, the stepped portion 119 of the tip 117" may be received within the lumen 115" with a slight interference fit to ensure that the tip remains in place during needle insertion. The outer diameter of the tip 117" is substantially the same as the outer diameter of the needle 114" to reduce any discontinuity in the needle profile. The needle 114" provides a solid pyramidal tip that may substantially eliminate tissue coring and minimizes wandering, but that is removable to permit advancement of brachytherapy devices, e.g., device 562, from the distal end of the needle.

During use, the tip 117" may be coupled to the needle 114" and the needle assembled and advanced through the tissue in a manner similar to that illustrated in FIG. 2G. Once the needle 114" emerges from the distal side of the breast as shown in FIG. 2H, the distal tip 117" may be removed from the needle and the distal tail portion 566 of the device 562 advanced through as shown in FIG. 2I. Withdrawal of the needle and positioning/securing of the device 562 may be accomplished in accordance with the methods already described herein.

While illustrated as hubless in FIG. 1C, alternative embodiments of the needle may include a hub similar to the hub 116 and 116' of FIGS. 1A and 1B, respectively.

FIG. 3A is an enlarged view of the therapy device 102 of FIG. 1A. As clearly illustrated in this view, the therapy device 102 may include the therapy delivery portion 104 and the tail portion 106. As described above, the therapy delivery portion 104 may include one or more radioactive seeds 108 separated by spacers 110 and encased within the casing, e.g., heat-shrinkable tube 112. The tail portion 106 may be formed by the portion of the tube 112 that does not surround the seeds 108. In some embodiments, the conformal properties of the tube 112 may be sufficient to ensure proper seed spacing, thus negating the need for spacers 110. FIG. 3B illustrates a section view through a seed 108 and the tube 112 taken along line 3B-3B of FIG. 3A.

FIGS. 4A-4B illustrate a therapy device 402 in accordance with another embodiment. The device 402 is similar in many respects to the device 102 described above. For example, the device 402 may include a therapy delivery portion 404 and a tail portion 406 as illustrated in FIG. 4A. A casing, e.g., heat shrinkable tube 412, may be used to encase the seeds 108 and optional spacers 110 as well as to form the tail portion 406. However, unlike the embodiment of FIGS. 3A-3B, the tube 412 may include a radioabsorptive portion 414, e.g., a substance or liner, positioned along a portion of the circumference of the therapy delivery portion 404 (see FIG. 4B). The radioabsorptive portion 414 may include a radiation attenuating material, and thus reduce radiation exposure to tissue blocked by the radioabsorptive portion 414 as opposed to tissue not blocked by the portion 414. While not limited to any particular embodiment, the radioabsorptive portion may be formed by a substance (e.g., Tungsten, Nickel-Titanium alloy, stainless steel) applied to, or impregnated within, a portion of the tube 412. Alternatively, the radioabsorptive portion(s) may be formed by a liner within, or secured to a portion of, the tube 412. FIG. 4B illustrates a section view through a seed 108 and the tube 412 taken along line 4B-4B of FIG. 4A.

The term "radiotransparent" is used herein to indicate only that the identified portion of the apparatus or device is relatively more transparent to radiation than the portion identified as "radioabsorptive."

FIGS. 5A-5B illustrate a therapy device 502 in accordance with yet another embodiment. The device 502 is similar in many respects to the device 102 described above. For example, the device 502 may include a therapy delivery portion 504 and a tail portion 506 as shown in FIG. 5A. A casing, e.g., heat shrinkable tube 512, may be used to encase the seeds 108 and optional spacers 110 as well as to form the tail portion 506. However, unlike the previous embodiments, the therapy device 502 may incorporate an anchor member, e.g., a flat or round cross-section anchor wire 514, which extends along at least a part of the therapy delivery portion 504. The anchor wire 514 protrudes from one or both ends of the therapy delivery portion and may be bent to form one or more hooks or anchors 516.

When the therapy delivery portion 504 exits the needle 114 (see FIG. 1A) during implantation, the anchors 516 may extend and engage surrounding tissue, thereby assisting in preventing migration of the therapy device 502. While only a single anchor is shown at each end of the therapy delivery portion 504, other embodiments may include multiple anchors at one or both ends to further resist movement, e.g., rotating or twisting. FIG. 5B illustrates a section view through a seed 108 and the tube 512 taken along line 5B-5B of FIG. 5A.

After the desired dose of radiation has been delivered, the therapy device 102 (or any of the other therapy devices described herein, e.g., devices 402 or 502), may be removed in any number of ways. For example, the device 102 may be removed by first removing any dressing (e.g., bandage 2600 of FIG. 2E) and locking member(s) 120, and then simply applying a pulling force to one of the tail portions 106 that extends outside of the body 200. Alternatively, the devices 102 may be removed prior to or during excisional surgery of the tumor 202 via known methods, e.g., via methods similar to excision utilizing localization wires.

Where the therapy device 102 includes internal retaining elements, e.g., anchors 516 of device 502 (FIG. 5A), a removal catheter 550 as shown in FIG. 5C may be used. The removal catheter 550 is similar in most respects to the delivery cannulae and needles described herein, e.g., needle 114. The catheter 550 may be threaded over the tail portion 106 and advanced until it encompasses the therapy delivery portion 104. For example, the removal catheter 550 may be advanced until its distal end engages the distal retaining element(s), e.g., distal anchor 516 of FIG. 5A. Further advancement of the removal catheter 550 may bend the anchor sufficiently to permit the therapy delivery portion to slide into the removal catheter as shown in the broken line representation of FIG. 5C. The device 502 and the removal catheter 550 may then be withdrawn as a unit from the body.

Figure 5D:
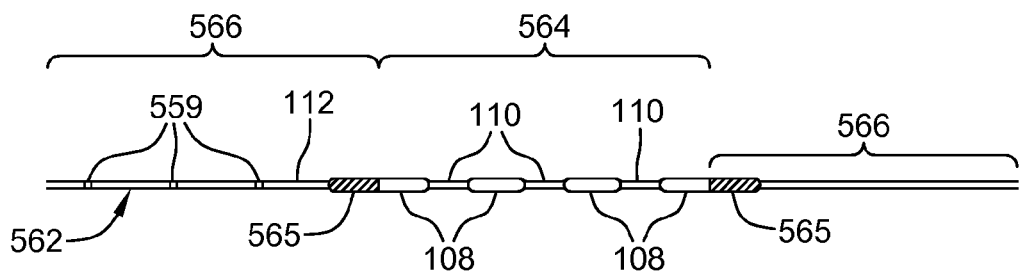
FIG. 5D is an enlarged view of the brachytherapy device illustrated in FIG. 1B.

FIG. 5D is an enlarged view of the therapy device 562 shown in FIGS. 2G-2L. As clearly illustrated in this view, the therapy device 562 may include the therapy delivery portion 564 and the tail portions 566. As described above, the therapy delivery portion 564 may include one or more radioactive seeds 108 (e.g., low dose rate seeds) separated by optional spacers 110 and encased within the heat-shrinkable tubing 112. The tail portions 566 may be formed by extensions of the casing, e.g., the tubing 112.

As with the other devices described herein, the device 562 may utilize tubing 112 that is heat-shrinkable. As a result, the tubing 112 may frictionally engage the seeds 108 and spacers 110 and capture the same in place. In the illustrated embodiments, the tubing 112 may have an internal diameter at its first and second ends that is smaller than its internal diameter at an intermediate location (e.g., smaller than the internal diameter at a location between the first and second ends). Stated alternatively, the internal diameter of the tubing 112 at the first end and the second end may be less than the outer diameter of the seeds 108 and spacers 110. Accordingly, the tubing may physically capture and restrain the seeds and spacers.

As described above, the device 562 may further include indicia, e.g., alert markings 565, at or near the ends of the therapy delivery portion 564. The alert markings 565 may be located on either the tail portions or on the therapy delivery portion. In either case, the alert markings may be located immediately beyond an outermost portion of the radioactive sources, e.g., the outermost edge of the outermost seed 108. The markings 565 may improve visibility of the therapy delivery portion 564 during implantation (e.g., via CT or X-ray positioning methods). The alert markings 565 may be brightly colored or otherwise distinguishable from the remainder of the device 562. As a result, when the alert markings 565 are visible after implantation, it serves as an indication to the physician that the radioactive source is potentially too close to the skin surface. To avoid skin complications, the physician may then reposition the device 562 so that the alert markings 565, and thus the radioactive sources, thereby assuring a proper distance between the radioactive source and the skin surface. An acceptable distance between the end of the radioactive source and the skin surface may vary based on radioactivity of the source. However, distances of about 7 millimeters to about 12 millimeters may be common for low dose rate seeds.

The alert markings 565 may, in one embodiment, be formed by a component portion of the therapy delivery portion 564 or the tail portions 566. Alternatively, the markings 565 could be formed by physical markings on the tubing 112. Similarly, the repeating linear markings 559 may be physical markings placed directly on the tubing 112, or, as with the device 572 described below, may be formed on an elongate filament member 573 that extends through the tail portion.

In one embodiment, each seed 108 may have substantially the same radioactivity level as the other seeds within the device. However, as with the other embodiments described herein, brachytherapy may be modified by utilizing seeds that have differing levels of radioactivity within the same brachytherapy device. Stated another way, a first radioactive source (e.g., first seed) of the device may have a first radioactivity level (e.g., 5 millicuries (mCi)), while a second radioactive source (e.g., second seed) of the same device may have a second radioactivity level (e.g., 1 mCi) that is less than the first radioactivity level. Likewise, each seed within a given device could have the same radioactivity level, but different devices could contain seeds of different radioactive levels.

Figure 5E:
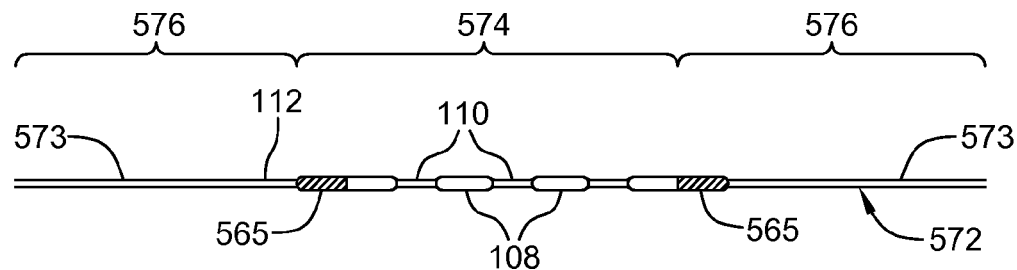
FIG. 5E is an enlarged view of a brachytherapy device in accordance with another embodiment.

FIG. 5E illustrates a therapy delivery device 572 in accordance with another embodiment. The device 572 is similar in most respects to the device 562, e.g., it includes tail portions 576 and a therapy delivery portion 574 having seeds 108 and optional spacer 110 surrounded by tubing 112. However, the tail portions 576 may further include the elongate filaments 573. The filaments 573 may extend from the therapy delivery portion 574 outwardly beyond the tubing 112. The filaments 573 may be used, for example, when a less compliant tail portion is desired, or when the tail portions 566 may be subject to pulling forces beyond the capability of the tubing 112.

Figure 5F:
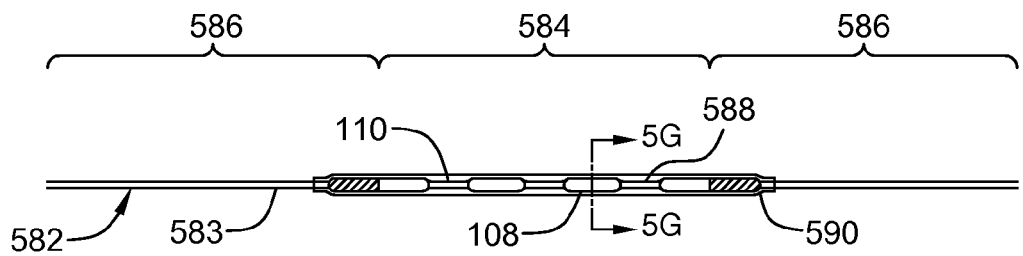
Figure 5G:
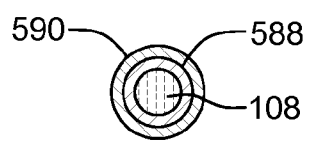

FIGS. 5F and 5G illustrate a therapy delivery device 582 in accordance with yet another embodiment. As with the other embodiments described herein, the therapy delivery device 582 may include a therapy delivery portion 584 and tail portions 586. The therapy delivery portion 584 may include radioactive seeds 108 separated by optional spacers 110 as already described herein.

However, unlike some of the other embodiments described above, the device 582 may further include, in place of the single segment of tubing 112, a first or inner layer 588 of material that surrounds most or all of the therapy delivery portion 584, and a second or outer layer 590 of material. The inner layer 588 may be configured as a meltable tubing segment that may be melted once in place. Exemplary materials for the inner layer 588 may include polyolefin, polyvinyl chloride, and nylon. The inner layer 588 may be melted either before or after the outer layer 590 (which could be the heat-shrinkable tubing 112 as already described herein) is placed over the therapy delivery portion 584. Exemplary materials for the outer layer 590 may include heat-shrinkable fluorinated ethylene propylene (FEP), polyethylene terephthalate (PET), Polytetrafluoroethylene (PTFE), and other non-bioabsorbable materials. In some embodiments, the outer layer 590 may be removed after the inner layer 588 is melted. FIG. 5G illustrates a section view taken along line 5G-5G of FIG. 5F. The tail portions 586 of the device 582 may include a filament 583 as illustrated in FIG. 5F and described above with respect to the device 572. In other embodiments, the outer layer 590 may extend outwardly to form the tail portions 586. In the case of the latter, the filaments 583 may be optional.

Figure 5H:
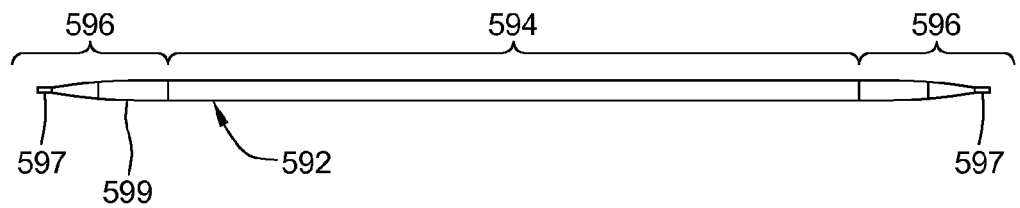
Figure 5I:
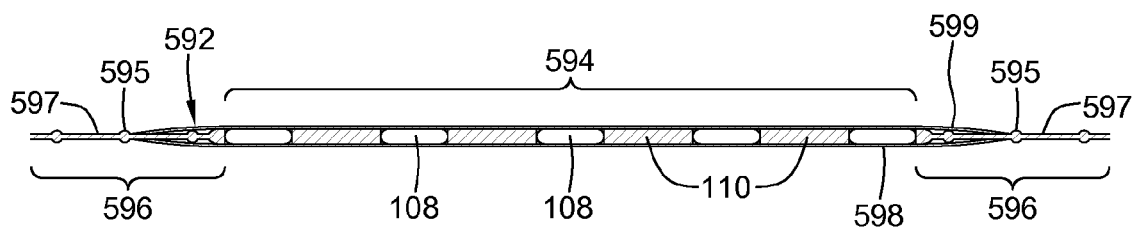

FIGS. 5H-5G illustrate a brachytherapy device 592 in accordance with yet another embodiment. As with other embodiments described herein, the therapy delivery device 592 may include a therapy delivery portion 594 and tail portions 596, wherein the latter are defined by filaments 597, as shown in FIG. 5I. The therapy delivery portion 594 may include the radioactive seeds 108 separated by optional spacers 110 as already described herein and illustrated in FIG. 5I.

Like the device 582 of FIGS. 5F and 5G, the device 592 may also include an inner layer 598 of material that surrounds most or all of the therapy delivery portion 594 (see FIGS. 5I and 5J), and an outer layer 599 that covers the inner layer (see FIG. 5H).

Figure 5J:
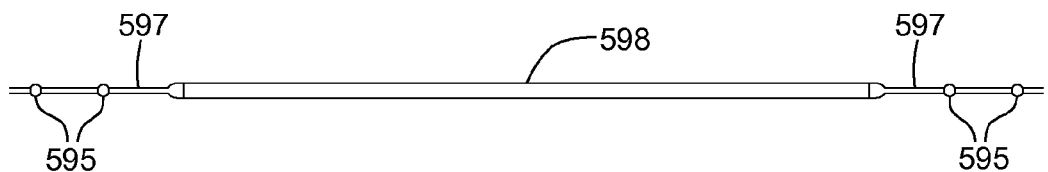

The inner layer 598 may be meltable to encapsulate the seeds 108, spacers 110, and ends of the filaments 597. In some embodiments, the inner layer 598 may include thermoformed ends to better capture the filament ends as shown in FIG. 5J. As with the device 582, the inner layer 598 may be polyolefin, nylon or a similar thermoplastic material. The outer layer 599, on the other hand, may be FEP, PET or PTFE shrinkable tubing. The thickness of the outer layer should be sufficient to provide adequate tensile strength, and sufficient bending stiffness to minimize the amount of bending within the tissue or cavity as the patient moves about during the implantation period. The outer layer 599 may provide a smooth outer surface that is advantageous during implantation/removal. It may also assist in securing the filaments 597 to the therapy delivery portion 594.

The filaments 597 may be made from most any flexible thermoplastic material including, for example polyolefin or nylon. In the illustrated embodiment, the filaments 597 may include spaced-apart anchoring ribs 595 that form knot-like protrusions along the filaments (areas of enlarged cross section relative to the remainder of the tail portion). The ribs 595 may be used in conjunctions with an anchoring tab as further described below.

In addition to the noted attributes, the dual encapsulation layer configurations described above (see e.g., FIGS. 5F-5J) may offer additional benefits. For example, each of the two materials (e.g., inner layer 598 and outer layer 599 in the device 592) may be selected to provide different degrees of flexibility/rigidity, as well as to maximize torsional (kinking) resistance of the device. An additional layer of heat-shrinkable tubing over a portion of the therapy delivery portion may also be provided to further modify flexibility.

Figure 6A:
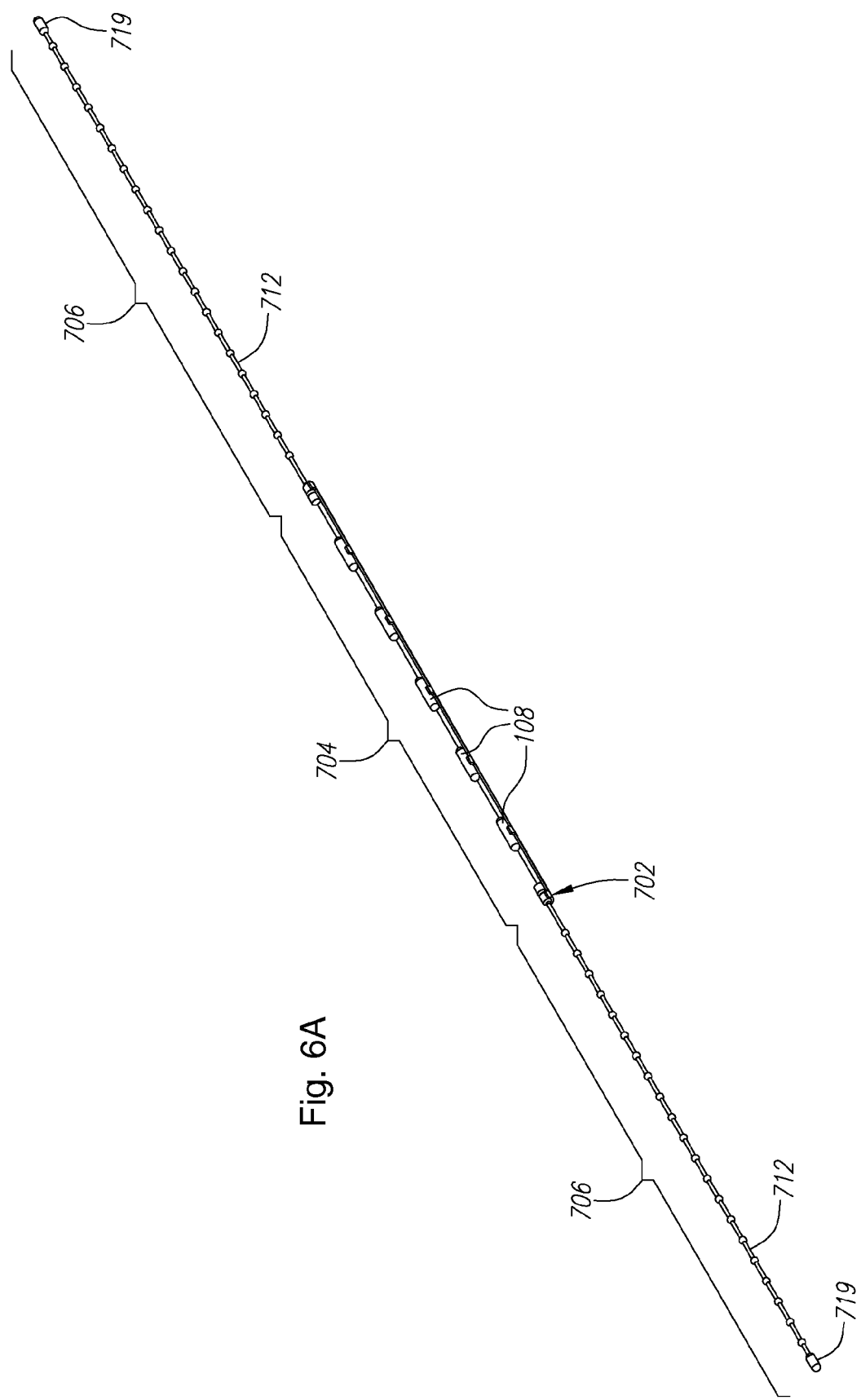
Figure 6B:
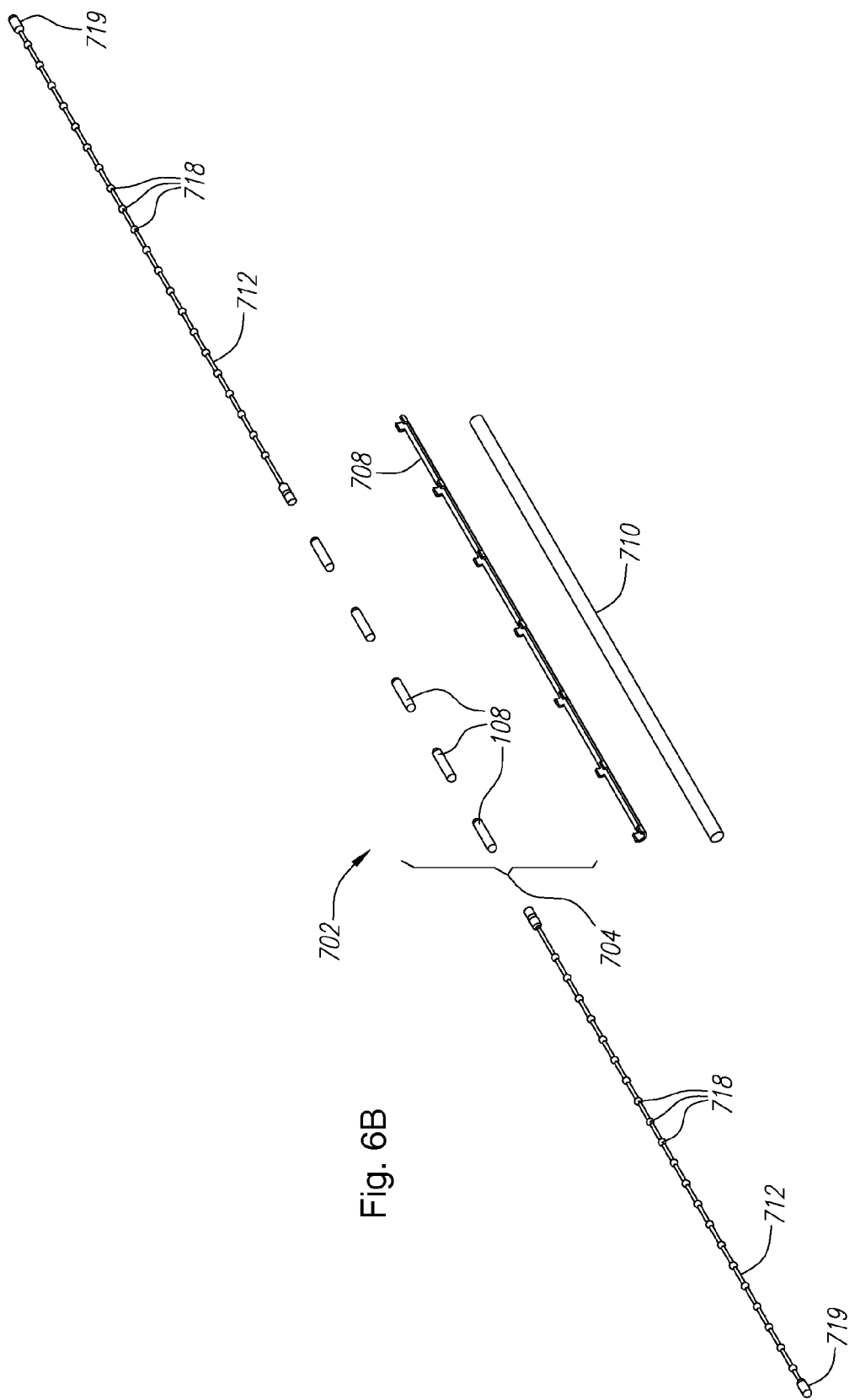
Figure 6C:
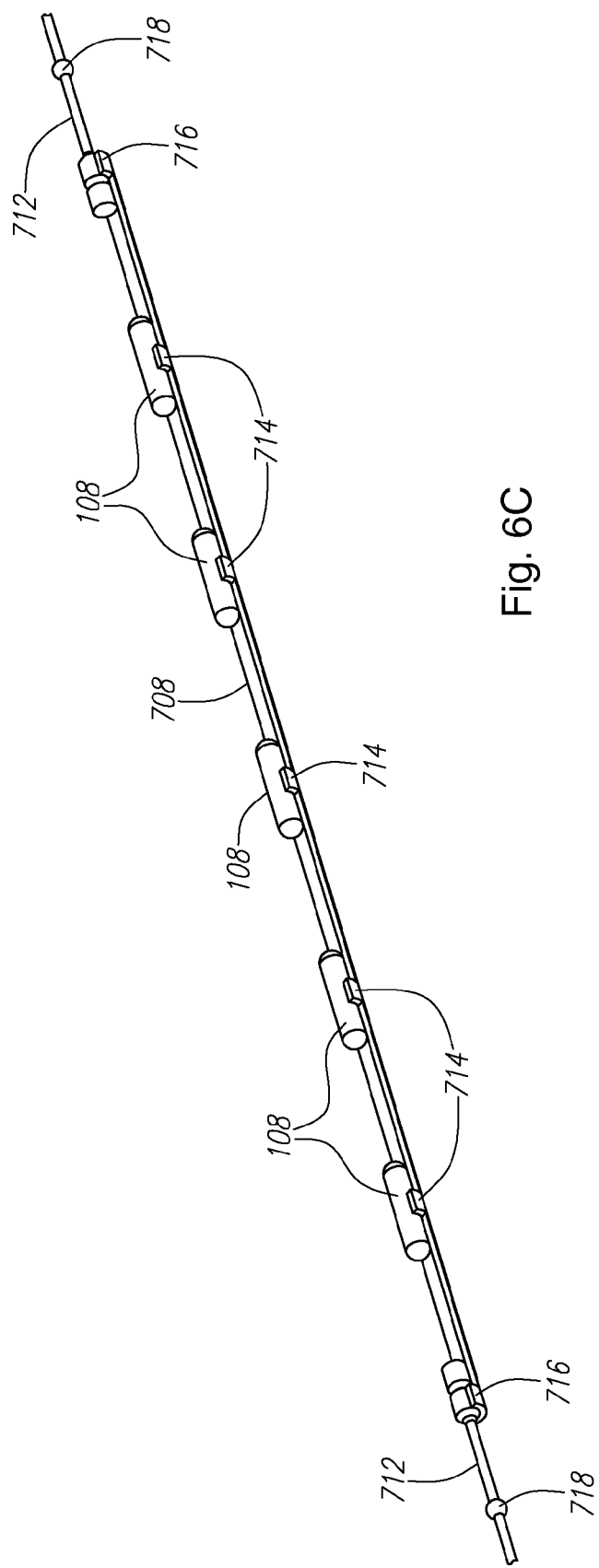

FIGS. 6A-6D illustrate a brachytherapy device 702 in accordance with yet another embodiment. The device 702 may, like the other embodiments described herein, include a therapy delivery portion 704 containing seeds 108, and tail portions 706 (see FIG. 6A). As shown exploded in FIG. 6B, the therapy delivery portion 704 may further include: a support member (e.g., tray 708) that supports the seeds 108; and tubing 710 that encases the seeds and the tray and, in some embodiments, portions of the tail portion. The tubing 710 may be heat-shrinkable tubing as already discussed herein (e.g., similar to the tubing 112). The tray 708 may be made of most any material including metal sheet (e.g., stainless steel, titanium) and plastic (polyester, PET). The tail portions 706 may again be formed by filaments 712 that attach to the therapy delivery portion, e.g., to the tray 708, as further described below. As with the filaments 597 described above, the filaments 712 may include anchoring ribs 718 that are best shown in FIG. 6C.

FIG. 6C is an enlarged view of the device 702 with the tubing 710 removed for clarity. In this view, the tray 708 is illustrated as having portions such as ears or tabs 714 capable of mechanically engaging and securing the seeds 108 in place (e.g., by crimping). In such a configuration, seed spacers (such as the spacers 110 illustrated in previous embodiments) may be unnecessary. The tray 708 may include other portions such as end tabs 716. The end tabs 716 may be used to mechanically engage and secure the tail portions, e.g., the filaments 712, to the tray 708. In one embodiment, the tray 708 may be photo-chemically etched and formed to yield the tabs 714 and 716.

The tray 708 may incorporate and retain most or all of the "loose" components of the device 702. The tray may further augment the overall structural integrity of the device 702, which may ease physician manipulation, especially during implantation, positioning, and removal from the body.

The device 702 may be implanted in accordance with methods already described herein (e.g., with a needle 114' as described with respect to FIGS. 2G-2L). Accordingly, one or both distal ends of the tail portions 706, e.g., filaments 712, may be shaped as plugs 719 (see FIG. 6A). The plugs 719 may have a diameter equal to or greater than the other portions of the device 702. As a result, the plugs 719 may act as a barrier to the entry of tissue into the delivery needle, e.g., needle 114', during implantation.

Figure 6D:
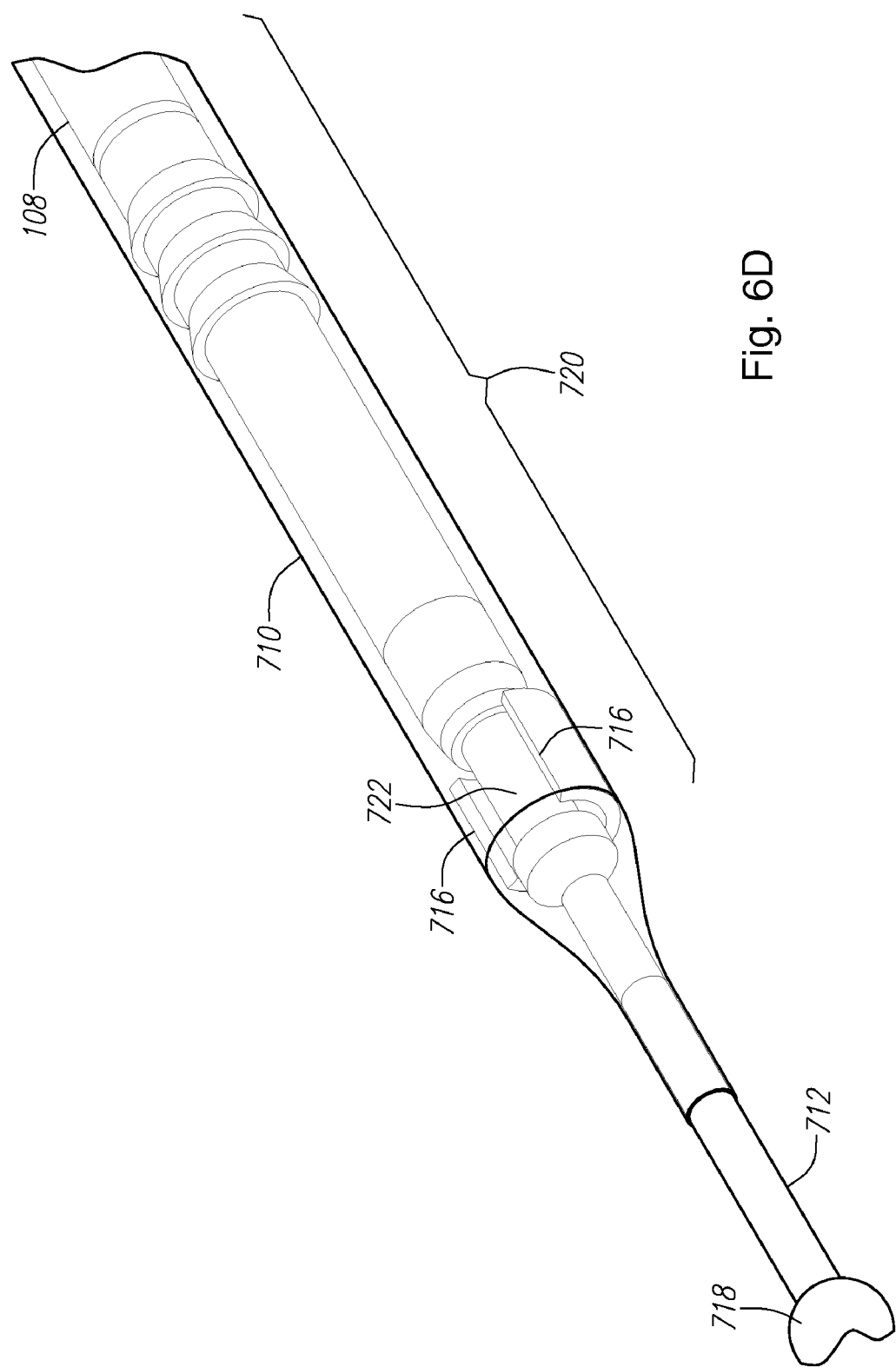

FIG. 6D is an enlarged view of a portion of the device 702. For clarity, the tubing 710 is illustrated in this view as transparent. However, translucent or opaque tubing may also be used. As clearly illustrated in this view, the filament 712 may include a proximal end section 720 defining a groove 722 therein. The groove 722 may be sized to fit within the end tabs 716 as shown. In some embodiments, the end tabs 716 may be crimped to trap the proximal end section 720 in place, e.g., at the groove 722. In other embodiments, clearances between the proximal end section 720, e.g., the groove 722, and the end tabs 716 may be selected to ensure adequate fixation of the filament 712 (at least until the tubing 710 is in place) without a crimping operation.

The length of the proximal end portion 720 of each filament 712 may be selected to position the adjacent seed 108 in the desired location. As a result, the proximal end portion 720 may also function as a marker, e.g., visual marker, indicating the beginning/end of the therapy delivery portion 704 of the device 702.

The tubing 710 may encapsulate both the tray 708 and the ends of the filaments 712 to provide a smooth transition therebetween. The tubing 710 may further assist in retaining the filaments relative to the tray 708. The tubing 710, as well as the filaments 712, may also include additional markings, e.g., centimeter markings, to indicate position. In addition, the tubing 710 (rather than the proximal end section 720 of the filaments) could incorporate markers to indicate the outermost edge of the radioactive seeds 108.

Figure 6E:
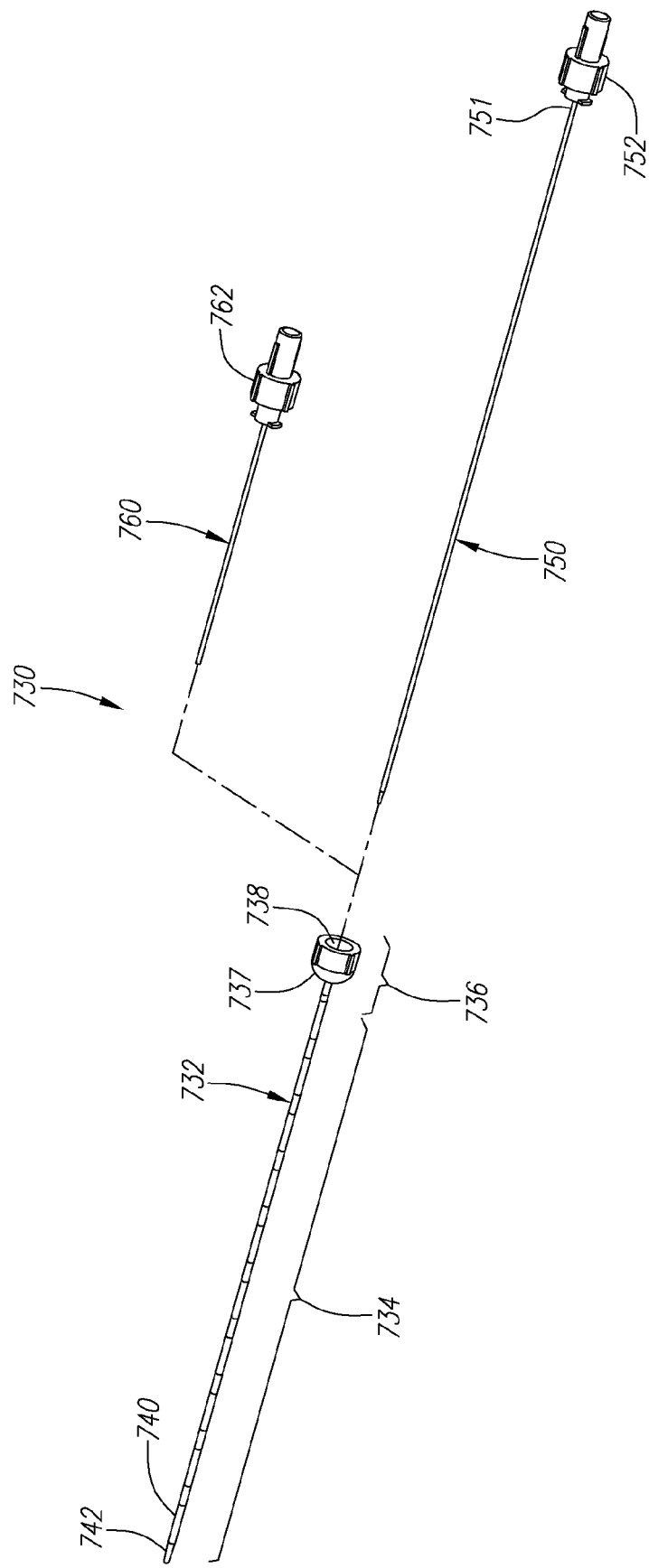

FIGS. 6E-6H illustrate an brachytherapy apparatus 730 in accordance with yet another embodiment. As shown in FIG. 6E, the apparatus 730 may include a therapy delivery device 732 having both a therapy delivery portion 734, and a tail portion 736 that extends outside the body after implantation. The therapy delivery portion 734 may be surrounded by a sleeve, e.g., tubing 740, to secure the various components of the therapy delivery portion relative to one another. As further described below, the apparatus 730 may also include a needle (e.g., trocar) 750 and a removal tool 760, both of which may be passed through the therapy delivery device 732. By utilizing a hollow device 732 with an internal needle 750, the apparatus 730 may allow a reduction in puncture/insertion diameter relative to those embodiments that utilize a hollow, external needle.

Figure 6F:
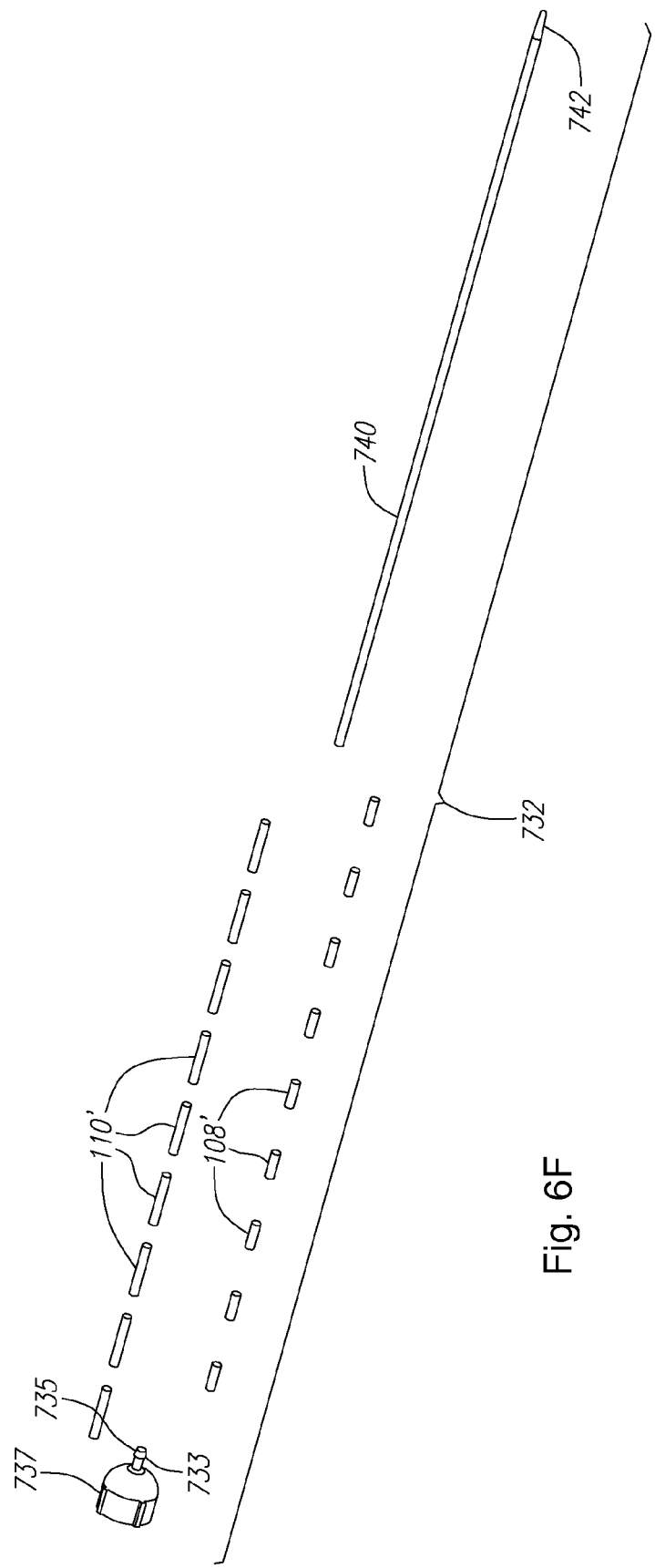

FIG. 6F is an exploded view of the therapy delivery device 732 of the apparatus 730. As illustrated in this view, the device 732 may include hollow seeds 108' separated by hollow spacers 110'. Unlike the seeds and spacers described previously, the seeds 108' and spacers 110' have tubular bodies and thus form a hole or opening extending between their respective first and second ends (e.g., each seed and spacer has a ring-shaped cross-section). When the seeds 108' and spacers 110' are aligned, the openings form a lumen 738 (see FIG. 6E) extending entirely through the device 732. The lumen 738 may be sized to receive the needle 750 and the removal tool 760 as further described below.

While the seeds 108' may be of most any material and shape that provide the desired lumen, they may, in one embodiment, be a continuous filament such as that provided by the GENETRA brand linear Pd-103 radiation source sold by Radiomed Inc., of Tyngsboro, Mass., USA, or a conventional seed such as the model INTERSOURCE-125 hollow seed produced by IBT, Inc. North America of Norcross, Ga., USA.

Unlike most of the tail portions described herein, the tail portion 736 may be formed from a generally rigid hub 737 (e.g., made from polycarbonate, nylon, or other plastic material) that is rigidly attached to the therapy delivery portion 734. The hub 737 may include a tubular protrusion 735 as shown in FIG. 6F that is captured by the casing, e.g., tubing 740. The protrusion 735 may be formed of a different material (e.g., stainless steel) that is co-molded with the hub material. Alternatively, the protrusion 735 could be formed from the same material as the remainder of the hub. The protrusion 735 may include one or more barbs 733 that assist in securing the hub 737 to the remainder of the device 732 via the tubing 740. That is, the barb(s) 733 may provide increased resistance to separation of the tubing 740 from the hub 737.

The tubing 740 may be similar in most respects to the tubing already described herein (see, e.g., tubing 112). However, the device 732 may further benefit from a shaped distal end 742 of the tubing 740 such that a smooth transition in diameter exists from the needle 750 to the therapy delivery portion 734 as perhaps best illustrated in FIG. 6G. To achieve such shaping, the distal tip 742 of the tubing 740 may be thermoformed.

Figure 6G:
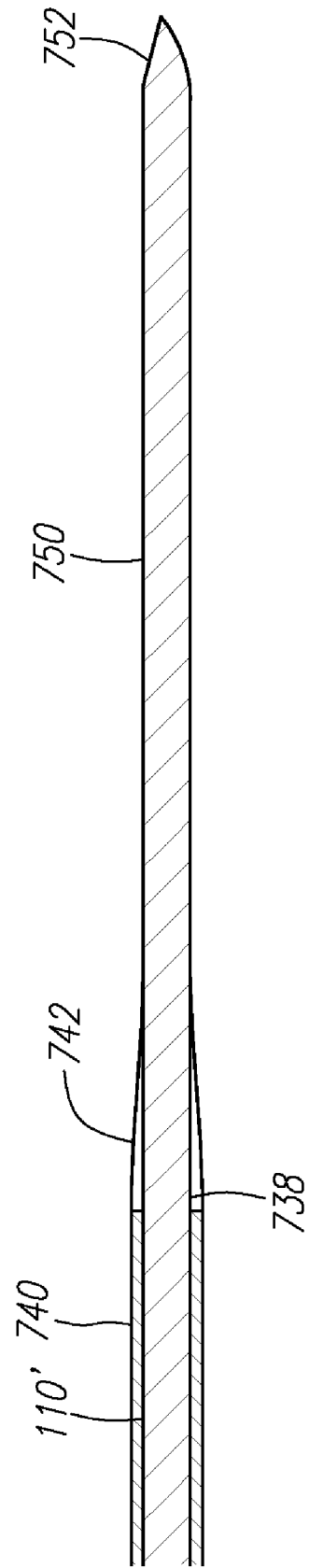

As further illustrated in FIG. 6G, the needle 750 and the removal tool 760 may have an outer diameter that fits within the lumen 738 formed by the seeds 110' and spacers 108'. A distal tip of the needle 750 may include a sharp tip, e.g., tri-face knife edge 753, to pierce the body, e.g., breast tissue, during implantation.

In use, the seeds 108', spacers 110', and hub 737 may be assembled and the tubing 740 heat-shrunk in place. This process may be completed with the needle 750, or some other mandrel, in place to hold all components in the proper orientation/position. With the needle 750 positioned within the lumen 738, a hub lock 752 at a proximal end 751 of the needle (see FIG. 6E) may be engaged (e.g., threadably engaged) with the hub 737. The device 732/needle 750 may then be inserted into the body and positioned via acceptable methods. Once in place, the hub lock 752 may be unthreaded from the hub 737 and the needle 750 withdrawn from the device 732, leaving the device implanted. During implantation, the tail portion, e.g., hub 737, is located outside the body.

Figure 6H:
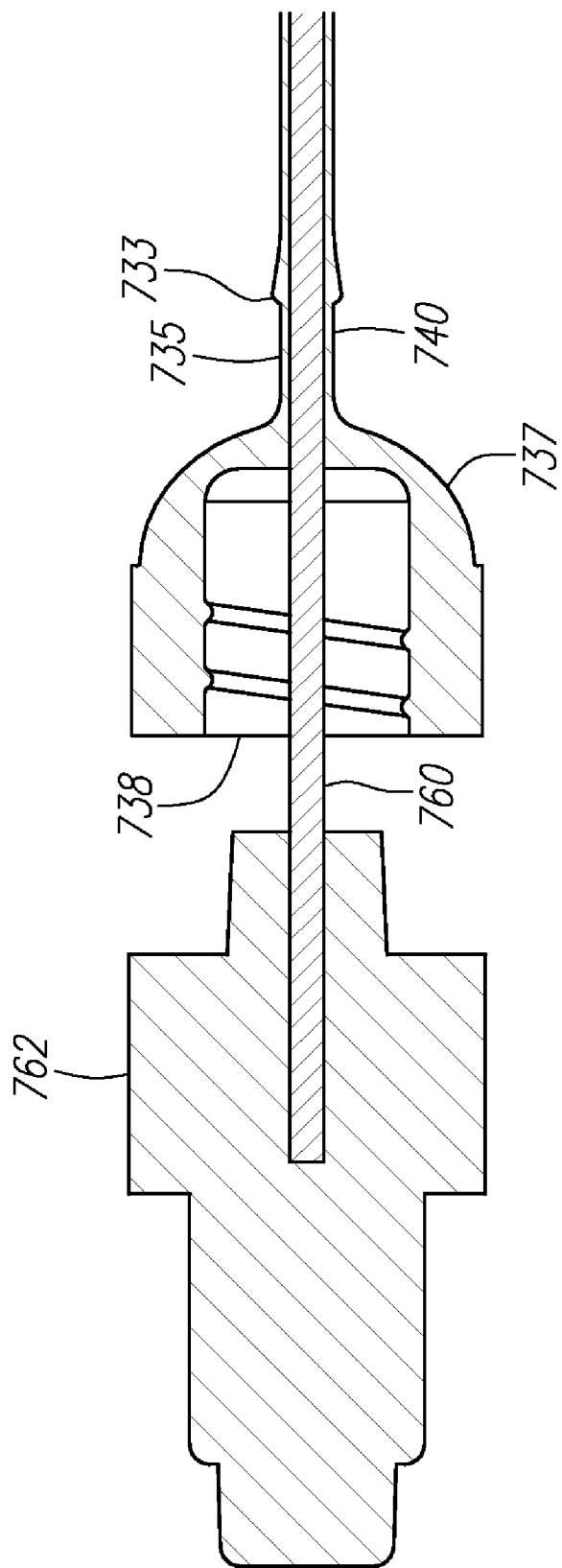
Figure 61:
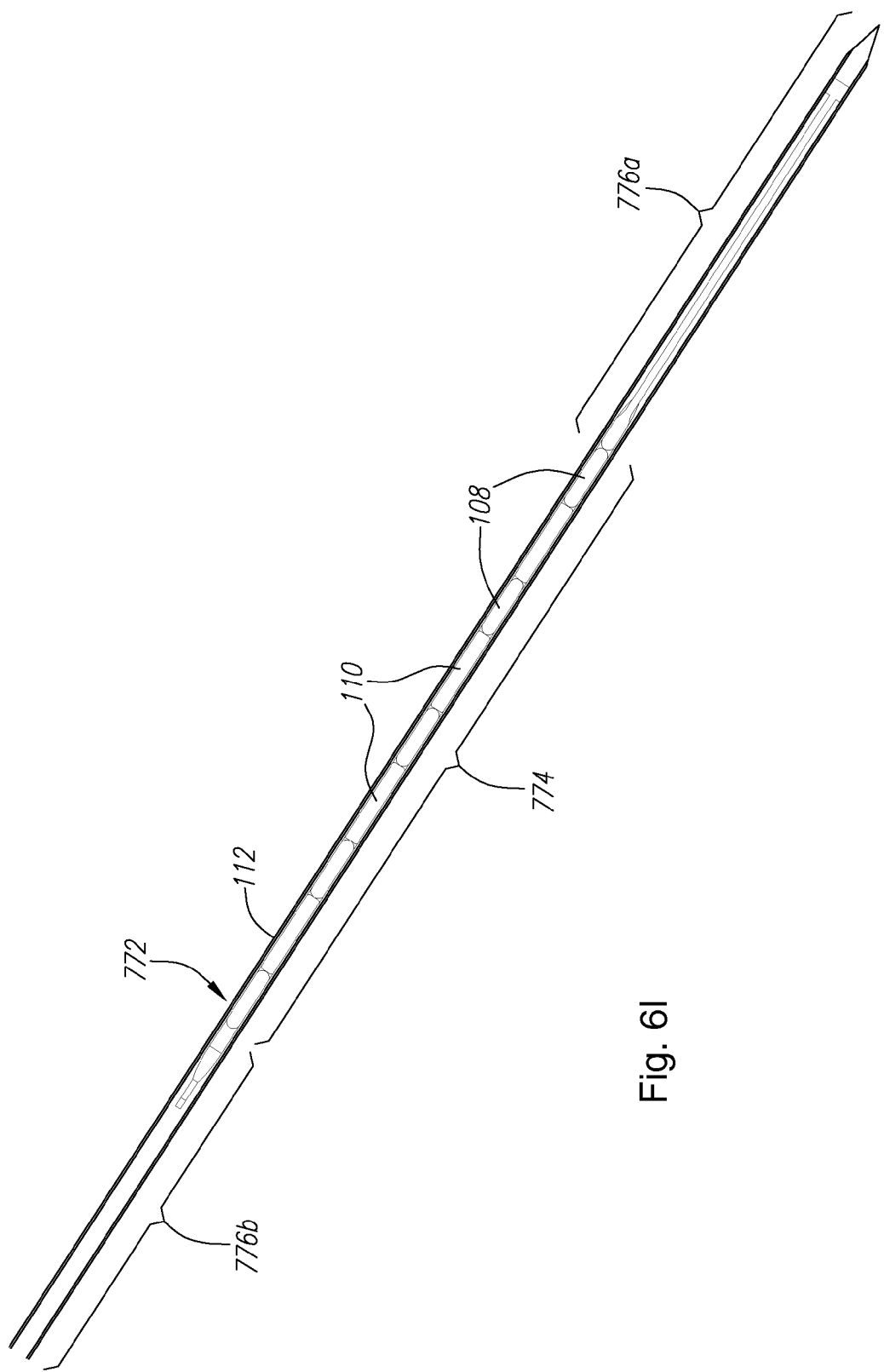

To remove the device 732, the removal tool 760 may be inserted into the lumen 738, which remains open during implantation, via the exposed hub 737. Like the needle 750, the removal tool 760 may include a hub lock 762 that threadably engages the hub 737 of the device 732 as indicated in FIG. 6H. Once engaged, the combined device 732/removal tool 760 may be withdrawn from the body. The removal tool 760, like the needle 750, may provide improved rigidity to the device while the latter is being manipulated, e.g., removed.

While illustrated herein as utilizing a removal tool, other embodiments may permit removal without the tool 760, e.g., by application of a force directly to the hub 737.

Figure 6J:
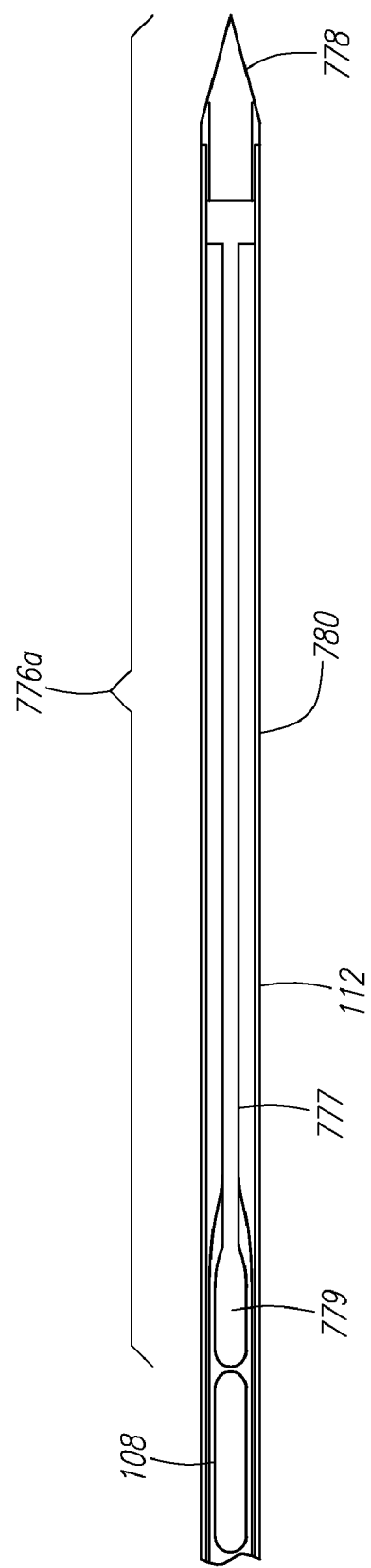

FIGS. 6I and 6J illustrate a therapy delivery device 772 in accordance with yet another embodiment. The device 772 is similar to the therapy delivery devices already described herein in that it may include seeds 108 and optional spacers 110 that form a therapy delivery portion 774. Like other devices described herein, the device 772 may also encase at least the therapy delivery portion 774 in tubing 112 (already described herein). Tail portions 776a and 776b may also be provided and extend outwardly from each end of the therapy delivery portion 774.

As illustrated in FIG. 6J, however, at least the distal tail portion 776a may further include a filament 777. The filament 777 may extend from the therapy delivery portion 774 outwardly to or near a sharp distal tip 778. The filament 777 may include an enlarged end 779, e.g., the same diameter as the seed 108, to permit adequate restraint of the filament with the shrink tubing 112.

The device 772 may fit within a hollow needle 780 that may be relative rigid. The distal tip 778 may, in one embodiment, be configured as a nosecone that fits, e.g., with interference, into the distal end of the needle 780 as illustrated in FIG. 6J.

During use, the needle 780, with the device 772 contained therein and the distal tip 778 attached, may penetrate the body. The distal tip 778 may include sharp symmetrical edges (e.g., a pyramidal trocar tip) to penetrate tissue without excessive wandering. The needle 780 may be passed completely through the body, e.g., through the breast 200, in a manner similar to that described with respect to the needle 114' described above. Once the distal tip 778 exits the distal side of the breast, the distal tip may be removed from the needle 780. From the proximal end of the needle 780, the distal tail portion 776a of the device 772 may be advanced out of the distal end of the needle in a manner similar to that illustrated in FIG. 21. The physician may then grasp the distal tail portion 776a and, while holding the tail portion 776a, withdraw the needle 780 from the proximal incision point (see FIG. 2J). The device 772 may then be adjusted and secured as already described herein (see, e.g., FIGS. 2K and 2L).

With any of the methods described herein, the time that the brachytherapy devices remain implanted may vary according to the desired therapy regimen. While not wishing to be bound to any fixed period, implantations from about one hour up to about eight weeks or more are contemplated for therapy. However, for breast brachytherapy, implantation periods ranging from about one day to several weeks, e.g., four to ten days, are more likely. Moreover, because of the construction of the devices, e.g., devices 102, they may be removed over a range of timeframes subsequent to implantation. This is in contrast to the permanent placement typically associated with conventional LDR brachytherapy and the short exposure time associated with conventional HDR brachytherapy. As a result, intermediate activity radiation sources may be utilized with the methods and apparatus described herein, as well as conventional low and, as further described below, high activity sources.

Figure 7A:
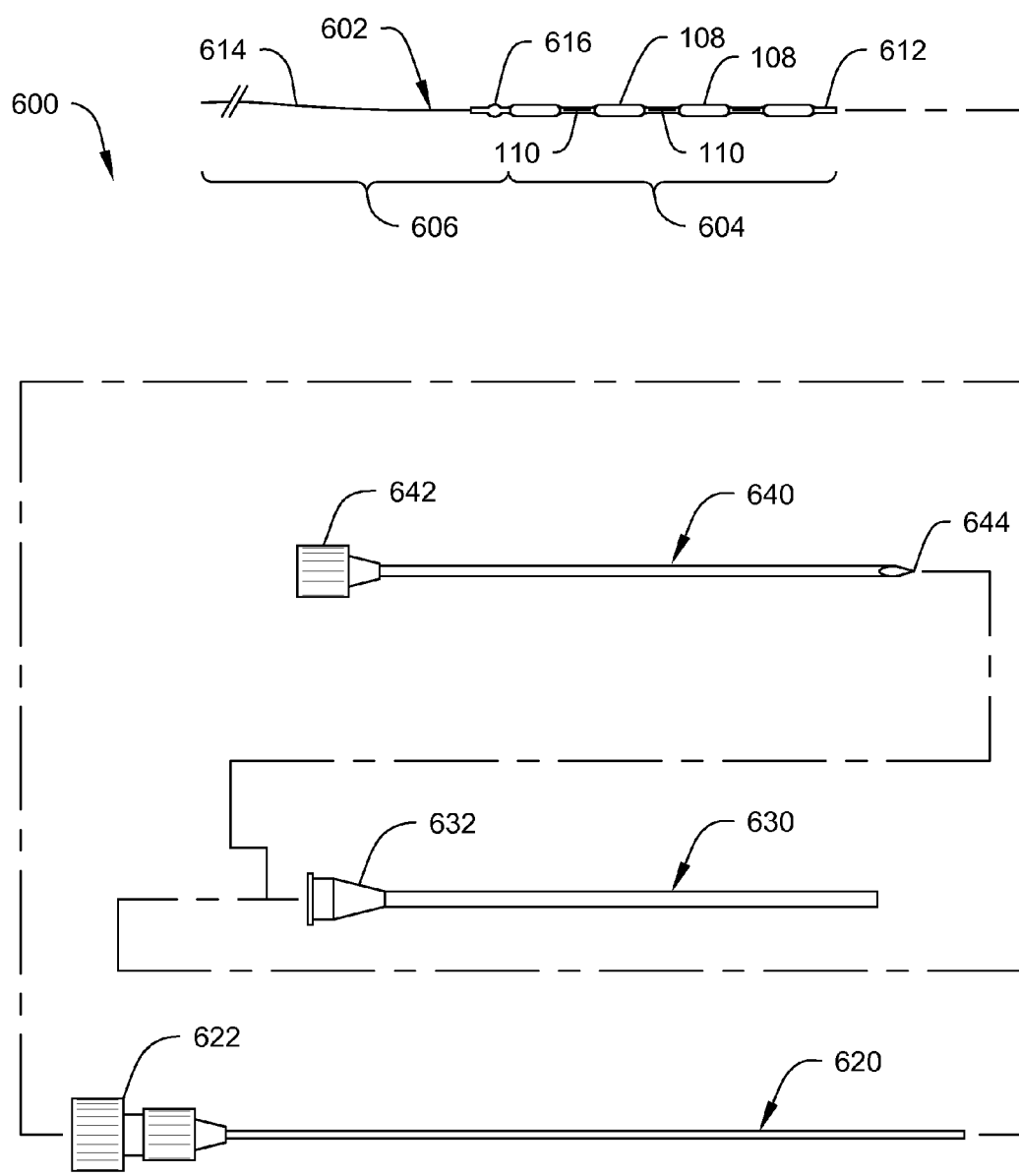
FIG. 7A is an exploded view of a brachytherapy apparatus or kit in accordance with yet another embodiment.

FIG. 7A illustrates a brachytherapy kit or apparatus 600 in accordance with another embodiment. Unlike the apparatus 100 of FIG. 1A, the apparatus 600 may include, among other components, at least a removably implantable brachytherapy treatment device (brachytherapy device 602), a pusher or pusher member 620, a catheter, e.g., cannula or cannula member 630, and a sharp obturator 640.

The therapy device 602, once again, may include a therapy delivery portion 604 and a removal or tail portion 606. The therapy delivery portion 604 may include one or more seeds 108 and optional spacers 110. The seeds 108 may be enclosed within a casing, e.g., heat-shrinkable tube or tube member 612, similar in most respects to the tube 112 described above.

The tail portion 606 in this embodiment, however, is formed by an elongate filament or wire, e.g., a non-dissolving surgical suture 614, coupled or otherwise attached to the therapy delivery portion 604. While most any method of attaching the suture 614 to the therapy delivery portion 604 is possible, one embodiment forms a knot 616 in the suture. The knot 616 may be captured when the tube 612 is heat-shrunk to the therapy delivery portion 604. In other embodiments, the suture 614 may be knotted around or otherwise attached directly to the therapy delivery portion 604. Such suture attachment methods are exemplary only, however, as most any other method of attaching the suture 614 to the therapy delivery portion 604 is possible. The suture 614, as with the tail portion 106 described above, may be made from a non-dissolving material, e.g., polypropylene, polyester, polyamide.

The pusher member 620 may include a lumen through which the therapy device 602 may pass as indicated in FIGS. 6 and 7. The pusher member may include a suture locking device 622, e.g., a luer hub, at a proximal end to assist with loading and securing of the therapy device 602. The locking device 622 may secure the suture 614 relative to the pusher 620 as further described below. While illustrated as a luer hub, the locking device 622 may include most any friction or clamping device known in the art. For example, the locking device may be an O-ring that may be selectively compressed to pinch the suture 614.

The cannula member 630 may also include a lumen through which the pusher member 620 may pass as indicated in FIG. 7A. The cannula member 630 may include a luer hub 632 at its proximal end that is operable to secure the cannula member relative to the either the sharp obturator 640 or the pusher member 620 when either is slid into the lumen of the cannula member as further described below.

The sharp obturator 640 may include a handle portion with a hub 642 at a proximal end, and a sharp point 644 operable to pierce body tissue at its distal end. The handle portion may permit comfortable manipulation of the obturator 640. The external diameter of the obturator 640 may be sized so that it fits within the lumen of the cannula member 630 as indicated in FIG. 7A.

The components of the apparatus 600 may be made from most any suitable biocompatible material. For example, the cannula member 630, the pusher member 620, and the sharp obturator 640 may be made from metal, e.g., stainless steel or Titanium, or plastic.

FIG. 7B illustrates the apparatus 600 as it may be assembled prior to use. The sharp obturator 640 may be placed into the cannula 630 such that the sharp distal end 644 of the obturator protrudes from the distal end of the cannula 630 as illustrated. The therapy device 602, which includes the therapy delivery portion 604 and the suture 614 as described above, may be positioned within the pusher member 620 such that the therapy delivery portion 604 extends from its distal end and the suture 614 extends from the hub 622 at its proximal end. The suture 614 may be pulled from the proximal end of the pusher member 620 until the therapy delivery portion 604 is at or near the distal end of the pusher member 620 as shown. The locking device 622 may then be engaged to hold the suture 614, and thus the therapy delivery portion 604, in place relative to the pusher member 620.

FIGS. 8A-8E illustrate an exemplary method of using the system 600 for delivery of brachytherapy to a portion of a body, e.g., breast 200. Once the target tissue region 202, e.g., tumor or tumor cavity, is identified, the combined cannula 630 and sharp obturator 640 (see FIG. 7B) may be advanced into the target tissue region 202 as illustrated by arrow 802 in FIG. 8A. When the distal end of the cannula 630 reaches the desired depth, the sharp obturator 640 may be removed (moved in the direction 804) through the proximal end of the cannula as shown in FIG. 8B, while leaving the cannula 630 in place.

The combined pusher member 620 and therapy device 602 (see FIG. 7B) may then be inserted into the proximal end of the cannula 630, in the direction 806, as shown in FIG. 8C. The pusher 620, and therapy device 602, may be inserted until the therapy portion 604 is at its desired location, e.g., at or near the distal end of the cannula 630. Location of the therapy portion 604 may be assisted by image guidance, e.g., stereotactic X-ray, ultrasound, CT, etc.

Once the therapy portion 604 is positioned, the cannula 630 may be retracted (moved in the direction 808), exposing the therapy portion 604 to the target tissue region 202 as shown in FIG. 8D. The locking device 622 may then be unlocked such that the pusher member 620 and cannula 630 may be fully withdrawn (moved in the direction 810) from the body 200 as shown in FIG. 8E. The therapy delivery portion 604 remains implanted at the target tissue region 202 while the suture 614 extends outside the body.

These steps may be repeated for placement of each brachytherapy device 602, or multiple devices may be implanted as a group as further described below.

Although not illustrated, a locking member, such as the locking member 120 illustrated in FIGS. 2E and 27, may be used to secure the therapy device 602, e.g., the tail portion(s) 606, at one or both (see FIG. 2F) ends. Alternatively, the therapy device 602 may include securing elements such as the anchors 516 shown in FIG. 5. Still further, the therapy device 602 may be secured simply by folding and adhering the tail portions 606 to the breast 200 (see FIGS. 2E and 26).

After the desired dose of radiation has been delivered, the therapy delivery device 102 may be removed in any number of ways as already described herein, e.g., using a removal member, such as the tail portion 606, or a removal cannula.

FIG. 9A is an enlarged view of the therapy device 602 of FIGS. 6-7. As clearly illustrated in this view, the therapy device 602 may include the therapy delivery portion 604 and the tail portion 606. The therapy delivery portion 604 may include one or more radioactive seeds 108 securely retained within the casing, e.g., heat-shrinkable tube 612. The tail portion 606 may be formed by the suture 614. The knot 616 of the suture 614 may be secured to the therapy delivery portion 604 by the heat shrinkable tube 612. While shown as utilizing spacers 110, they may not be required in some embodiments, e.g., the conformal properties of the casing, e.g., tube 612, may be sufficient to ensure proper seed 108 spacing and containment. FIG. 9B illustrates a section view of the seed 108 and tube 612 taken along line 9B-9B of FIG. 9A.

FIGS. 10A-10B illustrate a therapy device 1002 in accordance with another embodiment. The device 1002 is similar in many respects to the device 602 described above. For example, the device 1002 may include a therapy delivery portion 1004 and a tail portion 1006. A casing, e.g., heat shrinkable tube 1012, may be used to encase the seeds 108 and optional spacers 110. Like the device 602, the tail portion 1006 may be formed by a suture 614 having a knot 616 that may be heat shrinkable to the therapy delivery portion 1004. However, unlike the device 602 of FIGS. 9A-9B, the tube 1012 may include a radioabsorptive portion 1014 positioned along a part of the circumference of at least the therapy delivery portion 1004 (see FIG. 10B). The radioabsorptive portion 1014, which may be formed integrally or separately with the tube 1012, may limit radiation exposure to tissue blocked by the radioabsorptive portion. FIG. 10B illustrates a section view of the seed 108 and tube 1012 taken along line 10B-10B of FIG. 10A.

FIGS. 11A-11B illustrate a therapy device 1102 in accordance with yet another embodiment. The device 1102 is similar in many respects to the device 602 described above. For example, the device 1102 may include a therapy delivery portion 1104 and a tail portion 1106. A casing, e.g., heat shrinkable tube 1112, may be used to encase and constrain the seeds 108 and optional spacers 110. Like the embodiment illustrated in FIGS. 5A and 5B, the therapy device 1102 may incorporate an anchor member, e.g., anchor wire 1114, which extends along at least a part of the therapy delivery portion 1104 and protrudes from one or both ends. The anchor wire 1114 may be bent at one or both ends to form anchors 1116. When the therapy delivery portion 1104 exits the cannula 630 (see FIG. 8D), the anchors 1116 may extend and capture surrounding tissue, thereby assisting in preventing migration of the therapy device 1102. FIG. 11B illustrates a section view of the seed 108 and tube 1112 taken along line 11B-11B of FIG. 11A.

It is to be understood that any of the various components of the embodiments described herein may be used interchangeably with any other of the described methods and systems. For example, any one of the devices 102, 402, 502, 562, 572, 602, 582, 1002, and 1102 could be used with other methods described herein such as those described in FIGS. 2A-2E, 2F, 2G-2L, and 8A-8E.

The embodiments described above utilize a therapy delivery portion (e.g., portion 104 of FIG. 1A or portion 604 of FIG. 7A) formed primarily by the shrink fit tube (e.g., tube 612 of FIG. 9A) and seeds 108. However, other embodiments of the therapy delivery portion may include an additional support member. The support member may be any material that lends support to the therapy delivery portion, e.g., a strip of material such as stainless steel or superelastic nickel titanium alloy. In addition to partially supporting the seeds 108, the material of the support member may divide the therapy delivery portion into a radiotransparent portion and a radioabsorptive portion. That is, it may partially surround at least a portion of the seeds 108 to provide some degree of attenuation or shielding of radiation to surrounding tissue. As a result, tissue on a side of the support member opposite the seeds 108 may receive a lower dose of radiation than tissue on the seed side. The support member may be enclosed within the casing, e.g., heat-shrinkable tube 112 or 612.

For example, FIGS. 12A and 12B illustrate a therapy device 1202 having a tail portion 1206 and a therapy delivery portion 1204 with a plurality of seeds 108 and a straight support member 1210 (see FIG. 12A). The support member 1210 may have a curved, e.g., arc-shaped, cross-section (see FIG. 12B). Alternatively, a relatively flat cross-section (not shown) may be provided. Other embodiments may utilize most any other cross-sectional shape, e.g., v-shaped. The support member 1210 may also have a variety of leading edge shapes including the shovel-tip shape illustrated in FIG. 12A. Some or all of the support member 1210 may be encased within a casing, e.g., heat shrinkable tube 1212, as already described above.

While the support member 1210 of FIG. 12A is generally straight, other support members may be provided, which may be curved, e.g., may have some degree of curvature. For example, FIG. 13A illustrates a therapy device 1302 having a therapy delivery portion 1304 with a curved support member 1310 that imparts an arc- or otherwise curved-shape to the delivery portion 1304. The support member 1310 may be formed to have curvature in its relaxed state or may simply be sufficiently flexible to permit curved implantation. As with the support member 1210 of FIGS. 12A-12B, the support member 1310 may have most any cross-sectional shape, e.g., flat, curved (as shown in FIG. 13B), V-shaped, etc. Some or all of the support member 1310 may be encased within a casing, e.g., heat shrinkable tube 1312, generally identical to the casings already described above. FIG. 13B illustrates a section view taken along line 13B-13B of FIG. 13A.

While not illustrated herein, optionally, the support members may include one or more slots, e.g., along a centerline, so that seeds may be placed at least partially within the slot. As a result, a therapy delivery portion that offers more rigidity than the unsupported therapy delivery portions described herein may be obtained while ensuring tissue on both sides of the support member receives radiation treatment.

FIGS. 14A-14B illustrate another exemplary embodiment of a therapy delivery portion 1404. In this embodiment, the therapy delivery portion includes a catheter or casing, e.g., tube 1412, having one or more lumens. A first or main lumen 1408 may receive the seeds (not shown), while a second lumen 1414 may contain an attenuating or shielding element 1416 extending over a longitudinal length of the tube 1412. As a result, the tube 1412 may have a radiotransparent portion (that portion not blocked by the element 1416), and a radioabsorptive portion (that portion shielded by the element 1416). In one embodiment, the tube 1412 can be made by co-extruding plastic (e.g., fluoropolymer) with an attenuating material such as strands of fine metallic wire (e.g., stainless steel, gold). In another embodiment, the attenuating material may be a coextrusion of polymer loaded with an attenuating material such as Tungsten powder. The tube 1412 may or may not be heat-shrinkable. For versatility, the shielding element 1416 may be straight or preformed in a curve. FIG. 14B illustrates a section view taken along line 14B-14B of FIG. 14A.

FIG. 15 is a partial view of an exemplary brachytherapy apparatus 1500 having a therapy device 1502 and catheter, e.g., cannula 1501, wherein the device 1502 includes a curved therapy delivery portion 1504, and a tail portion 1506. Other components of the system, e.g., pusher member and sharp obturator, are not illustrated in this view. The curved therapy delivery portion 1504 may be formed by a curved support member such as support member 1310 of FIG. 13A. The cannula 1501 may have a lumen diameter sufficiently large to accommodate the curved therapy delivery portion 1504 when the latter is constrained in a straightened configuration for delivery. Alternatively, the cannula 1501 may be sized to receive the therapy delivery portion 1504 when the latter is in its curved configuration. In still yet other embodiments, the therapy delivery portion 1504 may be generally straight but flexible and the cannula 1501 used to deliver the therapy delivery portion may be curved.

Figure 16A:
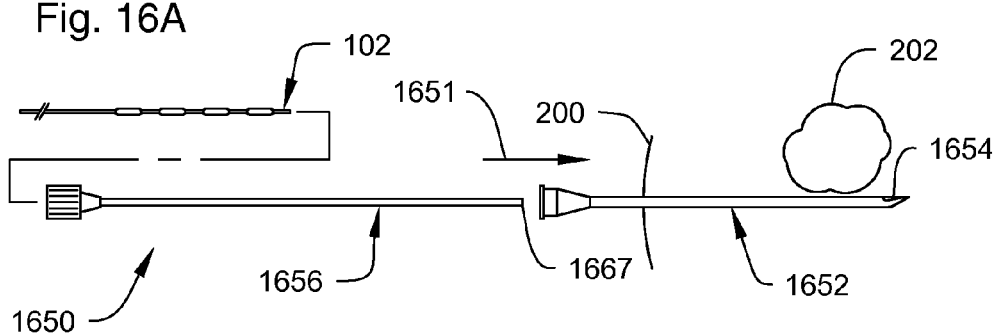
Figure 16B:
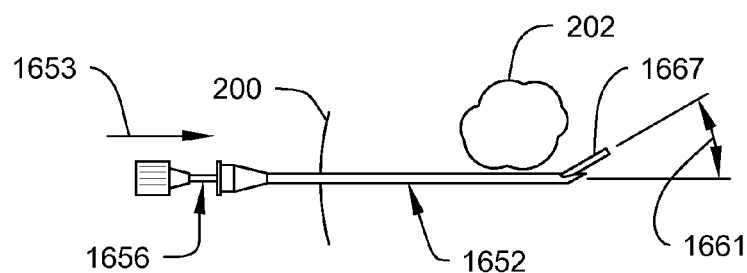

Non-linear (e.g., curved) catheters may also be used for delivery and placement of the brachytherapy devices described herein to regions and positions inaccessible to straight catheters. For example, FIGS. 16A-16E illustrate an exemplary apparatus 1650 and method operable to implant a brachytherapy device, e.g., device 102 of FIG. 1A, along a non-linear axis. FIG. 16A illustrates the apparatus 1650 including a first catheter member, e.g., needle 1652, a second catheter member, e.g., flexible catheter 1656, and a brachytherapy device 102. The needle 1652 includes an off-axis opening 1654 at or near a distal end of the needle. The needle 1652 may be inserted into the body 200, in the direction 1651, until the distal end is positioned past the target tissue region 202 as shown in FIG. 16A. The flexible catheter 1656 may then be inserted through the needle 1652 (in the direction 1653) until a distal end 1667 of the catheter 1656 protrudes from the opening 1654 of the needle 1652 at an angle 1661 as shown in FIG. 16B. That is, an axis of the catheter 1656 may intersect, or be otherwise nonparallel to, an axis of the needle 1652.

The angle 1661 between the axes may vary, but angles ranging from greater than about zero to about ninety degrees (0-90°), or between about five to about thirty five degrees (5-35°), are contemplated.

Figure 16C:
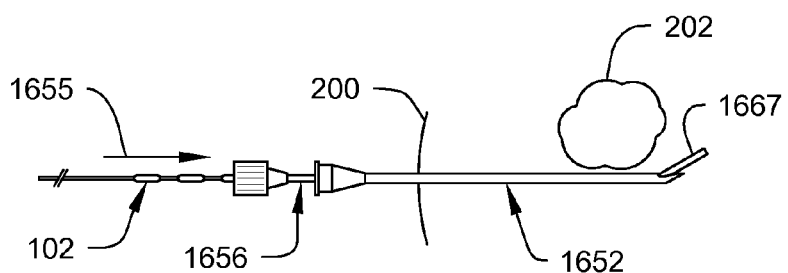

The device 102 may then be threaded through the catheter 1656 (in the direction 1655), as shown in FIG. 16C, until the therapy delivery portion of the device 102 is located at or near the distal end 1667 of the catheter 1656.

Figure 16D:
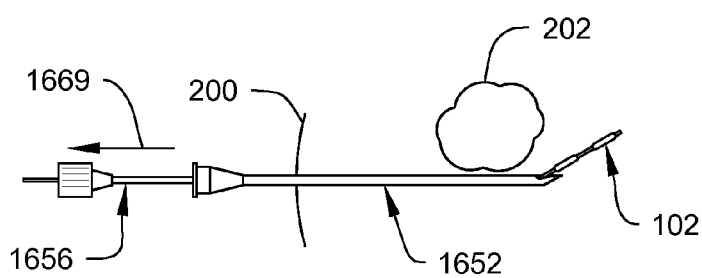
Figure 16E:
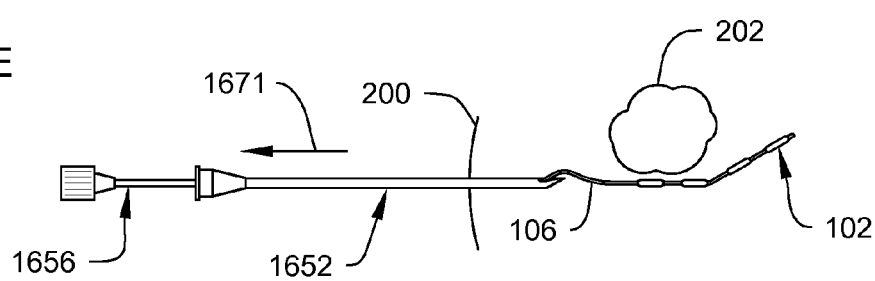

At this point, the catheter 1656 may be withdrawn slightly (in the direction 1669) as shown in FIG. 16D, exposing the therapy delivery portion of the device 102. The needle 1652 and catheter 1656 may then be withdrawn (in the direction 1671) from the body 200 together as shown in FIG. 16E. The device 102 is then implanted on a non-linear axis with its tail portion 106 extending outside the body as generally described above with reference to other embodiments (see e.g., FIGS. 2A-2E).

The ability to implant the device 102 along a non-linear axis may be beneficial in many applications. For example, where the target tissue region 202 is a breast lesion or a lumpectomy cavity in the breast, the non-linear device 102 may provide the capability to better focus radiation. Further, non-linear positioning may permit implantation around obstructions in the body. For example, in prostate brachytherapy, the region 202 could be a pubic arch around which the clinician desires to place radiation sources. While described above with respect to devices 102, the non-linear placement of FIGS. 16A-16E could also be used to implant individual radiation sources.

Figure 16F:
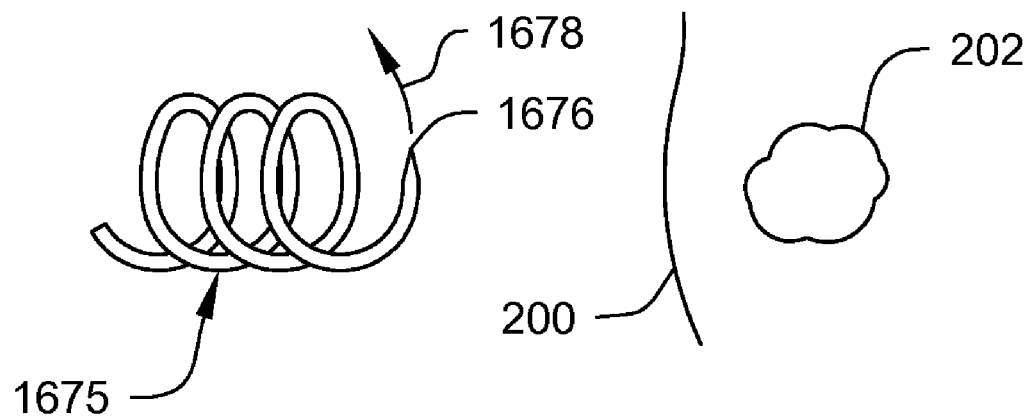
Figure 16G:
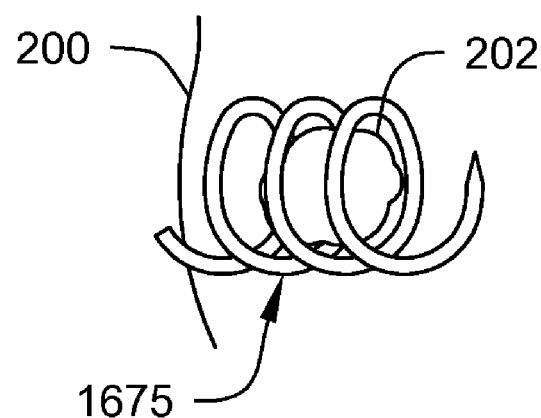

In yet other embodiments of non-linear placement apparatus and techniques, the needle 1652 of FIGS. 16A-16E may be replaced with a more spiral-shaped needle 1675 as shown in FIGS. 16F and 16G. While the actual needle size may vary depending on target tissue volume, needles having a helix diameter of about 3 centimeters (cm) are contemplated. The needle 1675 may be advanced into the body 200 in much the same way a corkscrew is inserted into a cork. That is, the needle 1675 may be rotated in a direction 1678 such that a sharp end 1676 penetrates the body 200 as indicated in FIG. 16F. FIG. 16G illustrates the needle 1675 once it is fully inserted. A flexible catheter (not shown) and therapy device (also not shown) may then be passed through the needle 1675 in much the same way as the catheter 1656 and device 102 are described with reference to FIGS. 16A-16E. The needle 1675 may then removed ("unscrewed"), leaving the therapy device in a spiral configuration around the target tissue region 202 (not illustrated).

When non-linear, e.g., off-axis, curved, and spiral, therapy delivery portions are used, the total number of therapy devices required to treat a given target tissue region may potentially be reduced as a result of the delivery portions' conformance to the shape of the target tissue. For example, in the case of curved delivery portions, several devices may be placed to curve around the target tissue region, effectively focusing radiation on a central area. This may result in lower dose exposure outside of the target tissue area, and potentially improved dose coverage within the target tissue. In the case of a spiral therapy delivery portion, a single therapy device of sufficient length may deliver adequate treatment by spiraling (e.g., forming a helix) around or within the target tissue region.

FIGS. 17A-17B illustrate an apparatus 1600 similar in most respects to apparatus 600 of FIG. 7A. For instance, it may include a therapy device 1602 having a therapy delivery portion 1604 with seeds 108, and tail portion formed by a suture 1614. The suture 1614 may pass through a pusher member 1620 and the combined pusher member 1620 and delivery device 1602 may be placed within a cannula 1630. Unlike the cannula 630, however, the cannula 1630 may have a cutout 1634, e.g., the cannula may have a C-shaped cross section, as shown more clearly in FIG. 17B, over at least a portion of its length. While shown as straight, the cannula 1630 may also be curved. The cutout configuration may protect certain surrounding tissues/organs, e.g., skin, chest wall, liver, heart, during implantation. FIG. 17B is a cross-section taken along line 17B-17B of FIG. 17A with the therapy delivery device 1602 also shown in broken lines.

Figure 18:
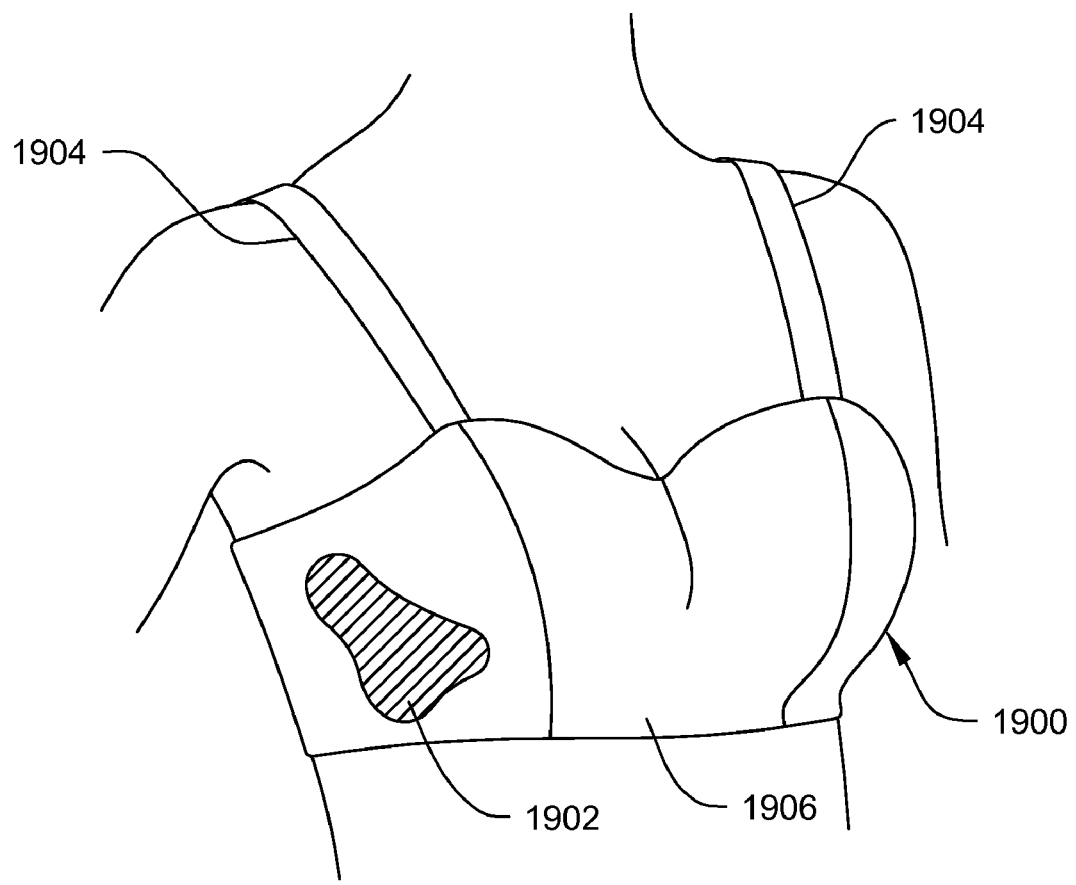
FIG. 18 is a view of a radiation attenuating garment, e.g., brassiere, in accordance with one embodiment.

During implantation of any of the devices described herein, the patient may optionally wear a protective garment, e.g., a chest covering brassiere or binder 1900, such as that illustrated in FIG. 18. The brassiere/binder 1900 may be similar in many respects to those garments described, for example, in U.S. Pat. No. 3,968,803 to Hyman; U.S. Pat. No. 5,152,741 to Farnio; and U.S. Pat. No. 5,538,502 to Johnstone. That is, it may include a partial body covering that secures via fasteners, e.g., shoulder straps 1904, to cover a portion of the chest (or other area surrounding the target tissue region). However, in addition to a fabric portion 1906, the binder 1900 may include a lining made from a radiation attenuating material 1902, e.g., lead, stainless steel, Tungsten. Such a garment may offer an added degree of shielding and permit greater patient mobility, while the indwelling radioactive sources, e.g., seeds 108, are held in their proper position, in an out-patient setting. The garment 1900 may be provided separately, or as part of a brachytherapy kit, e.g., kit 100.

Although discussed above primarily with respect to LDR brachytherapy, the apparatus and/or methods described herein may also find use in HDR applications. For example, the tube 1412 of FIGS. 14A-14B may be used as a shielded delivery catheter for HDR treatment, e.g., the tube 1412 may be located in the body and a conventional HDR source (e.g., afterload HDR cable) of smaller diameter may be passed through the main lumen 1408. The attenuating element 1416 in the wall of the catheter (along a circumferential portion extending from about 10 o'clock to about 2 o'clock, for example) may attenuate the radiation exposure of regions vulnerable to radiation while the non-shielded section of the tube 1412 (along a circumferential portion extending from about 2 o'clock to about 10 o'clock) would allow exposure to the target tissue.

Further, for example, HDR radiation sources may be passed through a catheter, e.g., the cannula 1630 of FIGS. 17A and 17B, whereby the HDR radiation sources may be partially shielded from surrounding tissue by the geometry of the cannula 1630, e.g., the cutout 1634.

Figure 19A:
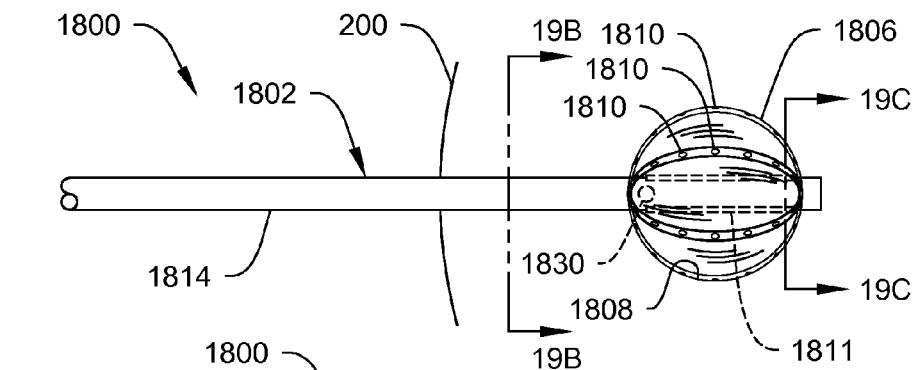
FIGS. 19A-19C are diagrammatic views of a balloon catheter assembly, e.g., HDR catheter, in accordance with one embodiment.
Figure 19B:
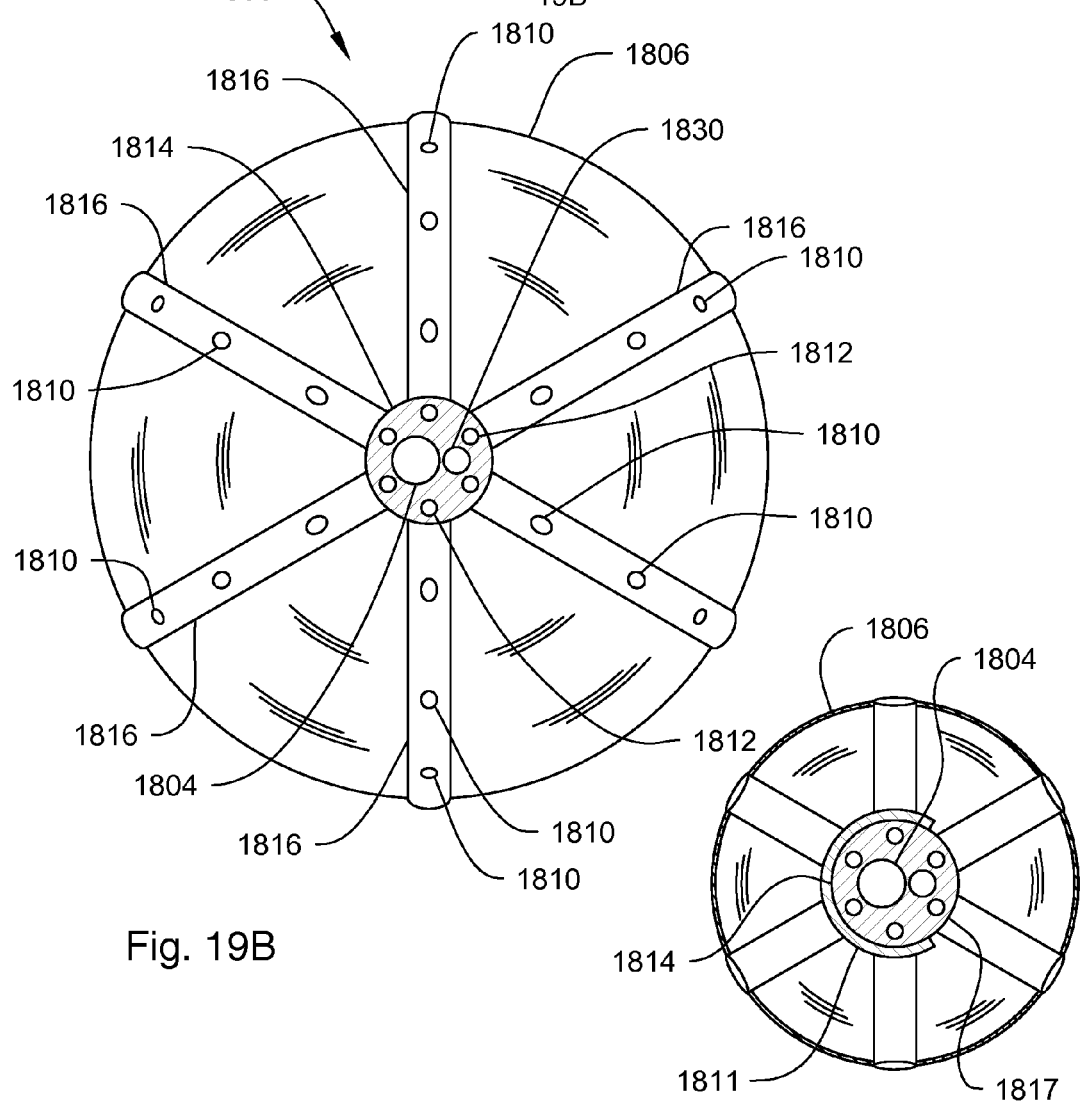
Figure 19C:

FIGS. 19A-19C illustrate incorporation of a HDR shielded catheter on a balloon-type brachytherapy treatment device 1800. The device 1800 may be similar to the device disclosed in U.S. Pat. No. 5,913,813 to Williams et al. That is, it may include a brachytherapy catheter assembly 1802 having a catheter shaft 1814 with a proximal end and a distal end. An inflatable balloon 1806 may be coupled to the catheter shaft 1814 between the proximal end and the distal end. An inflation lumen 1830 may extend along the catheter shaft 1814 between the inflatable balloon 1806 and the proximal end to allow inflation of the balloon. A dose delivery lumen 1804 (see FIG. 19B) may also be provided and extend along the catheter shaft 1814 from the proximal end towards and the distal end, e.g., extending between the inflatable balloon 1806 and the proximal end.

In use, the distal end of the catheter shaft 1814 may be placed into a cavity, e.g., a lumpectomy cavity 1808 of breast 200, and the balloon 1806 inflated. A radiation source (not shown) may then be passed through the dose delivery lumen 1804, where it delivers radiation along a dose delivery portion of the catheter shaft, e.g., along a portion surrounded by the inflatable balloon 1806. By incorporating a radioabsorptive portion (e.g., arc-shaped member 1811 clearly illustrated in FIG. 19C) over the dose delivery portion of the catheter shaft 1814, only a predetermined portion, e.g., a window 1817, of the dose delivery portion may be relatively radiotransparent. As a result, the device 1800 may attenuate the radiation exposure of select areas, e.g., those close to the skin or chest wall, while delivering higher radiation levels to target tissue not blocked by the radioabsorptive portion 1811. While the radioabsorptive portion is illustrated herein as a separate member 1811 extending along a portion of the catheter shaft 1814, other embodiments may incorporate the radioabsorptive portion into the catheter shaft 1814 itself (see. e.g., the catheters described elsewhere herein such as the tube 1412 of FIGS. 14A-14B).

In some embodiments, the device 1800 may further include a vent system having one or more vents 1810 positioned around at least a portion of an outer surface of the balloon 1806. The vents 1810 may permit air and fluids within the cavity 1808 to escape as the balloon 1806 expands. One or more vent lumens 1812 (shown in FIG. 19B) associated with the catheter shaft 1814 may extend between the proximal end of the catheter shaft 1814 and the one or more vents 1810. The vents 1810 may fluidly communicate with one or more vent lumens 1812, thereby allowing the air and fluids to exit the body at the proximal end of the catheter shaft 1814 during and after balloon expansion.

In some embodiments, the external vents 1810 and vent lumens 1812 are formed by individual pieces of tubing 1816 attached to the balloon 1806 and catheter shaft 1814. In the vicinity of the balloon 1806, the tubing 1816 may be perforated to form the external vents 1810. The portion of the tubing 1816 located proximate the catheter shaft 1814 may or may not include perforations. The tubing 1816 may be formed of most any biocompatible material that can be securely attached to, or formed with, the balloon 1806 and catheter shaft 1814, e.g., silicone tubing.

Figure 20:
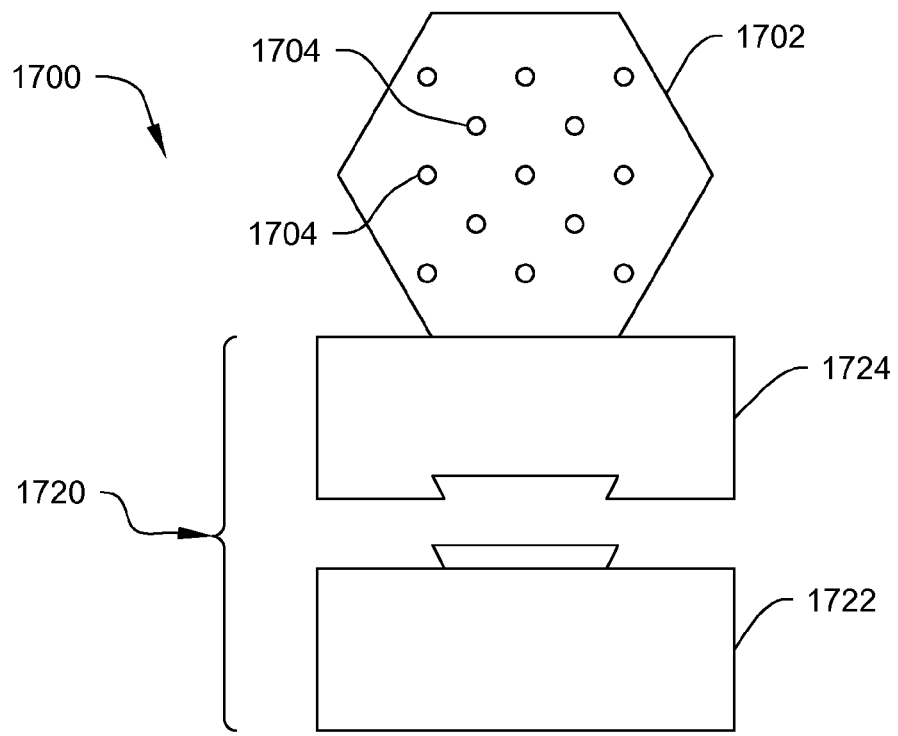
FIG. 20 is an exemplary embodiment of a delivery or implantation system for use with brachytherapy methods and apparatus described herein.
Figure 21:
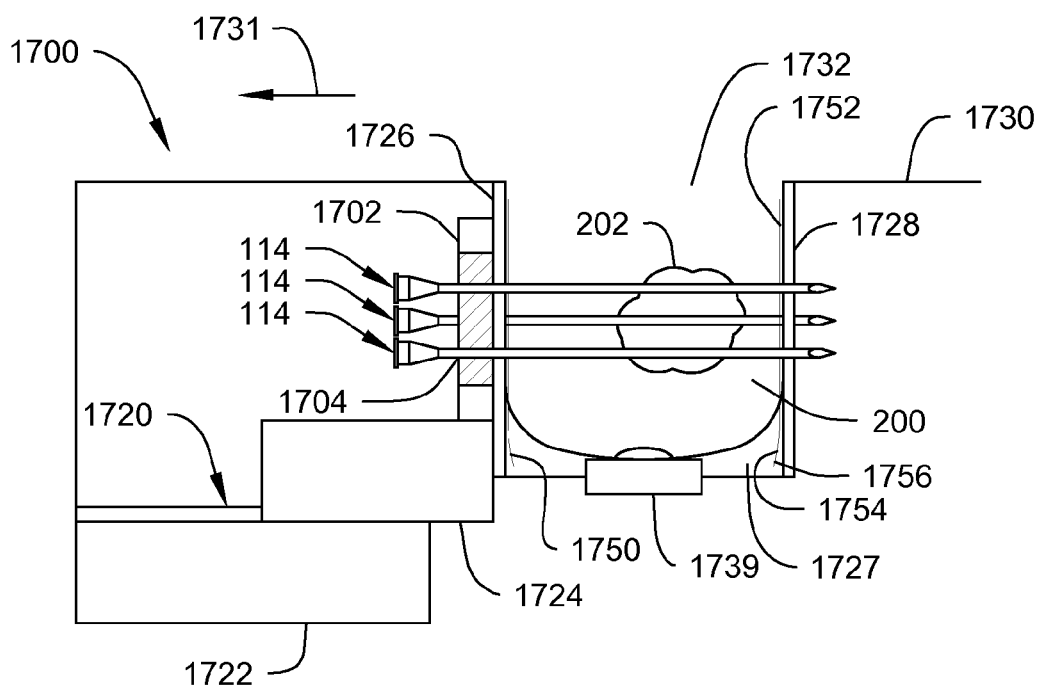
FIG. 21 is a diagrammatic view of the delivery system FIG. 20 as it may be used with the brachytherapy methods and apparatus described herein, e.g., the methods described in FIGS. 2A-2F, 2G-2L, and 8A-8E.
Figure 22:
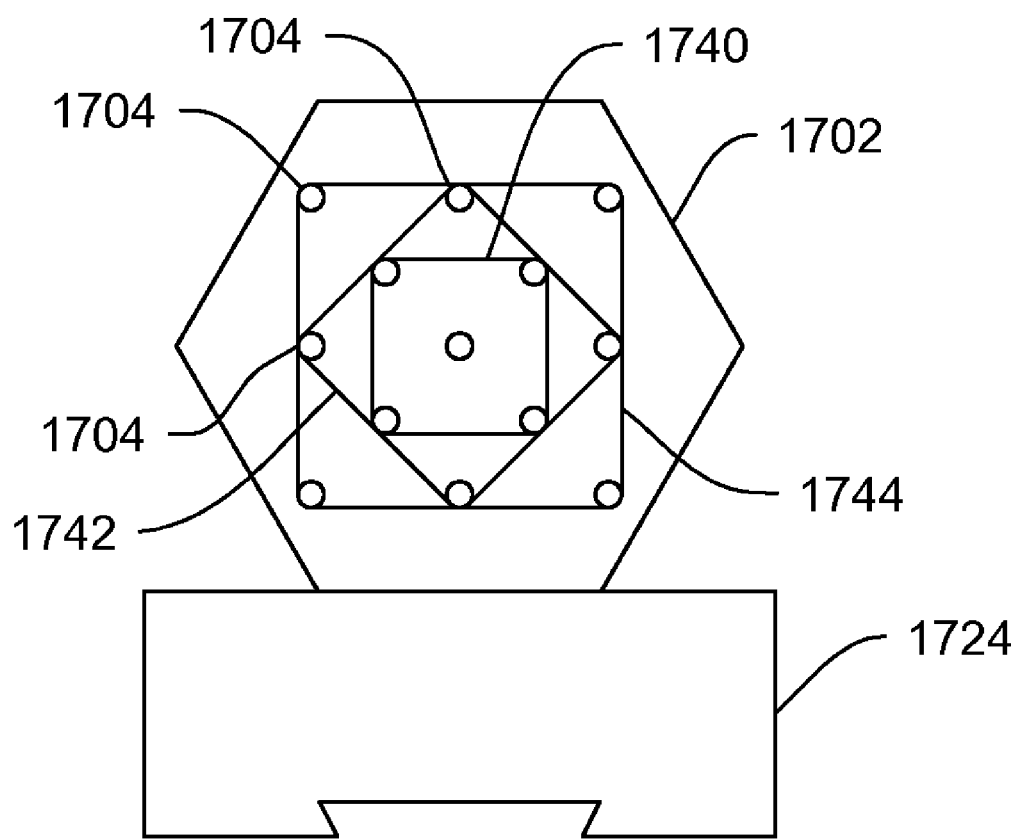
FIG. 22 is an enlarged view of an exemplary catheter, e.g., needle, guiding template for use with the delivery system of FIG. 21.

FIGS. 20-22 illustrate an exemplary system 1700 for implanting the LDR brachytherapy devices and their associated radiation sources described above to a target tissue region, e.g., the region surrounding a breast lumpectomy cavity. In the illustrated embodiment, the system includes a catheter or needle guiding template 1702 having a predetermined number and pattern (array) of openings 1704 as shown in FIG. 20. The template 1702 may form part of an adjustable catheter or needle guiding apparatus by coupling to a stereotactic table 1720, which is diagrammatically illustrated in the figures by base portion 1722, and translating portion 1724 (portions 1722 and 1724 shown exploded in FIG. 20). The stereotactic table 1720 may be coupled or attached to a patient locating or treatment surface 1730, e.g., patient table.

The template 1702 may be coupled to, or otherwise associated with, a first compression member 1726 located adjacent an opening 1732 in the treatment surface 1730. An opposing second compression member 1728 may be located on an opposite side of the opening 1732. The compression members 1726 and 1728 may be oriented about 90 degrees from a set of optional compression plates 1727 (only one plate 1727 shown).

One or both compression members 1726, 1728 may include a hole pattern similar to that of the template 1702, or may otherwise at least permit the passage of the needles/cannulae (e.g., needles 114 of FIG. 1A) as illustrated in FIG. 21.

In use, a patient may lie on the treatment surface 1730, e.g., with the patient's head located in the direction 1731, such that the breast 200 passes through the opening 1732 of the treatment surface 1730. The optional compression plates 1727 may then be used to immobilize the breast 200.

Once the breast 200 is immobilized, the stereotactic table 1720, with the template 1702 attached, may be positioned, and the translating portion 1724 moved, until the compression members 1726 and 1728 contact the breast 200. The position of the stereotactic table 1720, and thus the needle guiding template 1702, may be aligned with the location of the target tissue region 202 via the use of various imaging techniques including, for example, X-ray, ultrasound and CT scan. In some embodiments, the template 1702 may be aligned relative to the target tissue region based upon input provided by an imaging device, e.g., a side viewing ultrasound apparatus 1739, located underneath the breast 200.

With the template 1702 aligned with the target tissue region 202 and positioned against the breast 200, one or more needles 114 may be inserted into the openings 1704. In the treatment of breast lesions, the needles 114 may be inserted completely through the breast 200 as illustrated in FIG. 21. Alternatively, and in the treatment of other cancers, the length of each needle 114 may be varied to ensure the correct depth penetration at each opening 1704, or the insertion depth of each needle 114 may simply be varied.

Certain embodiments of the system 1700 may optionally include an adhesive bandage member 1750 associated with the first compression member 1726, and/or an adhesive bandage member 1752 associated with the second compression member 1728. As shown, the bandage members 1750 and 1752 are located between the respective compression members and the breast 200. The bandage members 1750 and 1752 may have adhesive on each side, e.g., a first side 1754 and a second side 1756, and include openings (not shown) that correspond generally to the openings 1704 of the template 1702. Alternatively, the bandage members 1750 and 1752 may be punctured by the needles 114 during needle insertion. When the compression members 1726 and 1728 are pressed against the breast 200, the bandage members 1750 and 1752 may adhere to the breast 200 and provide a dressing for the punctures created by the needles 114.

Once the needles 114 are inserted, the brachytherapy devices described herein, e.g., devices 102 or 602, may be inserted, and the needles 114 removed, in accordance with various methods as described and illustrated herein. For example, the brachytherapy devices 102 (or devices 602) may be inserted and the needles 114 (or the cannulae 630) removed in accordance with the methods described herein and illustrated in FIGS. 2A-2E and 2F (or 8A-8E).

With the needles 114 removed, the template 1702 and contact plates 1726 and 1728 may be withdrawn from the breast 200, leaving the bandage members 1750 and 1752 adhered to the breast by their respective first adhesive sides 1754. The tail portions 106 may then be anchored, e.g., by using locking members such as members 120 illustrated in FIGS. 2E and 27.

A liner (not shown) may then be removed from the respective second adhesive side 1756 of each bandage member 1750 and 1752. Once the second adhesive side 1756 is exposed, the flexible tail portions 106 may be folded against the second adhesive side, where they adhere thereto. A second, single-sided adhesive member (not shown) may be placed over each bandage member 1750 and 1752 to secure the tail portions and cover any exposed adhesive on the second adhesive side 1756. As a result, the flexible tail portions may be folded against the contours of the breast and secured.

In some embodiments, the openings 1704 of the template 1702 may be grouped according to a particular target tissue volume, e.g., lesion size, as shown in FIG. 22. For example, a small square, five-opening pattern 1740 may be utilized for small target tissue regions (e.g., those regions up to about 1 centimeter in diameter), while a larger nine-opening pattern 1742 may be utilized for larger target tissue regions (e.g., those regions up to about 2 cm in diameter). A still larger, thirteen-opening pattern may be utilized for even larger target tissue regions (e.g., those regions up to about 3 cm in diameter).

By aligning the center opening of the template 1702 with the center of the target tissue region, the template may indicate a standard number of seeds, e.g., a particular number of therapy devices 102, based upon the predetermined target volume. This could simplify, or possibly eliminate, the need for complex dose mapping calculations commonly associated with conventional brachytherapy methods.

It is noted that the patterns 1740, 1742, and 1744 are exemplary only. In other embodiments, the patterns may include most any number of openings 1704 in most any shaped pattern, e.g., a circular array of 5 to 50 catheters. Moreover, the templates could accommodate more that one diameter catheter or needle (e.g., 10, 15, and 20 mm diameters). Moreover, while shown with three patterns, templates having most any number are possible.

Figure 23:
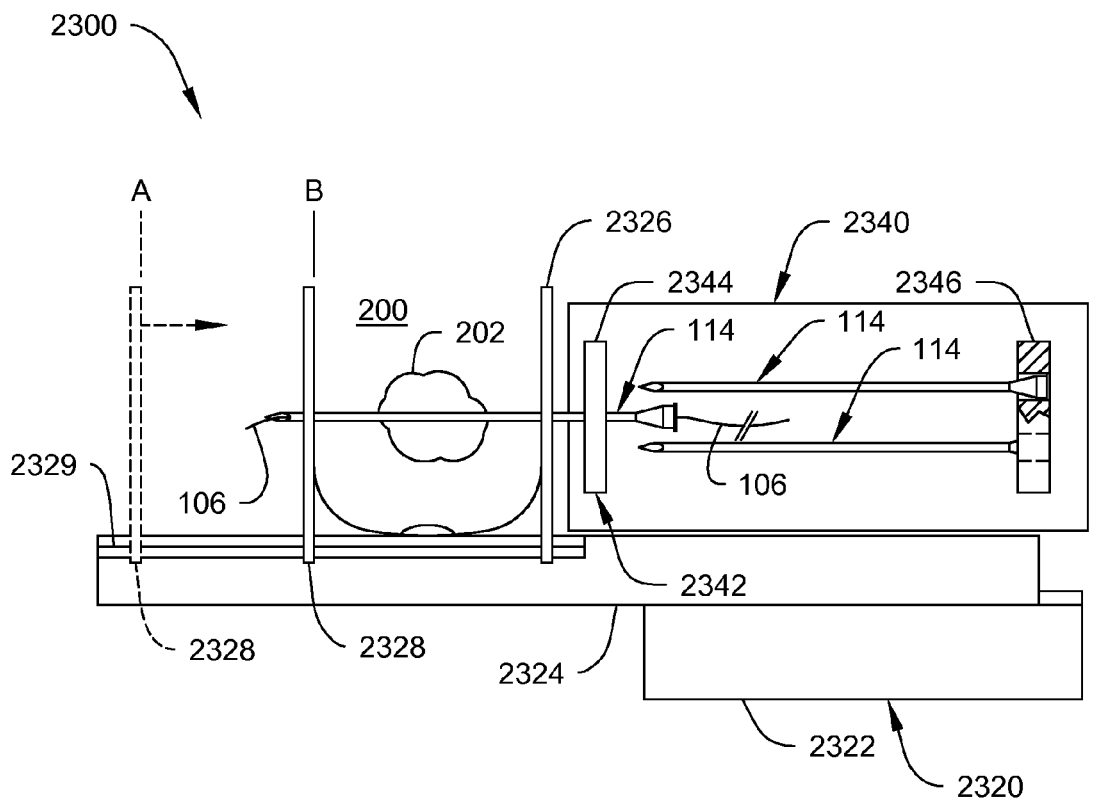
FIG. 23 is a diagrammatic view of another delivery or implantation system for use with the brachytherapy methods and apparatus described herein.
Figure 24:
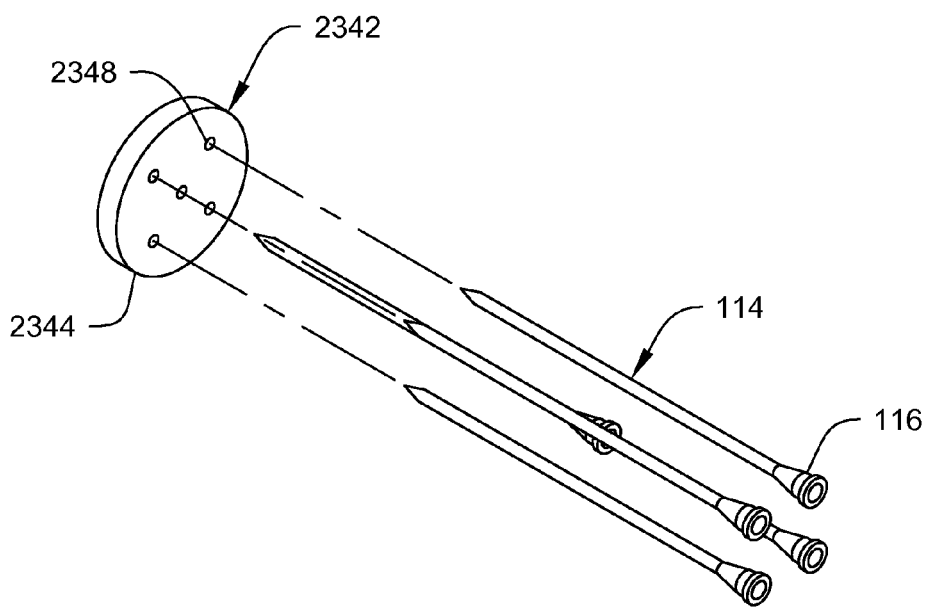
FIG. 24 is an exploded view of a portion, e.g., a cartridge, of the delivery system of FIG. 23.

FIGS. 23 and 24 illustrate another embodiment of a system for implanting brachytherapy devices. FIG. 23 illustrates a system 2300 similar in many respects to the system 1700 described above. For instance, the system 2300 may include a stereotactic table 2320 secured to treatment surface, e.g., patient table (not shown). The table 2320 may include a base portion 2322 and a translational portion 2324. The system 2300 may also include a first or proximal compression member 2326 and a second or distal compression member 2328. One or both compression members 2326 and 2328 may be movable relative to the other and/or the base portion 2322, e.g., along a slide rail 2329.

Unlike the system 1700, however, the system 2300 may also include a catheter or needle cartridge receiver 2340 operable to receive a pre-assembled needle cartridge 2342 having multiple needles 114 positioned in a predetermined array. The needle cartridge 2342 is shown in an exploded view in FIG. 24. The cartridge 2342 may include a first holder 2344 and a second holder 2346 (second holder 2346 not shown in FIG. 24). The holders 2344 and 2346 may include holes 2348 to hold and guide the multiple needles 114 in the desired predetermined array during insertion. Where needles 114 include a hub 116, the holes 2348 in the holder 2346 may be larger than the corresponding holes 2348 in the holder 2344 to permit the passage of the hub 116 (see FIG. 23).

During operation of the system 2300, the stereotactic table 2320 may be aligned as described above with respect to the system 1700. Once aligned, the breast 200 may be immobilized with the compression members 2326 and 2328. Based upon the particular volume of the target tissue region 202, a specific cartridge 2342 may be selected and pre-assembled with a corresponding number of catheters, e.g., needles 114. For instance, the cartridge in FIG. 24 is a 5 catheter configuration. However, other cartridges may utilize more or less catheters (e.g., 9 catheter and 13 catheter cartridges). The cartridge 2342, including the holders 2344 and 2346 and the catheters 114, may then be loaded into the cartridge receiver 2340. Portions of the holders 2344 and 2346 may be designed to contact one or more internal surfaces of the cartridge receiver 2340 so that the cartridge 2342 aligns with the cartridge receiver upon insertion.

Once the cartridge 2342 is loaded, each needle 114 may be independently and manually advanced through the proximal compression plate 2326 (which may include a hole pattern identical to the holder 2344), the breast 200, and the distal compression member 2328. The central needle 114 may be advanced first and its position within the target tissue region 202 confirmed (or repositioned) before the remaining needles are advanced. Brachytherapy devices, e.g., devices 102 of FIG. 1A, may then be placed into the needles 114 as described in FIGS. 2A-2E. Alternatively, the devices 102 could be pre-installed in the cartridge 2342.

With the devices 102 inserted completely, the distal tips of the tail portions, see e.g., tail portion 106 of FIG. 1A, may be temporarily secured relative to the distal compression member 2328. At this point, the needles 114 may be retracted and removed from the breast 200, and ultimately, withdrawn from the cartridge loader 2340. The proximal compression member 2326 may then be withdrawn and the proximal tail portions secured to the breast using, for example, the locking devices 120 described above and illustrated in FIGS. 2E and 27. The distal compression member 2328 may then be withdrawn and the distal tail portions secured relative to the breast 200 in a similar manner.

Figure 25A:
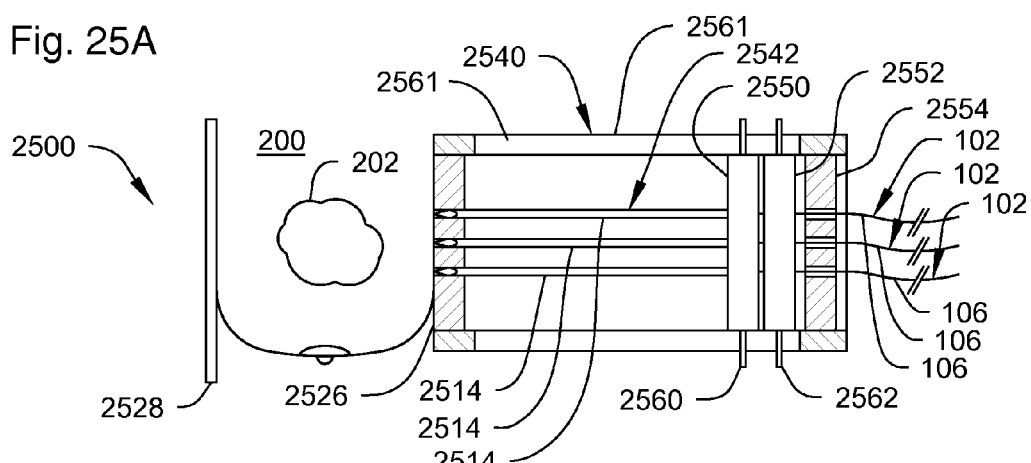
FIGS. 25A-25D are diagrammatic illustrations of a delivery or implantation system and method in accordance with yet another embodiment.

FIGS. 25A-25D illustrate yet another system and method for inserting brachytherapy devices, such as those described elsewhere herein into a target tissue region. FIG. 25A illustrates a system 2500 similar in many respects to the systems 1700 and 2300 described above. For example, the system 2500 includes a stereotactic table (not shown) having a catheter or needle cartridge receiver 2540 coupled thereto. The stereotactic table may be coupled to the treatment table (also not shown). The system 2500 may also include a catheter or needle cartridge 2542. The needle cartridge 2542 may include a series of needles 2514, e.g., 5, 9, or 13 needle array, which are generally rigidly and orthogonally mounted to a first plunger member 2550. In this embodiment, the needles 2514 may be hubless as the proximal ends of the needles 2514 are secured (e.g., press fit, staked, adhered, etc.) to the first plunger member 2550.

The cartridge 2542 may also include a first or proximal compression member 2526 (which may form the needle guiding template) as well as a second plunger member 2552 and an optional backing plate 2554. In other embodiments, the backing plate 2554 may be part of the cartridge receiver 2540. As with the systems previously described herein, the system 2500 may also include a second or distal compression member 2528 to assist in immobilizing the breast 200.

During operation, the stereotactic table may be aligned such that the center of the needle cartridge receiver 2540 is centered relative to the target tissue region 202. The cartridge 2542 may then be loaded into the cartridge receiver 2540, and the breast immobilized by the first and second compression members 2526 and 2528. The brachytherapy devices, e.g., devices 102 of FIG. 1A, may have been previously loaded into the needles 2514 of the cartridge 2542. The first plunger member 2550 may then be advanced toward the breast 200. Because the needles 2514 are rigidly coupled to the first plunger member 2550, the needles 2514 advance simultaneously into the target tissue region of the breast 200 in the pre-determined parallel array. The first plunger member 2550 may include a tab 2560 that rides along a slot or surface 2561 of the cartridge receiver 2540 so that the first plunger member 2550 may be manually or automatically advanced from outside the cartridge.

Figure 25B:
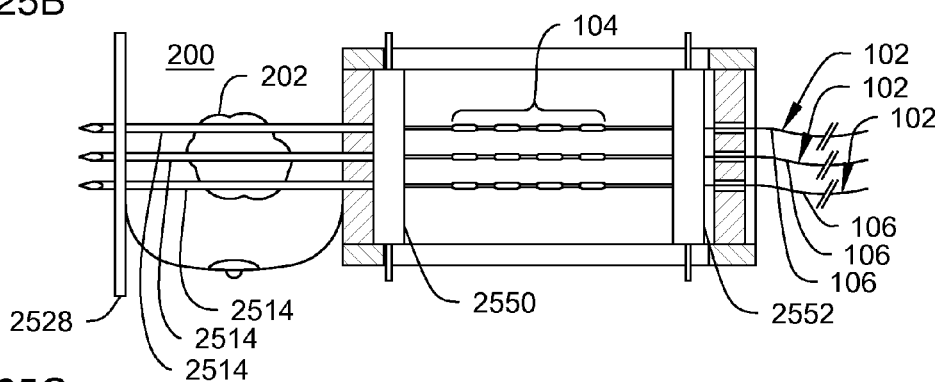
Figure 25C:
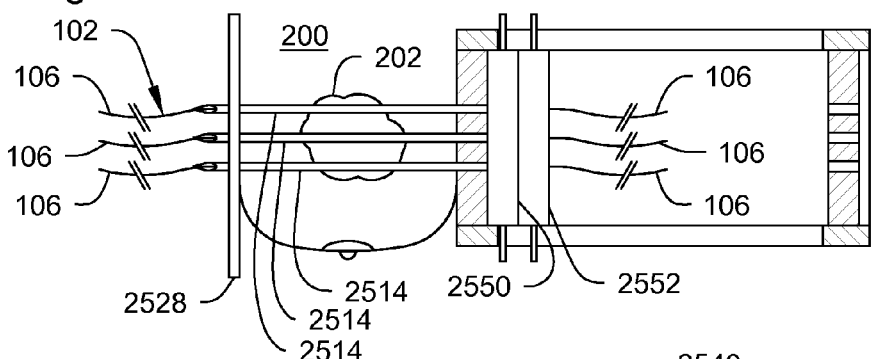

After the first plunger member 2550 has been fully advanced as shown in FIG. 25B, the second plunger member 2552 may be advanced toward the breast 200. The second plunger member 2552 has the proximal tail portions 106 of the brachytherapy devices 102 releasably secured thereto. Thus, advancing the second plunger member 2552 may advance one or more of the brachytherapy devices 102 into place such that the distal tail portions 106 emerge from the distal ends of the needles 2514 as shown in FIG. 25C.

Figure 25D:
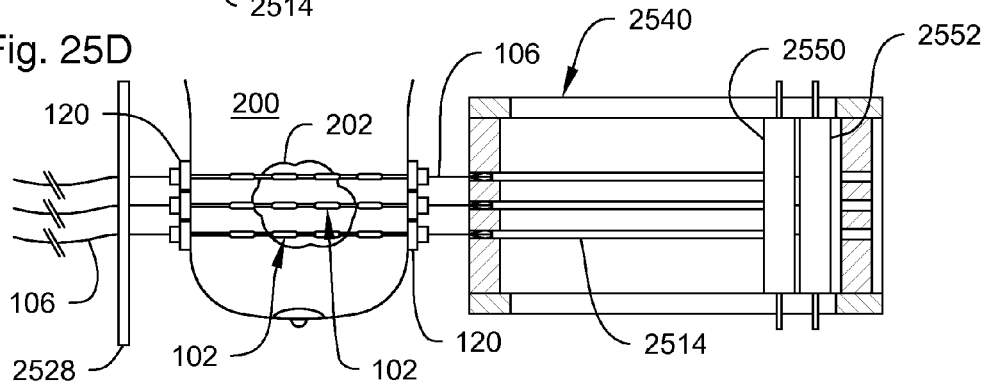

The distal tail portions 106 may temporarily be secured to the distal compression member 2528 to hold the brachytherapy devices 102 in place. Once the distal tail portions 106 are secured, the proximal tail portions 106 may be released from the second plunger member 2552 and the first and second plunger members 2550 and 2552 may be retracted as shown in FIG. 25D. The cartridge receiver 2540 may also be retracted so that the proximal tail portions 106 may be secured in accordance with methods already described herein (e.g., locking members 120). The distal tail portions 106 may then be disconnected from the distal compression member 2528 and the latter withdrawn. The distal tail portions 106 may then be secured relative to the breast 200.

Thus, the system 2500 provide an apparatus for simultaneously implanting, in a two dimensional array, multiple brachytherapy devices into the body. Moreover, the systems described herein allow simultaneously advancing a two-dimensional array of catheters into a target tissue region, and then delivering or implanting one or more radiation sources through at least one of the catheters of the array. Once the radiation sources are implanted, sequential or simultaneous removal of the catheters of the array of catheters from the target tissue region may be accomplished.

Figure 26:
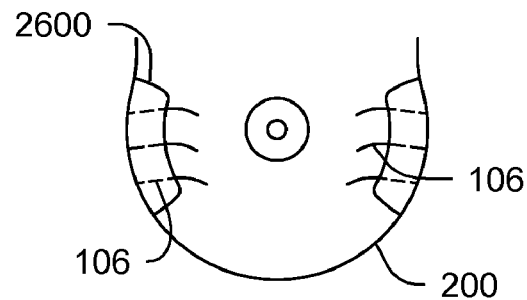
FIG. 26 is a view of a portion of a human body, e.g., a female breast, after the brachytherapy devices as described herein have been implanted and secured.

As already described above, some embodiments may permit the tail portions 106 to be secured to the breast using an adhesive pad or bandage 2600 as illustrated in FIG. 26. Here, the bandage may be used in conjunction with, or as an alternative to, the locking members 120.

To assist the health-care provider in securing the distal and/or proximal tail portions 106, the compression members 2526, 2528 may be configured as generally illustrated in FIG. 27. That is, openings 2570 in the plate (e.g., plate 2528) through which the tail portions 106 pass may include a recess 2572 that holds the locking member 120 against the skin. As a result, when the compression plate 2528 is withdrawn, the locking member 120 may already be threaded over the tail portion 106. The health care provider may then quickly crimp the locking member 120, e.g., along a deformable portion 2576.

Figure 28A:
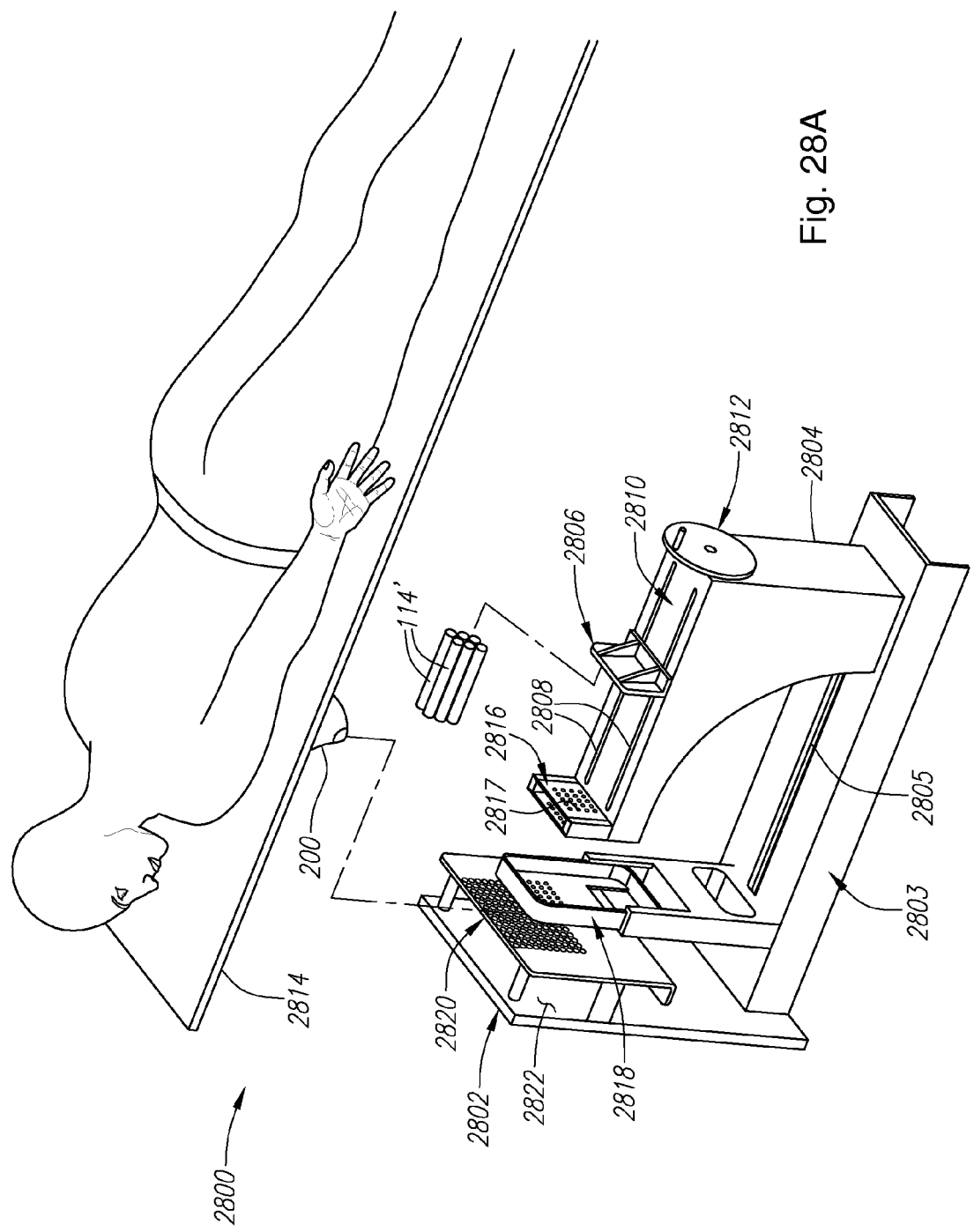
FIG. 28A is a perspective view of a delivery or implantation system in accordance with yet another embodiment, the system for use with brachytherapy apparatus and methods described herein, e.g., the method of FIGS. 2G-2L.

FIG. 28A illustrates a system and method for inserting brachytherapy devices into the body in accordance with yet another embodiment. The system 2800 is similar in many respects to the systems 1700, 2300, and 2500 already described above. For example, the system 2800 may include a stereotactic positioning apparatus 2802 having a fixed base 2803 and a movable arm 2804 slidably attached thereto. The movable arm 2804 may move along one or more rails 2805 formed in the fixed base 2803. A needle driver or driver plate 2806 may be coupled to the movable arm 2804 via slots 2808 provided along an upper surface 2810. A screw mechanism, driven by a rotating wheel 2812 or the like, may be provided to displace the driver plate 2806 along the slots 2808. The rotating wheel 2812 provides a method for moving the needle driver in a uniform manner while providing adequate tactile feedback to the physician. Alternate methods of driving and retracting the array of needles may be employed. For example, a lever-operated rack and pinion apparatus (not shown) could offer the desired characteristics, i.e., controlled movement of the needles to and from the target tissue, while maintaining an acceptable degree of tactile feedback.

An array of needles 114' may be displaced by the driver plate 2806 under control of the wheel 2812. As with the needle cartridge 2542, the needle cartridge used herein may include the array of needles 114' (see also FIG. 1B), which are generally orthogonally positioned relative to the driver plate 2806. The number and position of the array of needles 114' may be predetermined based upon particular dose mapping calculations. The needles 114' may be hubless (i.e., exclude the hub 116 shown in FIG. 1B) as the proximal ends may be secured (e.g., press fit, staked, adhered, abutted, etc.) to the driver plate 2806. In other embodiments, the needles 114' may include a hub such that they resemble the needles 114 of FIG. 1A.

The stereotactic positioning apparatus 2802 may be located proximate a table 2814 upon which a patient may be accommodated in a face-down position. For treatment of the breast, the stereotactic table 2814 may include an opening through which the breast 200 may protrude. The stereotactic positioning apparatus 2802 may be positioned such that the breast 200 is located between a first or proximal compression member 2818 and a second or distal compression member 2820. The compression members 2818 and 2820 may clamp against the breast to immobilize it prior to implantation. The distal compression member 2818 may also include an array of openings that corresponds to the array of needles.

The apparatus 2802 may further include a needle guide 2816 positioned between the driver plate 2806 and the proximal compression member 2818. The needle guide may include an array of guide openings 2817 that correspond in position to the array of needles 114' (i.e., there is an opening 2817 aligned with each needle 114'). The needle guide 2816 may support and guide the needles 114' during the implantation process.

In some embodiments, the needle guide 2816 comprises two spaced-apart templates having the series of aligned openings 2817. The array of needles 114' may be assembled into the openings 2817 prior to or after the needle guide is secured to the arm 2804. The driver plate 2806 may then be used to push against the free proximal end of the needles 114' to drive the same through the breast.

The proximal and distal compression members 2818 and 2820 may also include an array of openings that correspond in location to the array of needles 114'. Such a configuration may assist with confirming that the needles did not wander or excessively deflect within the body. Alternatively, the proximal and distal compression members 2818 and 2820 may simply include a large opening in place of the array of openings. Such a larger opening could be covered with, for example, a membrane (not shown) that may be penetrated by the needles 114'. Such a membrane could be configured to remain in place during implantation, e.g., could function as a dressing or bandage. The apparatus 2802 may further include imaging equipment, e.g., image receptor 2822, to allow imaging of the breast before, during, or after implantation.

During operation of the system 2800, the stereotactic table 2814 may be aligned relative to the positioning apparatus 2802 such that the compression members 2818, 2820 and the needle guide 2816 (and thus the array of needles 114') are accurately positioned relative to the target tissue region of the breast 200. The breast may then be immobilized between the proximal and distal compression members 2818 and 2820 by moving the movable arm 2804 relative to the fixed base 2803. Each needle 114' (which may be preloaded with a brachytherapy device, e.g., the device 562 of FIG. 1B), may then be secured to the driver plate 2806 or, alternatively, to the needle guide 2816.

The driver plate 2806 may be advanced towards the needle guide 2816 whereby the needles 114' pass through the guide openings 2817 in the guide and towards the proximal compression member 2818. The needles 114' may advance simultaneously through the array of openings in the needle guide 2816, through the proximal compression member 2818, and through the target tissue region of the breast 200 in the predetermined array formation. Further advancement results in the needles 114' passing completely through the breast and, finally, the distal compression member 2820.

The face of the driver plate 2806 that contacts the proximal ends of the needles 114' is illustrated in FIG. 28A as a generally flat surface. However, this surface could also be staggered (e.g., stepped) from row to row. For example, each row may be recessed by about 5 mm from the row below it. When the face of the driver plate 2806 is so staggered, the needles 114' will be simultaneously advanced through the tissue in a correspondingly staggered fashion as well. This stair-step advancement enables the peak force necessary during implantation (typically during skin penetration) to be reduced, as the various rows of needles will penetrate the region of high resistance (e.g., the skin) at slightly different times during needle advancement.

Although described as a row-by-row variation, any one of a variety of offset patterns could be utilized (e.g., row-to-row variation, column-to-column variation, concentric ring (of a circular array) variation, etc.). In any case, the total load to the patient, and to the apparatus, may be reduced by staggering the leading ends of the needles as they advance. The staggered shape of the driver plate face 2806 could be integrated into the driver plate, or could be a separate piece or pieces that are placed relative to the driver plate face to create the desired staggered configuration.

Once the needles 114' have passed through the breast 200, the brachytherapy devices, e.g., devices 562, may be advanced out of the distal ends of the needles in a manner similar to that illustrated in FIG. 21 (e.g., the devices may be simultaneously advanced from their respective proximal ends). The devices may then be immobilized at their distal tails and the needles withdrawn as indicated in FIGS. 2J and 2K. Fine adjustment of the brachytherapy devices may then be made utilizing most any acceptable method, e.g., X-ray, CT scan.

Figure 28B:
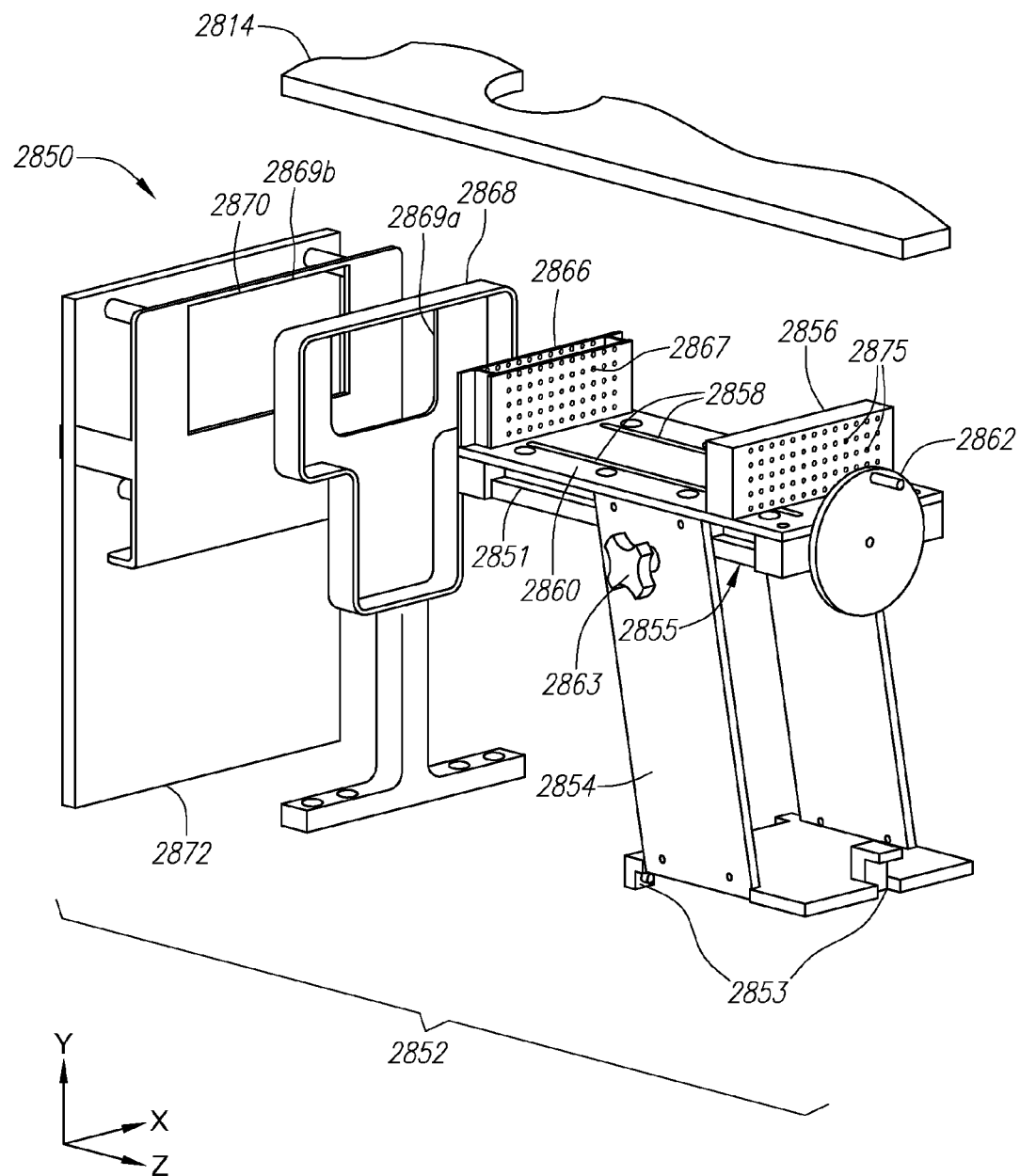
Figure 28C:
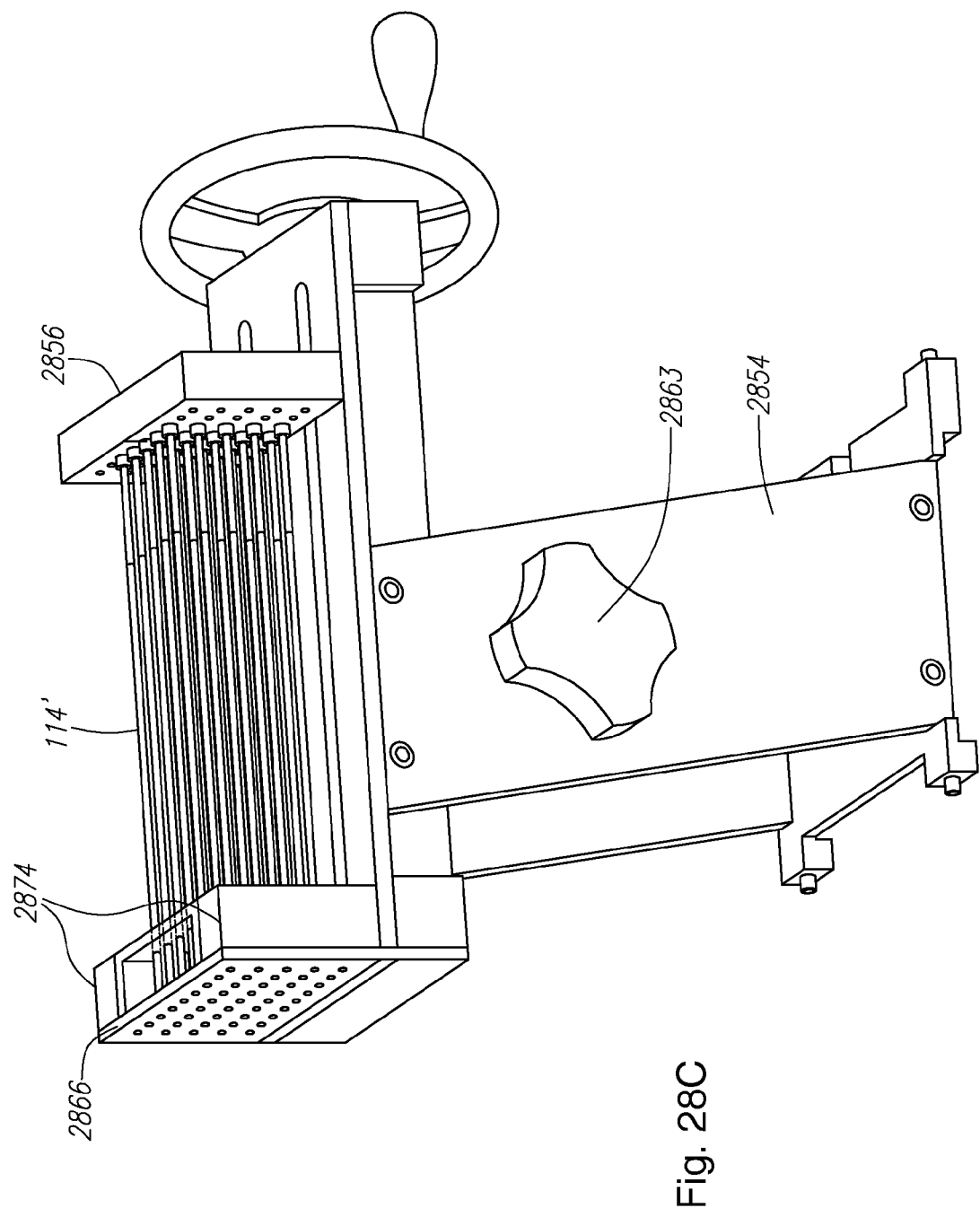
Figure 28D:
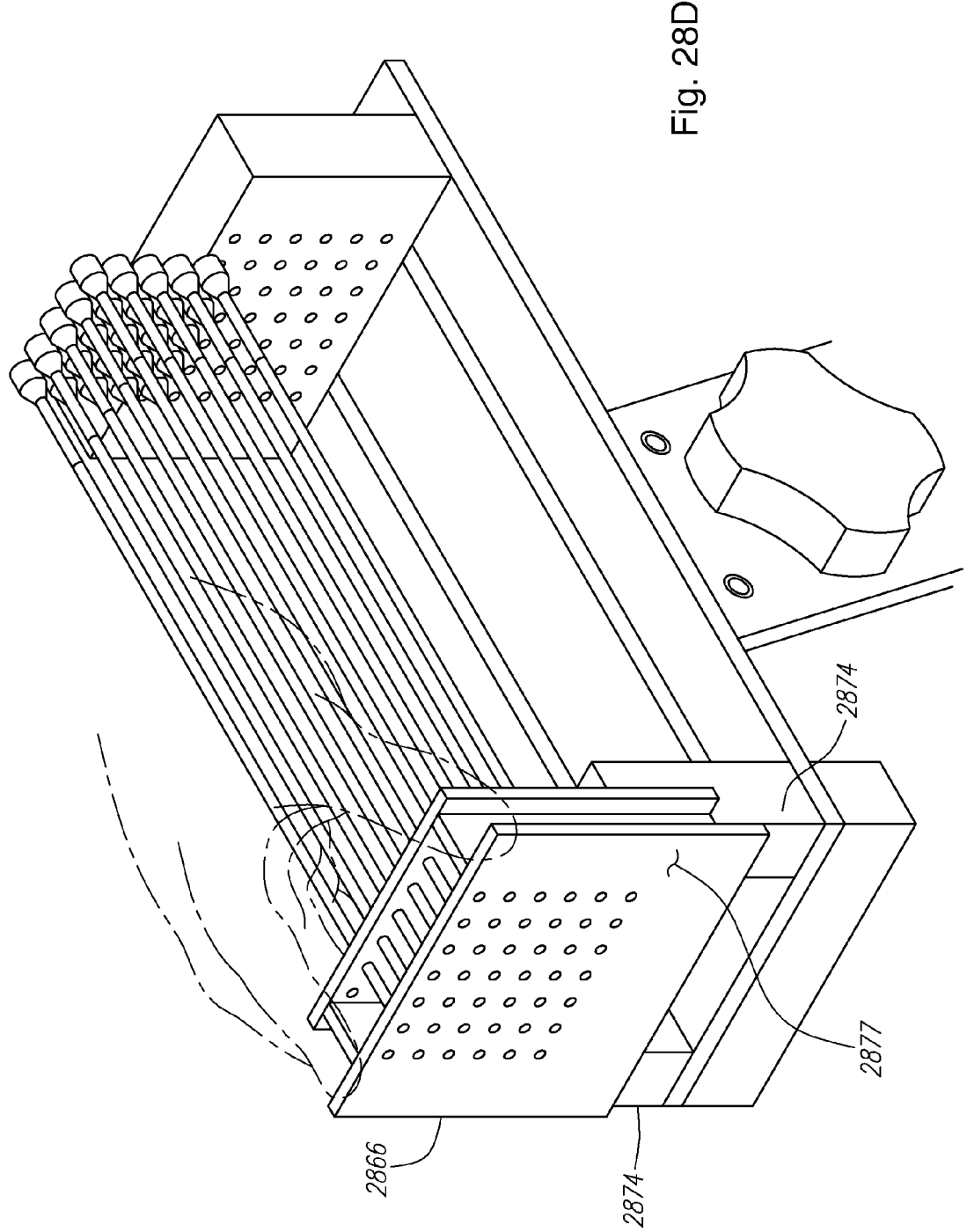

FIGS. 28B-28D illustrates a system 2850 and method for inserting brachytherapy devices into the body in accordance with still yet another embodiment. The system 2850 is similar in many respects to the system 2800 already described above. For example, the system 2850 may include a driver and positioning apparatus 2852. In one embodiment, the components of the apparatus 2852 could be attached to a stereotactic breast biopsy table (e.g., such as those available from Fischer Imaging Corp. of Denver, Colo., USA). For example, the apparatus 2852 may include an upwardly extending arm 2854 having flange portions 2853 that permit attachment directly to the stereotactic table. Alternatively, the components of the apparatus 2852 may be secured to a fixed base member (e.g., for other imaging modalities such as CT). While shown as rigidly attached, the arm may, in other embodiments, be slidably attached to such a fixed base member.

The arm 2854 may support a platform 2855 having a needle driver or driver plate 2856 that may move along an upper surface 2860 of the platform. A mechanism, e.g., rotating wheel 2862 or the like, may be provided to displace the needle driver plate 2856 via a lead screw that is connected to a portion of the driver plate extending through one or more slots 2858 formed in the surface 2860. The rotating wheel 2862 provides a method for moving the needle driver in a uniform manner while providing adequate tactile feedback to the physician, as well as providing desirable mechanical advantage for driving simultaneously multiple needles through tissue. The platform 2855 itself may be movable (e.g., slidable within one or more channels 2857), relative to the arm 2854, with the use of a clamp, e.g., screw clamp 2863, or cam-operated clamp.

The stereotactic positioning apparatus 2852 may be located proximate the table 2814 in a manner similar to that illustrated in FIG. 28A. The driver and positioning apparatus 2852 may be positioned such that the breast 200 is located between a first or proximal compression member 2868 and a second or distal compression member 2870 (which is illustrated attached to an image receptor 2872). The compression members 2868 and 2870 may clamp against the breast to immobilize it prior to implantation. The proximal and distal compression members 2868 and 2870 may also contain large openings 2869a and 2869b, respectively, or smaller openings that approach the size of the thru-holes in the compression member 2870 of FIG. 28B. The openings may be covered with a thin membrane of polyester film, paper, spun-bound polyolefin, or the like. The membrane may have an adhesive on at least one side to allow adherence to the compression members. The membrane may include a foam backing on the non-adherent side as well, such as a Mammopad brand breast cushion available from Biolucent, Inc., of Aliso Viejo, Calif., USA. The foam backing may provide comfort to the patient as the breast is compressed, and also aid in securing the brachytherapy devices by providing residual axial tension to the devices as they reside within the breast.

Like the apparatus 2802, the apparatus 2852 may further include a needle guide 2866 positioned between the driver 2856 and the proximal compression member 2868. The needle guide may include two spaced-apart plates that each incorporate an array of aligned guide openings 2867 that correspond in position to the array of needles that are to be implanted (i.e., there is an opening 2867 aligned with each needle). The needle guide 2866 may support and guide the needles 114' during the implantation process. The array of needles may be assembled into the openings 2867 prior to or after the needle guide is secured to the arm 2854. In some embodiments, the needles, e.g., with brachytherapy devices (e.g., devices 562 of FIG. 1B) contained therein, may be inserted into the openings 2867 of the needle guide 2866 prior to attachment of the needle guide to the arm 2854. The needle guide 2866 may be attachable to the arm 2854 in most any manner. For example, it may rest or fasten against posts 2874 attached to the platform 2855 as shown in FIGS. 28C and 28D.

During operation of the system 2850, the patient table 2814 may be aligned relative to the driver and positioning apparatus 2852 such that the compression members 2868, 2870 are accurately positioned relative to the target tissue region of the breast 200. The breast may then be immobilized between the proximal and distal compression members 2868 and 2870 by moving the proximal compression member towards the distal compression member. As described above, the openings 2869a and 2869b of the compression members may have a thin, penetrable membrane operable to adhere to compression members on one surface and to the breast on the other.

Needles, such as needles 114' (which may be preloaded with a brachytherapy device, e.g., the device 562 of FIG. 1B), may be inserted into the needle guide 2866 and the needle guide attached to the platform 2855 as shown in FIGS. 28C and 28D.

The platform 2855 may be advanced along the channel 2857 relative to the arm 2854 until the needle guide 2866 is proximate the breast tissue constrained by the proximal compression paddle 2868. Tightening of the screw clamp 2863 may secure the platform in the desired position relative to the arm 2854.

The driver plate 2856 may then be advanced towards the needle guide 2866 via the wheel 2862 until a face of the driver plate contacts the proximal end of the needles (e.g., contacts the hub 116' of FIG. 1B) as shown in FIG. 28C. As this occurs, the proximal tail portions (see tail portion 566 in FIG. 2G) of the brachytherapy devices 562 may pass through openings 2875 formed in the driver plate 2856. The openings 2875 may be funnel-shaped to aid in passage of proximal tail portions of the brachytherapy devices through the driver plate 2856. Continued movement of the wheel 2862 causes the needles 114' to pass completely through the breast 200 and the membranes attached to each compression member 2868 and 2870. Once the needles 114' have passed through the breast 200, the brachytherapy devices, e.g., devices 562, may be advanced out of the distal ends of the needles in a manner similar to that illustrated in FIG. 21 (e.g., the devices may be simultaneously advanced from their respective proximal ends). The devices may then be immobilized at their distal tails and the needles withdrawn as indicated in FIGS. 2J and 2K.

As with the driver plate 2806 described above, the driver plate 2856 may be stepped, e.g., form a stair step profile when viewed from one side. As a result, the tips of the needles may be staggered such that a first subset of needles may puncture the breast, then a second subset, followed by a third subset, etc.

Needle withdrawal may also be accomplished by retracting the needle guide from the breast. To release the needle guide, the screw clamp 2863 may be loosened and the platform 2855 retracted along the channel 2857. As the platform is retracted, the needle guide 2866 may move away from the first compression member 2868. If desired, the entire driver assembly may be removed to permit full retraction of the needle guide. Eventually, the needle guide 2866 will abut the hubs (see hubs 116' in FIG. 1B) such that further movement of the needle guide causes withdrawal of the needles. Fine adjustment of the brachytherapy devices may then be made by applying traction on the brachytherapy device in the proper direction, as guided by most any acceptable visualization method, e.g., X-ray, CT scan.

In an alternative embodiment, the needle guide 2866 could be detached from the platform 2855 where it is then held stationary while the platform is retracted. The physician could then withdraw the needle guide and, simultaneously, the accompanying needles, by hand. In this embodiment, the needle guide 2866 could be attached to the platform such that it may load axially (e.g., from the direction of the compression members) with the platform. For example, the needle guide 2866 could attach to a face 2877 (see FIG. 28D) of the post 2874 (e.g., via a dowel pin or fastener). Detachment of the needle guide could then occur mainly via axial separation of the platform from the needle guide.

To assist the physician in securing the distal and/or proximal tail portions 156 (see FIG. 2L) the distal compression member 2870 may contain an array of buttons or grommets that are pre-loaded into the holes of a distal compression template, as shown and described with reference to FIG. 27.

Figure 29:
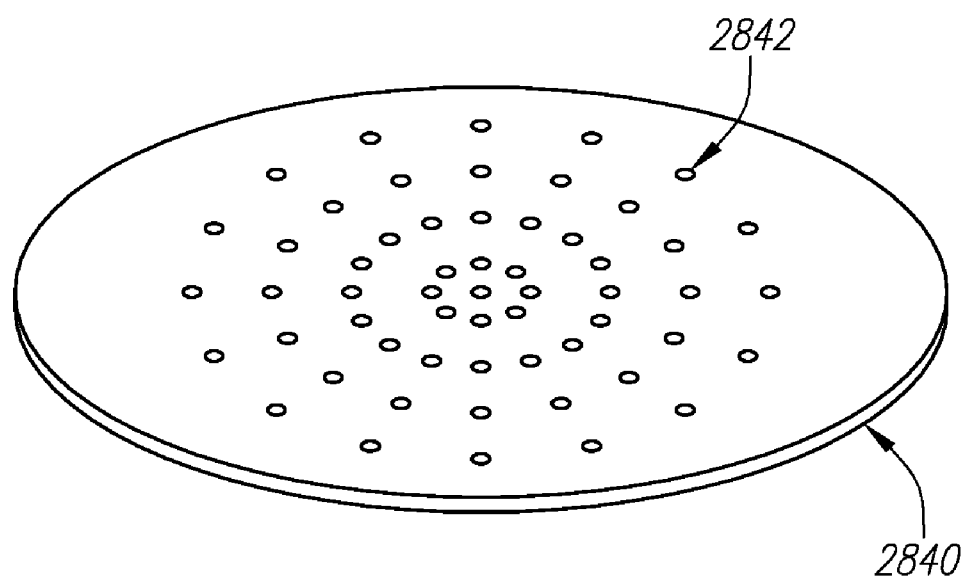
Figure 30:
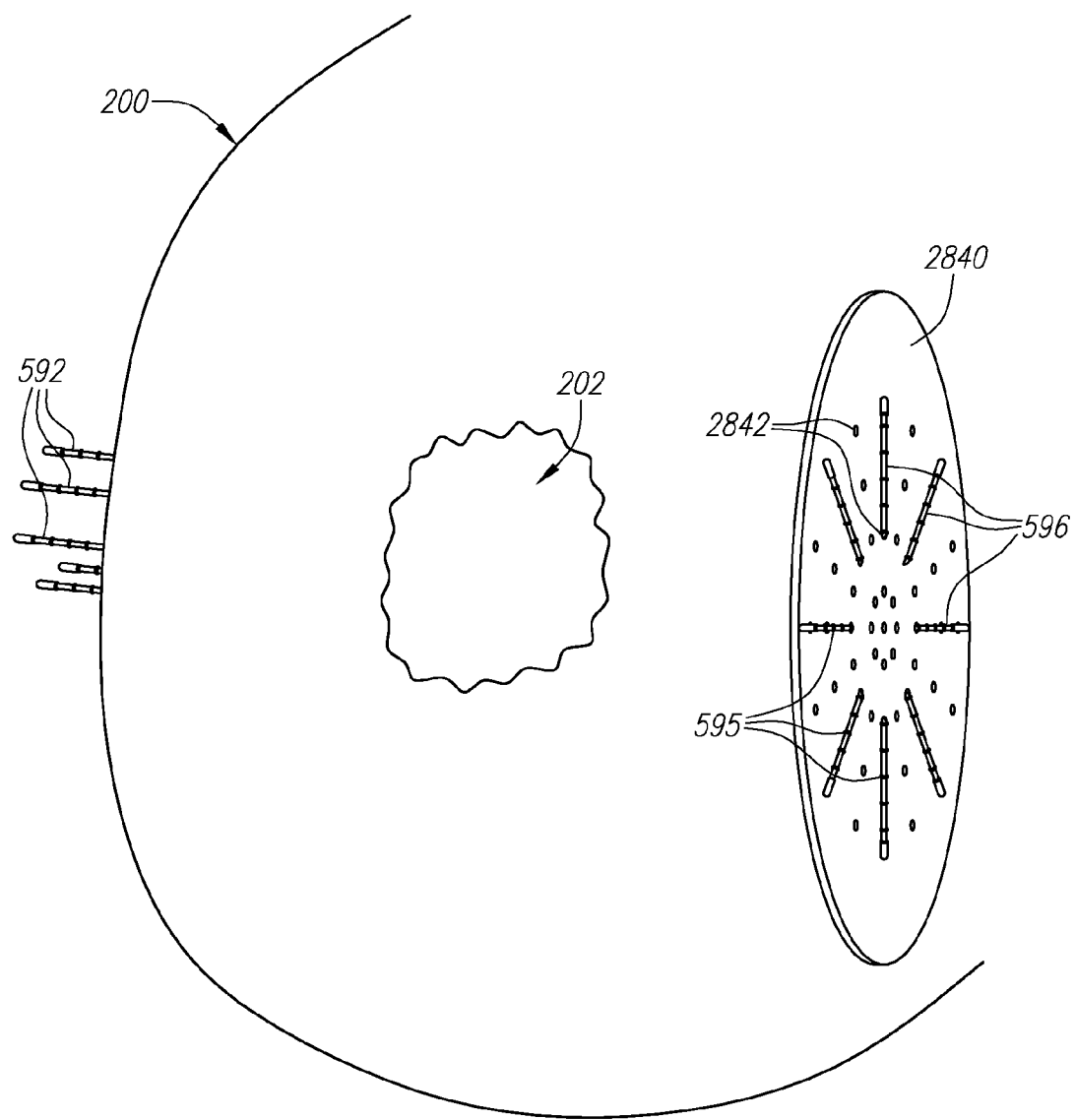
Figure 31:
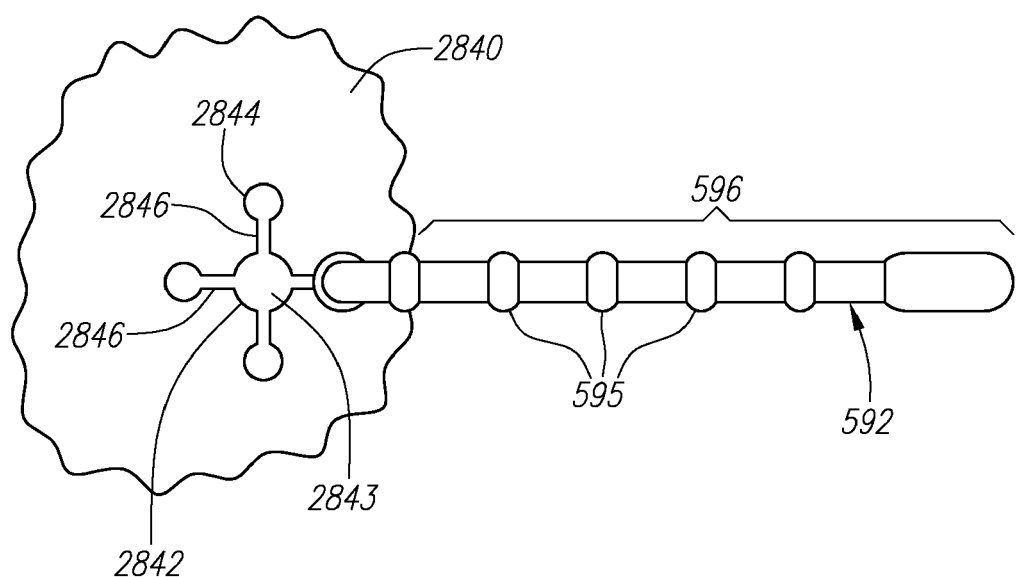

FIGS. 29-31 illustrate an exemplary anchoring tab that may be used to secure brachytherapy devices in accordance with the embodiments described herein. For example, an anchoring tab 2840 shown in FIG. 29 may be used to secure the tail portions of brachytherapy devices described herein without the need for locking members 120 or the like. Alternatively, the anchoring tab could be used in place of the penetrable membranes described above. The anchoring tab also serves to preserve the spacing of the puncture sites thereby preserving the spacing of the brachytherapy elements as they exit the skin.

The anchoring tab 2840 may include an array of preformed openings 2842 that correspond in location to the array of needles 114' (see FIGS. 28A, 28C) and through which the needles may pass. This array can be a radial pattern as shown in FIG. 29, or can also be a rectilinear array of holes (rows and columns, not shown) with, for example, 1 cm spacing between adjacent rows and columns. One side of the tab 2840 may incorporate an adhesive to permit it to adhere to one or both of the first compression member 2818 or the second compression member 2820 such that it is positioned between a respective compression member and the breast during implantation. Alternatively, the tab 2840 may have no preformed openings, but could be made to be penetrated by the needle tips. Such a tab could be made of an elastomer such as silicone, or a thermoplastic elastomer (e.g., Kraton®). Accordingly, the tab could be penetrable by the needles, while also providing some residual retentive force on the tails of the brachytherapy device once implanted. The tabs could thus aid in preserving the axial position of the brachytherapy devices.

FIG. 30 illustrates an enlarged view of brachytherapy treatment devices implanted within the body, e.g., breast 200, and secured, on one side, with the anchoring tab 2840. As clearly evident in this view, the openings 2842 of the anchoring tab 2840 may be configured to secure tail portions of brachytherapy devices incorporating anchoring ribs on their tail portions. For example, the anchoring tab 2840 may be used with the devices 592 of FIGS. 5H-5J, which, as described above, incorporate tail portions 596 having anchoring ribs 595 thereon.

FIG. 31 illustrates an exemplary opening 2842 in the tab 2840 with the tail portion 596 of the device 592 secured therein. Each opening 2842 may include a clearance portion or opening 2843, and an interference portion or opening 2844. Each clearance opening 2843 may have a diameter equal to or larger than an undeflected diameter of the anchoring rib to permit the passage of the anchoring rib 595 with clearance, while the interference openings 2844 may have a diameter smaller than an undeflected diameter of the anchoring rib. Multiple interference openings 2844 may be provided to allow various positions of the tail portion 596 relative to the clearance opening 2843. A slot 2846 may connect the clearance portion or opening 2842 to each of its interference portions or openings 2844. The slot may be sized to accommodate with clearance, or a slight interference, the section of the tail portion 596 between the anchoring ribs 595.

In use, the brachytherapy devices, e.g., devices 592, may be inserted into the breast 200 in accordance with any of the embodiments already described herein. Once each device 592 is correctly positioned, the tail portion 596 may be manipulated to displace the device from the clearance opening 2843, through the appropriate slot 2846, and into the interference opening 2844. Once the tail portions 596 are secured in this manner, they may be folded against the template as shown in FIG. 30 and secured, e.g., taped.

The choice of which of the multiple ribs are engaged in the slot 2846 would be dependent on many variables, including the thickness of the breast, the degree of post-procedural swelling of the breast, and also the desired amount of residual tension to impart on the brachytherapy source. As with the penetrable membrane on the compression paddle described earlier, the anchoring tab 2840 may contain a compressible foam layer to provide residual tension on the brachytherapy device. This layer would help keep the brachytherapy device in its proper position during positional changes of the breast in the normal course of daily activity of the patient. The change in position of the breast during normal movement can be minimized with the use of an external support device as well (described earlier herein), such a support device could include radiation attenuating material in it, as well as provide structure to minimize breast movement. By minimizing positional changes of the breast, the brachytherapy devices are less likely to deviate from their intended location during the course of implantation.

In some embodiments, the tab 2840 may be made from an adhesive backed polyester or polyolefin film. For example, the tab 2840 may be constructed to have sufficient structural integrity around the openings 2842 to prevent tear-out of the device during the implantation period. However, the template may also benefit from being somewhat flexible so that it may conform to the contours of the body, e.g., breast, during implantation to reduce discomfort.

The brachytherapy devices described herein may be implanted into (and/or around) the tumor prior to surgical excision (neoadjuvantly), and then subsequently removed before or at the time of surgery. For example, such treatments may shrink or even destroy the tumor. In other embodiments, the apparatus and methods described herein may be used to deliver brachytherapy after surgical removal of the tumor tissue to treat surrounding tissue post-operatively (post-lumpectomy in breast). In some instances, it is contemplated that brachytherapy apparatus and methods described and illustrated herein may supplement or reduce the need for conventional treatment options, e.g., tumor excision, full field external beam radiation therapy (EBRT), and chemotherapy. Alternatively, the methods described herein may be performed adjuvantly with these and other treatments, e.g., with chemo, EBRT.

It is also contemplated that the brachytherapy devices described herein could be utilized in conjunction with conventional HDR catheters. For example, HDR catheters may be implanted in accordance with conventional methods. Thereafter, in place of the HDR source, the devices described herein, e.g., brachytherapy devices 102, 402, 502, 562, etc., may be inserted into the HDR catheters and secured in place for a predetermined period of time.

Treatment in accordance with the apparatus and methods described herein may also avoid some of the disadvantages of HDR treatment, e.g., high activity, exposure of unintended tissue, potentially bulky and protruding catheters, and the need for numerous patient visits to receive treatment.

The brachytherapy devices described herein are also substantially flexible, in comparison to conventional HDR catheters, such that they may be placed in either a straight or curvilinear (e.g., curved or spiral) fashion. Such flexibility may permit implantation of radiation sources (e.g., seeds) in configurations and locations that otherwise may be considered inaccessible.

The apparatus and methods described herein may also potentially achieve desired dosage with relatively few catheters. For example, the apparatus and methods described herein may potentially obtain desired dose delivery levels with fewer catheters per target than is typically utilized with conventional HDR methods. Yet, the devices described herein may still be implanted with the use of conventional imaging methods (e.g. stereotactic X-ray, ultrasound, CT).

The apparatus and methods described herein may also provide other benefits to the patient. For example, potentially less skin damage and discomfort may result from smaller and more flexible catheter insertions. Further, the small flexible tail portions, once in their proper position, may be trimmed short, or may also be folded and taped against the skin, unlike rigid HDR catheters. Thus, the patient may have less discomfort over the course of treatment and potentially improved post-procedural cosmesis. Further, for example, apparatus and techniques described herein may potentially result in reduced side effects as compared to other treatments, e.g., EBRT and chemo, and may require fewer hospital visits over the course of the treatment regimen as compared to, for example, current HDR brachytherapy.

Still further, the brachytherapy delivery systems described herein may provide a standardized dose of radiation based upon lesion size. As a result, the need for extensive dose calculating and mapping systems could potentially be reduced or eliminated with certain cancers (e.g., breast).

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein.

We claim:

1. A brachytherapy treatment device operable for implantation into a target tissue region of a body, the device comprising:
a therapy delivery portion comprising two or more radioactive sources enclosed and constrained from movement within a casing such that through holes extending through the radioactive sources are aligned with one another; and
at least one non-dissolving flexible tail portion extending from the therapy delivery portion and operable to extend outside the body after implantation of the device, the tail portion comprising a device hub with a protrusion that extends into the casing to at least partially define a lumen that extends through the tail portion and the through holes to an opening in a distal end of the casing, the lumen sized for receiving a needle therethrough.

2. The device of claim 1, wherein the casing comprises heat-shrinkable tubing.

3. The device of claim 1, wherein the casing comprises:
a first layer formed from a meltable first material capable of encapsulating the one or more radioactive sources; and
a second layer surrounding the first layer, the second layer formed from a heat-shrinkable material.

4. The device of claim 1, wherein the therapy delivery portion further comprising one or more hollow spacers provided between adjacent radioactive sources, the hollow spacers comprising through holes further defining the lumen.

5. The device of claim 1, wherein the device hub comprises a connector for engaging a cooperating connector on a needle received within the lumen to releasably engage the needle with the device hub.

6. The device of claim 1, wherein the protrusion is captured by the casing to attach the device hub to the therapy delivery portion.

7. The device of claim 6, wherein the protrusion comprises barbs for securing the device hub to the casing.

8. A brachytherapy treatment device operable for implantation into a target region of breast tissue, the device comprising:
a non-dissolving flexible tail portion comprising a hub with a protrusion;
a therapy delivery portion extending from the tail portion and comprising:
a) two or more radioactive seeds, each seed defined by a first end, a second end and a lumen spanning between the first end and the second end;
b) a hollow spacer located between the two or more radioactive seeds; and
c) a tubular casing surrounding and constraining the two or more radioactive seeds, the spacer, and the protrusion from movement such that the seeds and spacer are aligned to at least partially define a lumen extending from the tail portion through the protrusion and seed lumens to an opening in a distal end of the casing.

9. A kit for delivering brachytherapy to a target region of breast tissue, the kit comprising:
a removably implantable elongate brachytherapy device comprising:
a therapy delivery portion comprising one or more radioactive seeds, wherein each seed defines a through hole;
a casing enclosing and constraining the one or more radioactive seeds from movement; and
a device hub comprising a protrusion that extends into the casing such that a lumen is defined that extends through the device hub, the protrusion, and the through hole of each of the one or more radioactive seeds to an opening in a distal end of the casing; and
a needle removably insertable through the lumen defined by the one or more radioactive seeds, the casing, and the device hub such that a sharp tip of the needle extends beyond the distal end of the casing.

10. The kit of claim 9, further comprising an elongate removal tool selectively insertable through the lumen defined by the one or more radioactive seeds, the casing, and the device hub after removing the needle, wherein the removal tool comprises a removal tool hub selectively engageable with the device hub.

11. The kit of claim 10, wherein the removal tool comprises a lock for engaging the removal tool with the device hub.

12. The kit of claim 9, wherein the protrusion is captured by the casing.

13. The kit of claim 9, wherein the one or more radioactive seeds comprise a plurality of radioactive seeds comprising through holes, the casing enclosing the seeds such that the through holes are aligned with one another to at least partially define the lumen.

14. The kit of claim 13, wherein the therapy delivery portion further comprising one or more hollow spacers provided between adjacent radioactive seeds, the hollow spacers comprising through holes further defining the lumen.

15. The kit of claim 9, wherein the needle comprises a lock for releasably engaging the needle with the device hub.

16. The kit of claim 9, wherein the distal end of the casing is shaped to provide a smooth transition from the needle to the therapy deliver portion when the needle is inserted into the lumen.

17. A method of providing brachytherapy to a target region of breast tissue within a body, the method comprising:
inserting a needle through a lumen of an elongate brachytherapy device until a sharp tip of the needle extends beyond the device, the device comprising a therapy delivery portion having two or more radioactive sources surrounded and restrained by a tubular casing, the radioactive sources comprising through holes at least partially defining the lumen;
introducing the needle and device into the target region; and
removing the needle from the device and leaving the device implanted within the target region for a period of about four or more days.

18. The method of claim 17, further comprising removing the brachytherapy device from the target region.

19. The method of claim 17, wherein the sharp tip penetrates tissue when the needle and device are introduced into the target region.

20. The method of claim 17, wherein the tail portion comprises a device hub attached to the therapy delivery portion, and wherein inserting the needle through the elongate brachytherapy device comprises engaging a lock on the needle with the device hub.

21. The method of claim 20, further comprising disengaging the lock on the needle from the device hub before removing the needle from the device.

22. The method of claim 17, further comprising:
inserting a removal tool into the lumen of the device after leaving the device implanted within the target region; and
removing the removal tool and device from the target region.

23. The method of claim 22, wherein the tail portion comprises a device hub attached to the therapy delivery portion, wherein removing the removal tool and device comprises:

coupling the removal tool to the device hub; and
removing the removal tool, thereby removing the device from the target region.

24. A method of providing brachytherapy to a target region of breast tissue within a body, the method comprising:
   coupling an elongate brachytherapy device to a needle by inserting the needle into a lumen of the device, the device comprising:
   a therapy delivery portion comprising one or more radioactive sources; and
   a casing surrounding and restraining the one or more radioactive sources, each radioactive source comprising a through hole at least partially defining the lumen;
   inserting the needle and associated brachytherapy device into the breast tissue;
   immobilizing the brachytherapy device; and
   withdrawing the needle from the breast tissue, whereby the brachytherapy device remains implanted.

25. The method of claim 24, wherein inserting the needle and associated brachytherapy device into the breast tissue comprises implanting the brachytherapy device within or proximate a lumpectomy cavity.

26. The method of claim 24, wherein the needle comprises a sharp distal tip that extends beyond a distal end of the therapy delivery portion when the device is coupled to the needle, the sharp tip penetrating tissue when the needle and associated brachytherapy device are inserted into the breast tissue.

27. The method of claim 24, wherein the tail portion comprises a device hub attached to the therapy delivery portion and wherein coupling an elongate brachytherapy device to the needle comprises engaging a lock on the needle with the device hub.

28. The method of claim 27, further comprising disengaging the lock on the needle from the device hub before withdrawing the needle from the breast tissue.

29. The method of claim 24, further comprising:
   inserting a removal tool into the lumen of the device after leaving the device implanted within the target region; and
   removing the removal tool and device from the target region.

30. The method of claim 29, wherein the tail portion comprises a device hub attached to the therapy delivery portion, wherein removing the removal tool and device comprises:
   coupling the removal tool to the device hub; and
   removing the removal tool, thereby removing the device from the target region.

* * * * *